(12) United States Patent
Venditti et al.

(10) Patent No.: US 12,201,658 B2
(45) Date of Patent: Jan. 21, 2025

(54) VIRAL GENE THERAPY AS TREATMENT FOR CHOLESTEROL STORAGE DISEASE OR DISORDER

(71) Applicant: The United States of America, as represented by the Secretary, Department of Health and Human Services, Bethesda, MD (US)

(72) Inventors: Charles P. Venditti, Kensington, MD (US); Randy Chandler, Washington, DC (US); William J. Pavan, Derwood, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 17 days.

(21) Appl. No.: 17/033,166

(22) Filed: Sep. 25, 2020

(65) Prior Publication Data

US 2021/0113635 A1    Apr. 22, 2021

Related U.S. Application Data

(62) Division of application No. 15/565,065, filed as application No. PCT/US2016/026524 on Apr. 7, 2016, now abandoned.

(60) Provisional application No. 62/144,702, filed on Apr. 8, 2015.

(51) Int. Cl.
| | |
|---|---|
| *A61K 35/761* | (2015.01) |
| *A61K 48/00* | (2006.01) |
| *A61P 3/00* | (2006.01) |
| *A61P 25/28* | (2006.01) |
| *C07K 14/075* | (2006.01) |
| *C12N 7/04* | (2006.01) |
| *C12N 15/86* | (2006.01) |
| *C12N 15/861* | (2006.01) |

(52) U.S. Cl.
CPC .......... *A61K 35/761* (2013.01); *A61K 48/005* (2013.01); *A61P 3/00* (2018.01); *A61P 25/28* (2018.01); *C07K 14/075* (2013.01); *C12N 7/04* (2013.01); *C12N 15/86* (2013.01); *C12N 15/8616* (2013.01); *C12N 2710/10022* (2013.01); *C12N 2710/10034* (2013.01); *C12N 2710/10045* (2013.01); *C12N 2750/14143* (2013.01)

(58) Field of Classification Search
None
See application file for complete search history.

(56) References Cited

U.S. PATENT DOCUMENTS

| | | |
|---|---|---|
| 4,039,388 A | 8/1977 | Gal et al. |
| 5,328,470 A | 7/1994 | Nabel et al. |
| 5,658,776 A | 8/1997 | Flotte et al. |
| 5,686,240 A | 11/1997 | Schuchman et al. |
| 6,180,613 B1 | 1/2001 | Kaplitt et al. |
| 6,426,198 B1 | 7/2002 | Carstea et al. |
| 6,468,798 B1 | 10/2002 | Debs et al. |
| 6,503,888 B1 | 1/2003 | Kaplitt et al. |
| 6,544,785 B1 | 4/2003 | Palese et al. |
| 7,045,675 B2 | 5/2006 | Carstea et al. |
| 2004/0071659 A1 | 4/2004 | Chang et al. |
| 2006/0171926 A1 | 8/2006 | Passini et al. |
| 2014/0017212 A1 | 1/2014 | Rebar |

FOREIGN PATENT DOCUMENTS

| | | |
|---|---|---|
| CA | 2 946 593 A1 | 11/2015 |
| WO | WO 2009/043936 A1 | 4/2009 |
| WO | WO 2010/0128024 A2 | 11/2010 |
| WO | WO 2011/020118 A1 | 2/2011 |
| WO | WO 2012/061744 A2 | 5/2012 |
| WO | WO 2013/016315 A1 | 1/2013 |
| WO | WO 2016/164642 A | 10/2016 |

OTHER PUBLICATIONS

Nofer et al., CMLS, 2005, 62: 2150-2160.*
Xu et al., JBC, 2012, 287: 39349-39360,.*
Wang et al., Gene Ther., 1999, 6: 667-675.*
Carstea et al., Science, 1997, 277: 228-231.*
Inagaki et al., J. Virol., 2007, 81: 11304-11321.*
Nakai et al., Mol. Ther., 2003, 7: 101-111.*
U.S. Appl. No. 15/565,065, filed Oct. 6, 2017.
Altschul, SF et al., 'Basic local alignment search tool,' J. Mol Biol., 215(3):403-10, (Oct. 1990).
Altschul, SF et al., 'Issues in searching molecular sequence databases,' Nat. Genet., vol. 6, pp. 119-129, (Feb. 1994).
Arnold, DB et al., 'A calcium responsive element that regulates expression of two calcium binding proteins in Purkinje cells,' Proc. Natl. Acad. Sci., vol. 94, pp. 8842-8847, Neurobiology, (Aug. 1997).
Bartlett, JS et al., 'Selective and Rapid Uptake of Adeno-Associated Virus Type 2 in Brain,' Hum. Gene Ther., 9(8):1181-1186, (May 1998).
Carstea, ED et al. 'Niemann-Pick C1 Disease Gene: Homology to Mediators of Cholesterol Homeostasis,' Science, 277(5323): 228-231 (Jul. 1997).
Chen, SH et al., 'Gene therapy for brain tumors: Regression of experimental gliomas by adenovirus-mediated gene transfer in vivo,' Proc. Natl Acad. Sci. USA, vol. 91, pp. 3054-3057, (Apr. 1994).

(Continued)

*Primary Examiner* — Ileana Popa
(74) *Attorney, Agent, or Firm* — Leydig, Voit & Mayer, Ltd.

(57) ABSTRACT

Provided herein are compositions and methods for the viral gene therapy (e.g., AAV-directed gene therapy) of cholesterol storage diseases or disorders, such as Niemann-Pick disease, Type C.

13 Claims, 17 Drawing Sheets

Specification includes a Sequence Listing.

(56) References Cited

OTHER PUBLICATIONS

Clark, KR et al., 'Highly Purified Recombinant Adeno-Associated Virus Vectors are Biologically Active and Free of Detectable Helper and Wild-Type Viruses,' Hum. Gene Ther., 10(6):1031-1039, (Apr. 1999).

Corpet, F et al., 'Multiple sequence alignment with hierarchical clustering,' vol. 16 No. 22, pp. 10881-10890, (Oct. 1988).

De Jesus et al., "Telomerase gene therapy in adult and old mice delays aging and increases longevity without increasing cancer," *EMBO Molecular Medicine*, 4: 691-704 (2012).

Deverman, BE, Cre-dependent selection yields AAV variants for widespread gene transfer to the adult brain, Nat. Biotechnol., 34(2):204-209. doi: 10.1038/nbt.3440. PubMed PMID: 26829320 (Epub Feb. 1, 2016).

Fisher, KJ et al., 'Transduction with Recombinant Adeno-Associated Virus for Gene Therapy is Limited by Leading-Strand Synthesis,' J. Viral., 70(1):520-532 (LFU assay) (Jan. 1996).

Gao, GP et al., 'Novel adeno-associated viruses from rhesus monkeys as vectors for human gene therapy,' PNAS, 99(18):11854-11859 (Sep. 2002).

GenBank Accession No. BC063302 '*Homo sapiens* Niemann-Pick disease, type C1, mRNA (cDNA clone MGC:71703 Image:30340517), complete cds' (2006).

GenBank Accession No. BC117178 '*Homo sapiens* NPC1 (Niemann-Pick disease, type C1, gene)-like 1, mRNA (cDNA clone MGC:150787 Image:40125729), complete cds' (2006).

GenBank Accession No. BC143756 '*Homo sapiens* NPC1 (Niemann-Pick disease, type C1, gene)-like 1, mRNA (cDNA clone MGC:177287 Image:9052270), complete cds' (2009).

GenBank Accession No. AF258783.1 '*Felis catus* Niemann-Pick type C1 disease protein (NPC1) mRNA, complete cds' (2000).

GenBank Accession No. BC054539 '*Mus musculus* Niemann Pick type C1, mRNA (cDNA clone MGC:62352 Image:6405214), complete cds' (2006).

GenBank Accession No. BC151276 '*Bos taurus* Niemann-Pick disease, type C1, mRNA (cDNA clone MGC:152602 Image:8433293), complete cds '(2007).

GenBank Accession No. BC090541 '*Danio rerio* Niemann-Pick disease, type C1, mRNA (cDNA clone Image:7149020), partial cds' (2016).

GenBank Accession No. BC002532 '*Homo sapiens* Niemann-Pick disease, type C2, mRNA (cDNA clone MGC:1333 Image:3140870), complete cds' (2006).

GenBank Accession No. KJ893081 'Synthetic construct *Homo sapiens* clone ccsbBroadEn_02475 NPC2 gene, encodes complete protein' (2015).

GenBank Accession No. BC045895 '*Danio rerio* Niemann-Pick disease, type C2, mRNA (cDNA clone MGC:56070 Image:5409780), complete cds' (2003).

GenBank Accession No. NM_173918 '*Bos taurus* NPC intracellular cholesterol transporter 2 (NPC2), mRNA' (2017).

GenBank Accession No. BC102504 '*Bos taurus* Niemann-Pick disease, type C2, mRNA (cDNA clone MGC:127986 Image:7954223), complete cds' (2007).

GenBank Accession No. NM_214206 '*Sus scrofa* NPC intracellular cholesterol transporter 2 (NPC2), mRNA' (2017).

GenBank Accession No. NM_000271.4 '*Homo sapiens* NPC intracellular cholesterol transporter 1 (NPC1), mRNA' (2017).

GenBank Accession No. NM_008720.2 '*Mus musculus* NPC intracellular cholesterol transporter 1 (Npc1), mRNA' (2017).

GenBank Accession No. NM_006432.3 '*Homo sapiens* NPC intracellular cholesterol transporter 2 (NPC2), mRNA' (2017).

GenBank Accession No. NM_023409.4 '*Mus musculus* NPC intracellular cholesterol transporter 2 (Npc2), mRNA' (2017).

Higgins, DG et al., 'CLUSTAL: a package for performing multiple sequence alignment on a microcomputer,' Gene, 73(1):237-44, (Dec. 1988).

Higgins, DG et al., 'Fast and sensitive multiple sequence alignments on a microcomputer,' Comput Appl Biosci., 5(2):151-3, (Apr. 1989).

Huang, X et al., 'Dynamic programming algorithms for restriction map comparison,' Cabios, vol. 8, No. 5., pp. 511-520, (1992).

International Search Report of International Application No. PCT/US2016/026524, mailed Sep. 1, 2016.

Written Opinion of International Application No. PCT/US2016/026524, mailed Sep. 1, 2016.

Janson, C. et al., 'Clinical protocol. Gene therapy of Canavan disease: AAV-2 vector for neurosurgical delivery of aspartoacylase gene (ASPA) to the human brain,' Hum. Gene Ther., 13(11):1391-1412 (Jul. 2002).

Kaplitt, MG et al., 'Long-term gene expression and phenotypic correction using adeno-associated virus vectors in the mammalian brain,' Nat. Genet., 8(2):148-154, (Oct. 1994).

Loftus, SK et al., 'Murine Model of Niemann-Pick C Disease: Mutation in a Cholesterol Homeostasis Gene,' Science, 277(5323):232-235 (Jul. 1997).

McLaughlin, SK et al., 'Adeno-Associated Virus General Transduction Vectors: Analysis of Proviral Structures,' J. Virol., 62(6):1963-1973 (Jun. 1988).

Muzyscka, N. 'Use of Adeno-Associated Virus as a General Transduction Vector for Mammalian Cells,' Curr. Top Microbiol. Immunol., 158:97-129 (1992).

Needleman, SB et al., 'A general method applicable to the search for similarities in the amino acid sequence of two proteins,' J. Molecular Biology, 48(3):443-53. PMID 5420325. doi:10.1016/0022-2836(70)90057-4, (Mar. 1970).

Nguyen-Vu, TD Barbara et al., 'Cerebellar Purkinje cell activity drives moto learning,' Nature Neuroscience, vol. 16, No. 12, 1734-1736 (Dec. 2013).

Papadakis, ED et al., 'Promoters and Control Elements: Designing Expression Cassettes for Gene Therapy,' Curr. Gene Therapy, vol. 4, No. 1, pp. 89-113, (Mar. 2004).

Passini, MA et al., 'Distribution of a Lysosomal Enzyme in the Adult Brain by Axonal Transport and by Cells of the Rostral Migratory Stream,' J. Neuroscience, 22(15):6437-6446 (Aug. 2002).

Paul, CA et al., 'Adenovirus Expressing an NPCI-GFP Fusion Gene Corrects Neuronal and Nonneuronal Defects Associated With Niemann Pick Type C Disease,' J. Neurosci. Res., vol. 81, No. 5, pp. 706-719 (Sep. 2005).

Pearson, WR et al., 'Improved tools for biological sequence comparison,' Proc. Natl. Acad. Sci., vol. 85, pp. 2444-2448, (Apr. 1988).

Smith, TF et al., 'Identification of Common Molecular Subsequences,' Journal of Molecular Biology, 147:195-197, PMID 7265238. doi:10.1016/0022-2836(81)90087-5, (1981).

Titeux et al., "SIN Retroviral Vectors Expressing COL7A1 Under Human Promoters for Ex Vivo Gene Therapy of Recessive Dystrophic Epidermolysis Bullosa," *Molecular Therapy*, 18(8): 1509-1518 (2010).

University College London (UCL) School of Pharmacy website http://www.ucl.ac.uk/pharmacy/research/disease-models-and-clinical-pharmacology/disease-models-projects/project3, 'Development of Gene Therapy for Niemann-Pick Type C Disease,' (Apr. 2014).

Veldwijk, MR et al., 'Development and optimization of a real-time quantitative PCR-based method for the titration of AAV-2 vector stocks,' Mol. Ther., 6(2):272-8 (Aug. 2002).

Wassif, CA et al., 'High Incidence of Unrecognized Visceral/Neurological Late-onset Niemann-Pick Disease, type C1 Predicted by Analysis of Massively Parallel Sequencing Data Sets,' Genet Med., 18(1):41-48 (Jan. 2016).

Xiao, X. et al., 'Gene Transfer by Adeno-Associated Virus Vectors into the Central Nervous System,' Exp. Neurobiol., 144(1):113-124 (Mar. 1997).

Zhang et al., "Endocytic mechanisms and drug discovery in neurogenerative diseases," *Frontiers in Bioscience*, 13: 6086-6105 (2008).

Zinn, E. 'In silico reconstruction of the viral evolutionary lineage yields a potent gene therapy vector,' Cell Rep., 12(6): 1056-1068 (Aug. 2015).

Nambiar et al., "Characteristics of Minimally Oversized Adeno-Associated Virus Vectors Encoding Human Factor VIII Generated Using Producer Cell Lines and Triple Transfection," *Human Gene Therapy Methods*, 28:1, 23-38 (2017), published online Feb. 2017.

(56) References Cited

OTHER PUBLICATIONS

Brimble et al., "Stowaways in the Cargo: Contaminating Nucleic Acids in rAAV Preparations for Gene Therapy," *Molecular Therapy*, 31(10), 2826-2838 (2023).

Chandler et al., "Recombinant Adeno-Associated Viral Integration and Genotoxicity: Insights from Animal Models," *Human Gene Therapy*, 28(4), 314-322 (2017).

Chandler et al., "Systemic AAV9 Gene Therapy Improves the Lifespan of Mice with Niemann-Pick Disease, Type C1," *Human Molecular Genetics*, 26(1), 52-64 (2017).

Walia et al., "Long-Term Correction of Sandhoff Disease Following Intravenous Delivery of rAAV9 to Mouse Neonates," *Molecular Therapy*, 23(3), 414-422 (Mar. 2015).

Xie et al., "AAV9-NPC1 significantly ameliorates Purkinje cell death and behavioral abnormalities in mouse NPC disease," *Molecular Therapy*, vol. 58, 514-518 (2017).

Xie et al., "Genome Editing with CRISPR/Cas9 in Postnatal Mice Corrects PRKAG2 Cardiac Syndrome," *Cell Research*, 26(10), 1099-1111 (2016).

\* cited by examiner

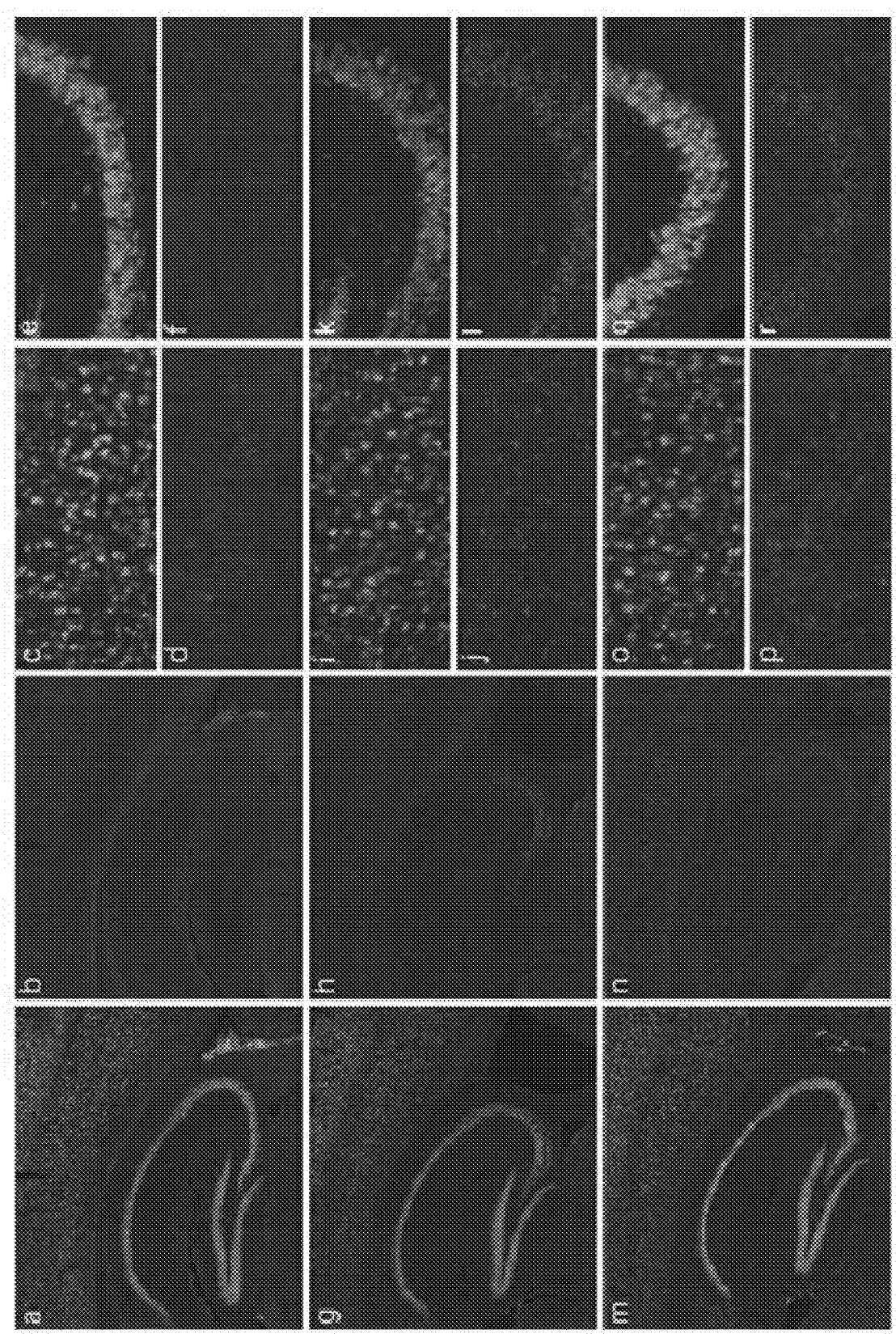
FIG. 6A-R

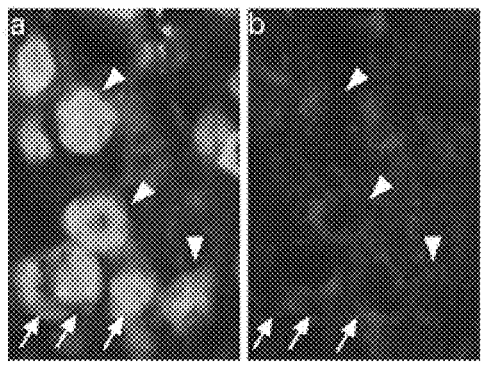
FIG. 7A-B
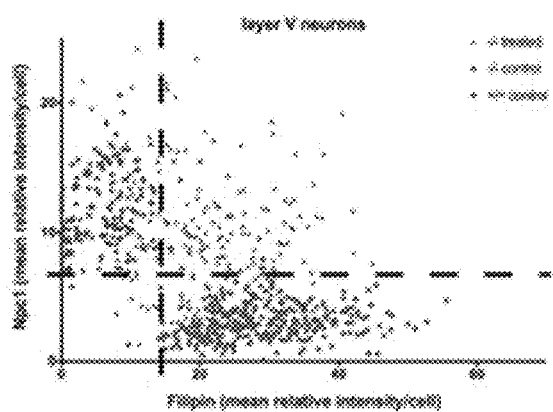
FIG. 7C
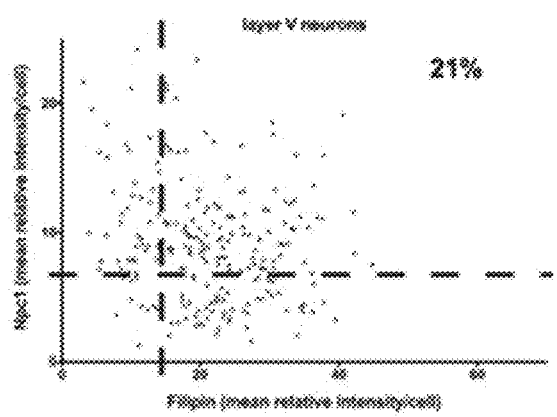
FIG. 7D
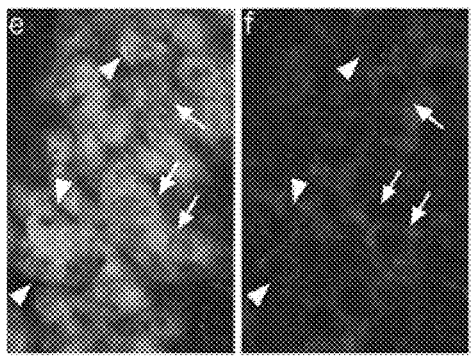
FIG. 7E-F

FIG. 7I-L

* Age at which ~ 50% of untreated $Npc1^{-/-}$ mice die
** Age at which ~ 100% of AAV9-miniCaMKII-NPC1 treated $Npc1^{-/-}$ mice die

SEQUENCE LISTING

<160> NUMBER OF SEQ ID NOS: 12

<210> SEQ ID NO 1
<211> LENGTH: 7654
<212> TYPE: DNA
<213> ORGANISM: Artificial Sequence
<220> FEATURE:
<223> OTHER INFORMATION: Synthetic

<400> SEQUENCE: 1

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctaccag ggtaatgggg    180
atcctctaga actatagcta gcatgcctaa cttgtggact aagtttgttc acatcccctt     240
```

```
ctccaacccc ctcagtacat caccctgggg aacagggtc cacttgctcc tgggcccaca      300
cagtcctgca gtattgtgta tataaggcca gggcaaagag gagcaggttt taaagtgaaa      360
ggcaggcagg tgttggggag gcagttaccg gggcaacggg aacagggcgt ttcggaggtg      420
gttgccatgg ggacctggat gctgacgaag gctcgcgagg ctgtgagcag ccacagtgcc      480
ctgctcagaa gccccaagct cgtcagtcaa gccggttctc cgtttgcact caggagcacg      540
ggcaggcgag tggcccctag ttctgggggc agctctagag ccgatcccg ggtaaattcg       600 gcacgagccg gcgtccgcag ccttgcgcgg ccacagcatg accgctcgcg gcctggccct      660
tggcctcctc ctgctgctac tgtgtccagc gcaggtgttt tcacagtcct gtgtttggta      720
tggagagtgt ggaattgcat atggggacaa gaggtacaat tgcgaatatt ctggcccacc      780
aaaaccattg ccaaaggatg gatatgactt agtgcaggaa ctctgtccag gattcttctt      840
tggcaatgtc agtctctgtt gtgatgttcg gcagcttcag acactaaaag acaacctgca      900
gctgcctcta cagtttctgt ccagatgtcc atcctgtttt tataacctac tgaacctgtt      960
ttgtgagctg acatgtagcc ctcgacagag tcagtttttg aatgttacag ctactgaaga     1020
ttatgttgat cctgttacaa accagacgaa aacaaatgtg aaagagttac aatactacgt     1080
cggacagagt tttgccaatg caatgtacaa tgcctgccgg gatgtggagg cccctcaag      1140 taatgacaag gccctgggac tcctgtgtgg aaggacgct gacgcctgta atgccaccaa      1200
ctggattgaa tacatgttca ataaggacaa tggacaggca cctttaccca tcactcctgt     1260
gttttcagat tttccagtcc atgggatgga gcccatgaac aatgccacca aaggctgtga     1320
cgagtctgtg gatgaggtca cagcaccatg tagctgccaa gactgctcta ttgtctgtgg     1380 cccccaagccc cagcccccac ctcctcctgc tccctggacg atccttggct tggacgccat    1440
gtatgtcatc atgtggatca cctacatggc gttttttgctt gtgtttttg gagcattttt     1500 tgcagtgtgg tgctacagaa aacggtattt tgtctccgag tacactccca tcgatagcaa     1560
tatagctttt tctgttaatg caagtgacaa aggagaggcg tcctgctgtg accctgtcag     1620
cgcagcattt gagggctgct tgaggcggct gttcacacgc tgggggtctt tctgcgtccg     1680
aaaccctggc tgtgtcattt tcttctcgct ggtcttcatt actgcgtgtt cgtcaggcct     1740
ggtgtttgtc cgggtcacaa ccaatccagt tgacctctgg tcagccccca gcagccaggc     1800
tcgcctggaa aaagagtact ttgaccagca ctttgggcct ttcttccgga cggagcagct     1860
catcatccgg gcccctctca ctgacaaaca catttaccag ccatacctt cgggagctga     1920 tgtaccttt ggacctccgc ttgacataca gatactgcac caggttcttg acttacaaat      1980
agccatcgaa acattactg cctcttatga caatgagact gtgacacttc aagacatctg      2040
cttggcccct ctttcaccgt ataacacgaa ctgcaccatt ttgagtgtgt taaattactt     2100
ccagaacagc cattccgtgc tggaccacaa gaaagggac gacttctttg tgtatgccga      2160
ttaccacacg cactttctgt actgcgtacg ggctcctgcc tctctgaatg atacaagttt     2220
gctccatgac ccttgtctgg gtacgtttgg tggaccagtg ttcccgtggc ttgtgttggg     2280
aggctatgat gatcaaaaact acaataacgc cactgccctt gtgattacct tccctgtcaa     2340
taattactat aatgatacag agaagctcca gagggcccag gcctgggaaa aagagtttat     2400
taattttgtg aaaaactaca agaatcccaa tctgaccatt tccttcactg ctgaacgaag     2460
tattgaagat gaactaaatc gtgaaagtga cagtgatgtc ttcaccgttg taattagcta     2520
tgccatcatg tttctatata tttccctagc cttggggcac atcaaaagct gtcgcaggct     2580
```

```
tctggtggat tcgaaggtct cactaggcat cgcgggcatc ttgatcgtgc tgagctcggt    2640
ggcttgctcc ttgggtgtct tcagctacat tgggttgccc ttgaccctca ttgtgattga    2700
agtcatcccg ttcctggtgc tggctgttgg agtggacaac atcttcattc tggtgcaggc    2760
ctaccagaga gatgaacgtc ttcaagggga acccctggat cagcagctgg gcagggtcct    2820
aggagaagtg gctcccagta tgttcctgtc atccttttct gagactgtag cattttttctt   2880 aggagcattg tccgtgatgc cagccgtgca ccttctctct ctctttgcgg gattggcagt    2940
cttcattgac tttcttctgc agattacctg tttcgtgagt ctcttggggt tagacattaa    3000
acgtcaagag aaaaatcggc tagacatctt ttgctgtgtc agaggtgctg aagatggaac    3060
aagcgtccag gcctcagaga gctgtttgtt tcgcttcttc aaaaactcct attctccact    3120
tctgctaaag gactggatga gaccaattgt gatagcaata tttgtgggtg ttctgtcatt    3180
cagcatcgca gtcctgaaca agtagatat tggattggat cagtctcttt cgatgccaga    3240
tgactcctac atggtggatt atttcaaatc catcagtcag tacctgcatg cgggtccgcc    3300
tgtgtacttt gtcctggagg aagggcacga ctacacttct tccaagggc agaacatggt    3360 gtgcggcggc atgggctgca acaatgattc cctggtgcag cagatattta acgcggcgca    3420
gctggacaac tatacccgaa taggcttcgc cccctcgtcc tggatcgacg attatttcga    3480
ctgggtgaag ccacagtcgt cttgctgtcg agtggacaat atcactgacc agttctgcaa    3540
tgcttcagtg gttgaccctg cctgcgttcg ctgcaggcct ctgactccgg aaggcaaaca    3600
gaggcctcag gggggagact tcatgagatt cctgcccatg ttcctttcgg ataaccctaa    3660
ccccaagtgt ggcaaagggg acatgctgc ctatagttct gcagttaaca tcctccttgg    3720
ccatggcacc agggtcggag ccacgtactt catgacctac cacaccgtgc tgcagacctc    3780
tgctgacttt attgacgctc tgaagaaagc ccgacttata gccagtaatg tcaccgaaac    3840
catgggcatt aacggcagtg cctaccgagt atttccttac agtgtgtttt atgtcttcta    3900
cgaacagtac ctgaccatca ttgacgcaca tatcttcaac ctcggtgtgt ccctgggcgc    3960
gatatttctg gtgaccatgg tcctcctggg ctgtgagctc tggtctgcag tcatcatgtg    4020
tgccaccatc gccatggtct tggtcaacat gtttggagtt atgtggctct ggggcatcag    4080
tctgaacgct gtatccttgg tcaacctggt gatgagctgt ggcatctccg tggagttctg    4140
cagccacata accagagcgt tcacggtgag catgaaaggc agccgcgtgg agcgcgcgga    4200
agaggcactt gcccacatgg gcagctccgt gttcagtgga atcacactta caaaatttgg    4260
agggattgtg gtgttggctt ttgccaaatc tcaaattttc cagatattct acttcaggat    4320
gtatttggcc atggtcttac tgggagccac tcacggatta atatttctcc ctgtcttact    4380
cagttacata gggccatcag taaataaagc caaaagttgt gccactgaag agcgatacaa    4440
aggaacagag cgcgaacggc ttctaaattt ctagccctct gaggatccga tcttttttccc    4500 tctgccaaaa attatgggga catcatgaag cccttgagc atctgacttc tggctaataa    4560
aggaaattta ttttcattgc aatagtgtgt tggaatttt tgtgtctctc actcggaagc    4620
aattcgttga tctgaatttc gaccaccat aatacccatt accctggtag ataagtagca    4680
tggcgggtta atcattaact acaaggaacc cctagtgatg gagttggcca ctccctctct    4740
gcgcgctcgc tcgctcactg aggccgggcg accaaaggtc gcccgacgcc cgggctttgc    4800
ccgggcggcc tcagtgagcg agcgagcgcg cagccttaat taacctaatt cactggccgt    4860
cgttttacaa cgtcgtgact gggaaaaccc tggcgttacc caacttaatc gccttgcagc    4920 acatcccccct ttcgccagct ggcgtaatag cgaagaggcc cgcaccgatc gcccttccca    4980
```

```
acagttgcgc agcctgaatg gcgaatggga cgcgccctgt agcggcgcat taagcgcggc    5040
gggtgtggtg gttacgcgca gcgtgaccgc tacacttgcc agcgccctag cgcccgctcc    5100
tttcgctttc ttcccttcct ttctcgccac gttcgccggc tttccccgtc aagctctaaa    5160
tcggggggctc cctttagggt tccgatttag tgctttacgg cacctcgacc ccaaaaaact    5220
tgattagggt gatggttcac gtagtgggcc atcgccctga tagacggttt ttcgcccttt    5280
gacgttggag tccacgttct ttaatagtgg actcttgttc caaactggaa caacactcaa    5340
ccctatctcg gtctattctt ttgatttata agggattttg ccgatttcgg cctattggtt    5400
aaaaaatgag ctgatttaac aaaaatttaa cgcgaatttt aacaaaatat taacgcttac    5460
aatttaggtg cacttttcg gggaaatgtg cgcggaaccc ctatttgttt attttctaa     5520
atacattcaa atatgtatcc gctcatgaga caataaccct gataaatgct tcaataatat    5580
tgaaaaagga agagtatgag tattcaacat ttccgtgtcg cccttattcc cttttttgcg    5640
gcatttttgcc ttcctgtttt tgctcaccca gaaacgctgg tgaaagtaaa agatgctgaa    5700
gatcagttgg gtgcacgagt gggttacatc gaactggatc tcaacagcgg taagatcctt    5760
gagagttttc gccccgaaga acgttttcca atgatgagca cttttaaagt tctgctatgt    5820
ggcgcggtat tatcccgtat tgacgccggg caagagcaac tcggtcgccg catacactat    5880
tctcagaatg acttggttga gtactcacca gtcacagaaa agcatcttac ggatggcatg    5940
acagtaagag aattatgcag tgctgccata accatgagtg ataacactgc ggccaactta    6000
cttctgacaa cgatcggagg accgaaggag ctaaccgctt ttttgcacaa catgggggat    6060
catgtaactc gccttgatcg ttgggaaccg gagctgaatg aagccatacc aaacgacgag    6120
cgtgacacca cgatgcctgt agcaatggca acaacgttgc gcaaactatt aactggcgaa    6180
ctacttactc tagcttcccg gcaacaatta atagactgga tggaggcgga taaagttgca    6240
ggaccacttc tgcgctcggc ccttccggct ggctggttta ttgctgataa atctggagcc    6300
ggtgagcgtg ggtctcgcgg tatcattgca gcactggggc cagatggtaa gccctcccgt    6360
atcgtagtta tctacacgac ggggagtcag gcaactatgg atgaacgaaa tagacagatc    6420
gctgagatag gtgcctcact gattaagcat tggtaactgt cagaccaagt ttactcatat    6480
atactttaga ttgatttaaa acttcatttt taatttaaaa ggatctaggt gaagatcctt    6540
tttgataatc tcatgaccaa aatcccttaa cgtgagtttt cgttccactg agcgtcagac    6600
cccgtagaaa agatcaaagg atcttcttga gatcctttt tctgcgcgt aatctgctgc     6660
ttgcaaacaa aaaaaccacc gctaccagcg gtggtttgtt tgccggatca agagctacca    6720
actcttttc cgaaggtaac tggcttcagc agagcgcaga taccaaatac tgttcttcta    6780
gtgtagccgt agttaggcca ccacttcaag aactctgtag caccgcctac atacctcgct    6840
ctgctaatcc tgttaccagt ggctgctgcc agtggcgata agtcgtgtct taccgggttg    6900
gactcaagac gatagttacc ggataaggcg cagcggtcgg gctgaacggg gggttcgtgc    6960
acacagccca gcttggagcg aacgacctac accgaactga gatacctaca gcgtgagcta    7020
tgagaaagcg ccacgcttcc cgaagggaga aaggcggaca ggtatccggt aagcggcagg    7080
gtcggaacag gagagcgcac gagggagctt ccagggggaa acgcctggta tctttatagt    7140
cctgtcgggt ttcgccacct ctgacttgag cgtcgatttt tgtgatgctc gtcagggggg    7200
cggagcctat ggaaaaacgc cagcaacgcg gcctttttac ggttcctggc cttttgctgg    7260
ccttttgctc acatgttctt tcctgcgtta tcccctgatt ctgtggataa ccgtattacc    7320
```

```
gcctttgagt gagctgatac cgctcgccgc agccgaacga ccgagcgcag cgagtcagtg    7380
agcgaggaag cggaagagcg cccaatacgc aaaccgcctc tccccgcgcg ttggccgatt    7440
cattaatgca gctggcacga caggtttccc gactggaaag cgggcagtga gcgcaacgca    7500
attaatgtga gttagctcac tcattaggca ccccaggctt tacactttat gcttccggct    7560
cgtatgttgt gtggaattgt gagcggataa caatttcaca caggaaacag ctatgaccat    7620
gattacgcca gatttaatta aggccttaat tagg                                7654

<210> SEQ ID NO 2
<211> LENGTH: 130
<212> TYPE: DNA
<213> ORGANISM: Artificial Sequence
<220> FEATURE:
<223> OTHER INFORMATION: Synthetic

<400> SEQUENCE: 2
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct                                                           130

<210> SEQ ID NO 3
<211> LENGTH: 255
<212> TYPE: DNA
<213> ORGANISM: Artificial Sequence
<220> FEATURE:
<223> OTHER INFORMATION: Synthetic

<400> SEQUENCE: 3
taacttgtgg actaagtttg ttcacatccc cttctccaac cccctcagta catcaccctg     60
ggggaacagg gtccacttgc tcctgggccc acacagtcct gcagtattgt gtatataagg    120
ccagggcaaa gaggagcagg ttttaaagtg aaaggcaggc aggtgttggg gaggcagtta    180
ccggggcaac gggaacaggg cgtttcggag gtggttgcca tggggacctg gatgctgacg    240
aaggctcgcg aggct                                                    255

<210> SEQ ID NO 4
<211> LENGTH: 3837
<212> TYPE: DNA
<213> ORGANISM: Artificial Sequence
<220> FEATURE:
<223> OTHER INFORMATION: Synthetic

<400> SEQUENCE: 4
atgaccgctc gcggcctggc ccttggcctc ctcctgctgc tactgtgtcc agcgcaggtg     60
ttttcacagt cctgtgtttg gtatggagag tgtggaattg catatgggga caagaggtac    120
aattgcgaat attctggccc accaaaacca ttgccaaagg atggatatga cttagtgcag    180
gaactctgtc caggattctt cttttggcaat gtcagtctct gttgtgatgt tcggcagctt    240
cagacactaa aagacaacct gcagctgcct ctacagtttc tgtccagatg tccatcctgt    300
ttttataacc tactgaacct gttttgtgag ctgacatgta gccctcgaca gagtcagttt    360
ttgaatgtta cagctactga agattatgtt gatcctgtta caaaccagac gaaaacaaat    420
gtgaaagagt tacaatacta cgtcggacag agttttgcca atgcaatgta caatgcctgc    480
cgggatgtgg aggccccctc aagtaatgac aaggccctgg gactcctgtg tgggaaggac    540
gctgacgcct gtaatgccac caactggatt gaatacatgt tcaataagga caatggacag    600
gcaccttttt ccatcactcc tgtgttttca gattttccag tccatgggat ggagcccatg    660
```

```
aacaatgcca ccaaaggctg tgacgagtct gtggatgagg tcacagcacc atgtagctgc    720
caagactgct ctattgtctg tggccccaag ccccagcccc cacctcctcc tgctccctgg    780
acgatccttg gcttggacgc catgtatgtc atcatgtgga tcacctacat ggcgttttg    840
cttgtgtttt ttggagcatt ttttgcagtg tggtgctaca gaaaacggta ttttgtctcc    900
gagtacactc ccatcgatag caatatagct ttttctgtta atgcaagtga caaaggagag    960
gcgtcctgct gtgaccctgt cagcgcagca tttgagggct gcttgaggcg gctgttcaca   1020
cgctgggggt ctttctgcgt ccgaaaccct ggctgtgtca ttttcttctc gctggtcttc   1080
attactgcgt gttcgtcagg cctggtgttt gtccgggtca caaccaatcc agttgacctc   1140
tggtcagccc ccagcagcca ggctcgcctg gaaaagagt actttgacca gcactttggg   1200
cctttcttcc ggacggagca gctcatcatc cgggcccctc tcactgacaa acacatttac   1260
cagccatacc cttcgggagc tgatgtaccc tttggacctc cgcttgacat acagatactg   1320
caccaggttc ttgacttaca aatagccatc gaaaacatta ctgcctctta tgacaatgag   1380
actgtgacac ttcaagacat ctgcttggcc cctctttcac cgtataacac gaactgcacc   1440
attttgagtg tgttaaatta cttccagaac agccattccg tgctggacca caagaaaggg   1500
gacgacttct ttgtgtatgc cgattaccac acgcactttc tgtactgcgt acgggctcct   1560
gcctctctga atgatacaag tttgctccat gaccccttgtc tgggtacgtt tggtggacca   1620
gtgttcccgt ggcttgtgtt gggaggctat gatgatcaaa actacaataa cgccactgcc   1680
cttgtgatta ccttccctgt caataattac tataatgata cagagaagct ccagagggcc   1740
caggcctggg aaaaagagtt tattaattt gtgaaaaact acaagaatcc caatctgacc   1800
atttccttca ctgctgaacg aagtattgaa gatgaactaa atcgtgaaag tgacagtgat   1860
gtcttcaccg ttgtaattag ctatgccatc atgtttctat atatttccct agccttgggg   1920
cacatcaaaa gctgtcgcag gcttctggtg gattcgaagg tctcactagg catcgcgggc   1980
atcttgatcg tgctgagctc ggtggcttgc tccttgggtg tcttcagcta cattgggttg   2040
cccttgaccc tcattgtgat tgaagtcatc ccgttcctgg tgctggctgt tggagtggac   2100
aacatcttca ttctggtgca ggcctaccag agagatgaac gtcttcaagg ggaaaccctg   2160
gatcagcagc tgggcagggt cctaggagaa gtggctccca gtatgttcct gtcatccttt   2220
tctgagactg tagcattttt cttaggagca ttgtccgtga tgccagccgt gcacaccttc   2280
tctctctttg cgggattggc agtcttcatt gactttcttc tgcagattac ctgtttcgtg   2340
agtctcttgg ggttagacat taaacgtcaa gagaaaaatc ggctagacat cttttgctgt   2400
gtcagaggtg ctgaagatgg aacaagcgtc caggcctcag agagctgttt gtttcgcttc   2460
ttcaaaaact cctattctcc acttctgcta aaggactgga tgagaccaat tgtgatagca   2520
atatttgtgg gtgttctgtc attcagcatc gcagtcctga caaagtaga tattggattg   2580
gatcagtctc tttcgatgcc agatgactcc tacatggtgg attatttcaa atccatcagt   2640
cagtacctgc atgcgggtcc gcctgtgtac tttgtcctgg aggaagggca cgactacact   2700
tcttccaagg ggcagaacat ggtgtgcggc ggcatgggct gcaacaatga ttcccctggtg   2760
cagcagatat ttaacgcggc gcagctggac aactataccc gaataggctt cgcccctcg   2820
tcctggatcg acgattattt cgactgggtg aagccacagt cgtcttgctg tcgagtggac   2880
aatatcactg accagttctg caatgcttca gtggttgacc ctgcctgcgt tcgctgcagg   2940
cctctgactc cggaaggcaa acagaggcct caggggggag acttcatgag attcctgccc   3000
```

| | |
|---|---|
| atgttcctttt cggataaccc taaccccaag tgtggcaaag ggggacatgc tgcctatagt | 3060 |
| tctgcagtta acatcctcct tggccatggc accagggtcg gagccacgta cttcatgacc | 3120 |
| taccacaccg tgctgcagac ctctgctgac tttattgacg ctctgaagaa agcccgactt | 3180 |
| atagccagta atgtcaccga aaccatgggc attaacggca gtgcctaccg agtatttcct | 3240 |
| tacagtgtgt tttatgtctt ctacgaacag tacctgacca tcattgacga cactatcttc | 3300 |
| aacctcggtg tgtccctggg cgcgatattt ctggtgacca tggtcctcct gggctgtgag | 3360 |
| ctctggtctg cagtcatcat gtgtgccacc atcgccatgg tcttggtcaa catgtttgga | 3420 |
| gttatgtggc tctggggcat cagtctgaac gctgtatcct tggtcaacct ggtgatgagc | 3480 |
| tgtggcatct ccgtggagtt ctgcagccac ataaccagag cgttcacggt gagcatgaaa | 3540 |
| ggcagccgcg tggagcgcgc ggaagaggca cttgcccaca tgggcagctc cgtgttcagt | 3600 |
| ggaatcacac ttacaaaatt tggagggatt gtggtgttgg cttttgccaa atctcaaatt | 3660 |
| ttccagatat tctacttcag gatgtatttg gccatggtct tactgggagc cactcacgga | 3720 |
| ttaatatttc tccctgtctt actcagttac atagggccat cagtaaataa agccaaaagt | 3780 |
| tgtgccactg aagagcgata caaaggaaca gagcgcgaac ggcttctaaa tttctag | 3837 |

<210> SEQ ID NO 5
<211> LENGTH: 127
<212> TYPE: DNA
<213> ORGANISM: Artificial Sequence
<220> FEATURE:
<223> OTHER INFORMATION: Synthetic

<400> SEQUENCE: 5

| | |
|---|---|
| gatctttttc cctctgccaa aaattatggg gacatcatga agcccttga gcatctgact | 60 |
| tctggctaat aaaggaaatt tattttcatt gcaatagtgt gttggaattt tttgtgtctc | 120 |
| tcactcg | 127 |

<210> SEQ ID NO 6
<211> LENGTH: 130
<212> TYPE: DNA
<213> ORGANISM: Artificial Sequence
<220> FEATURE:
<223> OTHER INFORMATION: Synthetic

<400> SEQUENCE: 6

| | |
|---|---|
| aggaacccct agtgatggag ttggccactc cctctctgcg cgctcgctcg ctcactgagg | 60 |
| ccgggcgacc aaaggtcgcc cgacgcccgg gctttgcccg gcggcctca gtgagcgagc | 120 |
| gagcgcgcag | 130 |

<210> SEQ ID NO 7
<211> LENGTH: 7559
<212> TYPE: DNA
<213> ORGANISM: Artificial Sequence
<220> FEATURE:
<223> OTHER INFORMATION: Synthetic

<400> SEQUENCE: 7

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctaccag gtaatgggg | 180 |
| atcctctaga gctccggtgc ccgtcagtgg gcagagcgca catcgcccac agtccccgag | 240 |
| aagttggggg gaggggtcgg caattgaacc ggtgcctaga aaggtggcg cggggtaaac | 300 |

```
tgggaaagtg atgtcgtgta ctggctccgc cttttcccg agggtggggg agaaccgtat     360
ataagtgcag tagtcgccgt gaacgttctt tttcgcaacg ggtttgccgc cagaacacgc     420
gtaagggcga attccagcac actggcggcc gttactagcc tcgagaattg tacaattcac     480
gcgggccgcc aatgaccgct cgcggcctgg cccttggcct cctcctgctg ctactgtgtc     540
cagcgcaggt gttttcacag tcctgtgttt ggtatggaga gtgtggaatt gcatatgggg     600
acaagaggta caattgcgaa tattctggcc caccaaaacc attgccaaag gatggatatg     660
acttagtgca ggaactctgt ccaggattct tctttggcaa tgtcagtctc tgttgtgatg     720
ttcggcagct tcagacacta aagacaacc tgcagctgcc tctacagttt ctgtccagat     780
gtccatcctg tttttataac ctactgaacc tgttttgtga gctgacatgt agccctcgac     840
agagtcagtt tttgaatgtt acagctactg aagattatgt tgatcctgtt acaaaccaga     900
cgaaaacaaa tgtgaaagag ttacaatact acgtcggaca gagttttgcc aatgcaatgt     960
acaatgcctg ccgggatgtg gaggccccct caagtaatga caaggccctg ggactcctgt    1020
gtgggaagga cgctgacgcc tgtaatgcca ccaactggat tgaatacatg ttcaataagg    1080
acaatggaca ggcacctttt accatcactc ctgtgttttc agattttcca gtccatggga    1140
tggagcccat gaacaatgcc accaaaggct gtgacgagtc tgtggatgag gtcacagcac    1200
catgtagctg ccaagactgc tctattgtct gtggccccaa gccccagccc ccacctcctc    1260
ctgctccctg gacgatcctt ggcttggacg ccatgtatgt catcatgtgg atcacctaca    1320
tggcgttttt gcttgtgttt tttgagcat ttttttgcagt gtggtgctac agaaaacggt    1380
attttgtctc cgagtacact cccatcgata gcaatatagc ttttctgtt aatgcaagtg    1440 acaaaggaga ggcgtcctgc tgtgaccctg tcagcgcagc atttgagggc tgcttgaggc    1500
ggctgttcac acgctggggg tctttctgcg tccgaaaccc tggctgtgtc atttcttct    1560 cgctggtctt cattactgcg tgttcgtcag gcctggtgtt tgtccgggtc acaaccaatc    1620
cagttgacct ctggtcagcc cccagcagcc aggctcgcct ggaaaaagag tactttgacc    1680
agcactttgg gcctttcttc cggacggagc agctcatcat ccgggcccct ctcactgaca    1740
aacacattta ccagccatac ccttcgggag ctgatgtacc ctttggacct ccgcttgaca    1800
tacagatact gcaccaggtt cttgacttac aaatagccat cgaaaacatt actgcctctt    1860
atgacaatga gactgtgaca cttcaagaca tctgcttggc ccctctttca ccgtataaca    1920
cgaactgcac cattttgagt gtgttaaatt acttccagaa cagccattcc gtgctggacc    1980
acaagaaagg ggacgacttc tttgtgtatg ccgattacca cacgcacttt ctgtactgcg    2040
tacgggctcc tgcctctctg aatgatacaa gtttgctcca tgaccccttgt ctgggtacgt    2100 ttggtggacc agtgttcccg tggcttgtgt tgggaggcta tgatgatcaa aactacaata    2160
acgccactgc ccttgtgatt accttccctg tcaataatta ctataatgat acagagaagc    2220
tccagagggc ccaggcctgg gaaaaagagt ttattaattt tgtgaaaaac tacaagaatc    2280
ccaatctgac catttccttc actgctgaac gaagtattga agatgaacta atcgtgaaa    2340 gtgacagtga tgtcttcacc gttgtaatta gctatgccat catgtttcta tatatttccc    2400
tagccttggg gcacatcaaa agctgtcgca ggcttctggt ggattcgaag gtctcactag    2460
gcatcgcggg catcttgatc gtgctgagct cggtggcttg ctccttgggt gtcttcagct    2520
acattgggtt gccccttgacc ctcattgtga ttgaagtcat cccgttcctg gtgctggctg    2580
ttggagtgga caacatcttc attctggtgc aggcctacca gagagatgaa cgtcttcaag    2640
```

-continued

```
gggaaaccct ggatcagcag ctgggcaggg tcctaggaga agtggctccc agtatgttcc    2700
tgtcatcctt ttctgagact gtagcatttt tcttaggagc attgtccgtg atgccagccg    2760
tgcacacctt ctctctcttt gcgggattgg cagtcttcat tgactttctt ctgcagatta    2820
cctgtttcgt gagtctcttg gggttagaca ttaaacgtca agagaaaaat cggctagaca    2880
tcttttgctg tgtcagaggt gctgaagatg aacaagcgt ccaggcctca gagagctgtt    2940
tgtttcgctt cttcaaaaac tcctattctc cacttctgct aaaggactgg atgagaccaa    3000
ttgtgatagc aatatttgtg ggtgttctgt cattcagcat cgcagtcctg aacaaagtag    3060
atattggatt ggatcagtct ctttcgatgc cagatgactc ctacatggtg gattatttca    3120
aatccatcag tcagtacctg catgcgggtc cgcctgtgta ctttgtcctg gaggaagggc    3180
acgactacac ttcttccaag gggcagaaca tggtgtgcgg cggcatgggc tgcaacaatg    3240
attccctggt gcagcagata tttaacgcgg cgcagctgga caactatacc cgaataggct    3300 tcgcccctc gtcctggatc gacgattatt tcgactgggt gaagccacag tcgtcttgct    3360
gtcgagtgga caatatcact gaccagttct gcaatgcttc agtggttgac cctgcctgcg    3420
ttcgctgcag gcctctgact ccggaaggca acagaggcc tcaggggga gacttcatga    3480 gattcctgcc catgttcctt tcggataacc ctaaccccaa gtgtggcaaa gggggacatg    3540
ctgcctatag ttctgcagtt aacatcctcc ttggccatgg caccagggtc ggagccacgt    3600
acttcatgac ctaccacacc gtgctgcaga cctctgctga cttattgac gctctgaaga    3660 aagcccgact tatagccagt aatgtcaccg aaaccatggg cattaacggc agtgcctacc    3720
gagtatttcc ttacagtgtg ttttatgtct tctacgaaca gtacctgacc atcattgacg    3780
acactatctt caacctcggt gtgtccctgg gcgcgatatt tctggtgacc atggtcctcc    3840
tgggctgtga gctctggtct gcagtcatca tgtgtgccac catcgccatg gtcttggtca    3900
acatgtttgg agttatgtgg ctctggggca tcagtctgaa cgctgtatcc ttggtcaacc    3960
tggtgatgag ctgtggcatc tccgtggagt tctgcagcca cataaccaga gcgttcacgg    4020
tgagcatgaa aggcagccgc gtggagcgcg cggaagaggc acttgcccac atgggcagct    4080
ccgtgttcag tggaatcaca cttacaaaat tggagggat tgtggtgttg cttttgcca    4140 aatctcaaat tttccagata ttctacttca ggatgtattt ggccatggtc ttactgggag    4200
ccactcacgg attaatattt ctccctgtct tactcagtta catagggcca tcagtaaata    4260
aagccaaaag ttgtgccact gaagagcgat acaaaggaac agagcgcgaa cggcttctaa    4320
atttctagta ataagctcgc gtgatcacga cccgggcggc ctcgaggacg gggtgaacta    4380
cgcctgagga tccgatcttt ttccctctgc caaaaattat ggggacatca tgaagcccct    4440
tgagcatctg acttctggct aataaaggaa atttattttc attgcaatag tgtgttggaa    4500
ttttttgtgt ctctcactcg gaagcaattc gttgatctga atttcgacca cccataatac    4560
ccattaccct ggtagataag tagcatggcg ggttaatcat taactacaag gaaccccta    4620 tgatggagtt ggccactccc tctctgcgcg ctcgctcgct cactgaggcc gggcgaccaa    4680
aggtcgcccg acgcccgggc tttgcccggg cggcctcagt gagcgagcga gcgcgcagcc    4740
ttaattaacc taattcactg gccgtcgttt tacaacgtcg tgactgggaa accctggcg    4800 ttacccaact taatcgcctt gcagcacatc cccctttcgc cagctggcgt aatagcgaag    4860
aggcccgcac cgatcgccct tcccaacagt tgcgcagcct gaatggcgaa tgggacgcgc    4920
cctgtagcgc gcattaagc gcggcgggtg tggtggttac gcgcagcgtg accgctacac    4980
ttgccagcgc cctagcgccc gctcctttcg ctttcttccc ttcctttctc gccacgttcg    5040
```

```
ccggctttcc ccgtcaagct ctaaatcggg ggctcccttt agggttccga tttagtgctt    5100
tacggcacct cgaccccaaa aaacttgatt agggtgatgg ttcacgtagt gggccatcgc    5160
cctgatagac ggttttcgc cctttgacgt tggagtccac gttctttaat agtggactct    5220
tgttccaaac tggaacaaca ctcaacccta tctcggtcta ttcttttgat ttataaggga    5280
ttttgccgat tcggcctat tggttaaaaa atgagctgat ttaacaaaaa tttaacgcga    5340 atttaacaa aatattaacg cttacaattt aggtggcact tttcggggaa atgtgcgcgg    5400
aacccctatt tgtttatttt tctaaataca ttcaaatatg tatccgctca tgagacaata    5460
accctgataa atgcttcaat aatattgaaa aggaagagt atgagtattc aacatttccg    5520
tgtcgccctt attccttttt ttgcggcatt ttgccttcct gttttgctc acccagaaac    5580 gctggtgaaa gtaaaagatg ctgaagatca gttgggtgca cgagtgggtt acatcgaact    5640
ggatctcaac agcggtaaga tccttgagag ttttcgcccc gaagaacgtt ttccaatgat    5700
gagcactttt aaagtctgc tatgtggcgc ggtattatcc cgtattgacg ccgggcaaga    5760
gcaactcggt cgccgcatac actattctca gaatgacttg gttgagtact caccagtcac    5820
agaaaagcat cttacggatg gcatgacagt aagagaatta tgcagtgctg ccataaccat    5880
gagtgataac actgcggcca acttacttct gacaacgatc ggaggaccga aggagctaac    5940
cgcttttttg cacaacatgg gggatcatgt aactcgcctt gatcgttggg aaccggagct    6000
gaatgaagcc ataccaaacg acgagcgtga caccacgatg cctgtagcaa tggcaacaac    6060
gttgcgcaaa ctattaactg gcgaactact tactctagct tcccggcaac aattaataga    6120
ctggatggag gcggataaag ttgcaggacc acttctgcgc tcggcccttc cggctggctg    6180
gtttattgct gataaatctg gagccggtga gcgtgggtct cgcggtatca ttgcagcact    6240
ggggccagat ggtaagccct cccgtatcgt agttatctac acgacgggga gtcaggcaac    6300
tatggatgaa cgaaatagac agatcgctga gataggtgcc tcactgatta gcattggta    6360 actgtcagac caagtttact catatatact ttagattgat ttaaaacttc attttttaatt    6420 taaaaggatc taggtgaaga tcctttttga taatctcatg accaaaatcc cttaacgtga    6480
gttttcgttc cactgagcgt cagaccccgt agaaaagatc aaaggatctt cttgagatcc    6540 ttttttctg cgcgtaatct gctgcttgca acaaaaaaa ccaccgctac cagcggtggt    6600
ttgtttgccg gatcaagagc taccaactct ttttccgaag gtaactggct tcagcagagc    6660
gcagatacca aatactgttc ttctagtgta gccgtagtta ggccaccact tcaagaactc    6720
tgtagcaccg cctacatacc tcgctctgct aatcctgtta ccagtggctg ctgccagtgg    6780
cgataagtcg tgtcttaccg ggttggactc aagacgatag ttaccggata aggcgcagcg    6840
gtcgggctga acgggggggtt cgtgcacaca gcccagcttg gagcgaacga cctacaccga    6900
actgagatac ctacagcgtg agctatgaga aagcgccacg cttcccgaag ggagaaaggc    6960
ggacaggtat ccggtaagcg gcagggtcgg aacaggagag cgcacgaggg agcttccagg    7020
gggaaacgcc tggtatcttt atagtcctgt cgggtttcgc cacctctgac ttgagcgtcg    7080
atttttgtga tgctcgtcag ggggcggag cctatggaaa aacgccagca acgcggcctt    7140
tttacggttc ctggccttt gctggccttt tgctcacatg ttctttcctg cgttatcccc    7200
tgattctgtg ataaccgta ttaccgcctt tgagtgagct gataccgctc gccgcagccg    7260
aacgaccgag cgcagcgagt cagtgagcga ggaagcggaa gagcgcccaa tacgcaaacc    7320
gcctctcccc gcgcgttggc cgattcatta atgcagctgg cacgacaggt ttcccgactg    7380
```

```
gaaagcgggc agtgagcgca acgcaattaa tgtgagttag ctcactcatt aggcacccca      7440
ggctttacac tttatgcttc cggctcgtat gttgtgtgga attgtgagcg gataacaatt      7500
tcacacagga aacagctatg accatgatta cgccagattt aattaaggcc ttaattagg       7559

<210> SEQ ID NO 8
<211> LENGTH: 227
<212> TYPE: DNA
<213> ORGANISM: Artificial Sequence
<220> FEATURE:
<223> OTHER INFORMATION: Synthetic

<400> SEQUENCE: 8
gcccgtcagt gggcagagcg cacatcgccc acagtccccg agaagttggg gggagggtc       60 ggcaattgaa ccggtgccta gagaaggtgg cgcggggtaa actgggaaag tgatgtcgtg     120
tactggctcc gccttttcc cgagggtggg ggagaaccgt atataagtgc agtagtcgcc      180
gtgaacgttc tttttcgcaa cgggtttgcc gccagaacac gcgtaag                  227

<210> SEQ ID NO 9
<211> LENGTH: 1278
<212> TYPE: PRT
<213> ORGANISM: Homo sapiens

<400> SEQUENCE: 9
```

| Met | Thr | Ala | Arg | Gly | Leu | Ala | Leu | Gly | Leu | Leu | Leu | Leu | Leu | Cys |
|---|---|---|---|---|---|---|---|---|---|---|---|---|---|---|
| 1 |   |   |   | 5 |   |   |   |   | 10 |   |   |   |   | 15 |

| Pro | Ala | Gln | Val | Phe | Ser | Gln | Ser | Cys | Val | Trp | Tyr | Gly | Glu | Cys | Gly |
|---|---|---|---|---|---|---|---|---|---|---|---|---|---|---|---|
|   |   |   | 20 |   |   |   |   | 25 |   |   |   |   | 30 |   |   |

Ile Ala Tyr Gly Asp Lys Arg Tyr Asn Cys Glu Tyr Ser Gly Pro Pro
           35                  40                  45

Lys Pro Leu Pro Lys Asp Gly Tyr Asp Leu Val Gln Glu Leu Cys Pro
 50                  55                  60

Gly Phe Phe Phe Gly Asn Val Ser Leu Cys Cys Asp Val Arg Gln Leu
 65                  70                  75                  80

Gln Thr Leu Lys Asp Asn Leu Gln Leu Pro Leu Gln Phe Leu Ser Arg
                 85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
            115                 120                 125

Tyr Val Asp Pro Val Thr Asn Gln Thr Lys Thr Asn Val Lys Glu Leu
            130                 135                 140

Gln Tyr Tyr Val Gly Gln Gly Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
            195                 200                 205

Phe Ser Asp Phe Pro Val His Gly Met Glu Pro Met Asn Asn Ala Thr
            210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro
                245                 250                 255

```
Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640

His Ile Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
            660                 665                 670
```

-continued

```
Gly Val Phe Ser Tyr Ile Gly Leu Pro Leu Thr Leu Ile Val Ile Glu
            675                 680                 685

Val Ile Pro Phe Leu Val Leu Ala Val Gly Val Asp Asn Ile Phe Ile
    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
                740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
                820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
    850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
        900                 905                 910

Gly Cys Asn Asn Asp Ser Leu Val Gln Gln Ile Phe Asn Ala Ala Gln
    915                 920                 925

Leu Asp Asn Tyr Thr Arg Ile Gly Phe Ala Pro Ser Ser Trp Ile Asp
930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990

Gly Asp Phe Met Arg Phe Leu Pro Met Phe Leu Ser Asp Asn Pro Asn
        995                 1000                1005

Pro Lys Cys Gly Lys Gly Gly His Ala Ala Tyr Ser Ser Ala Val
    1010                1015                1020

Asn Ile Leu Leu Gly His Gly Thr Arg Val Gly Ala Thr Tyr Phe
    1025                1030                1035

Met Thr Tyr His Thr Val Leu Gln Thr Ser Ala Asp Phe Ile Asp
    1040                1045                1050

Ala Leu Lys Lys Ala Arg Leu Ile Ala Ser Asn Val Thr Glu Thr
    1055                1060                1065

Met Gly Ile Asn Gly Ser Ala Tyr Arg Val Phe Pro Tyr Ser Val
    1070                1075                1080

Phe Tyr Val Phe Tyr Glu Gln Tyr Leu Thr Ile Ile Asp Asp Thr
```

|         |         |         |         |         |         |         |         |         |         |
|---------|---------|---------|---------|---------|---------|---------|---------|---------|---------|
|         |  1085   |         |         |  1090   |         |         |  1095   |         |         |

Ile Phe Asn Leu Gly Val Ser Leu Gly Ala Ile Phe Leu Val Thr
                1100                    1105                    1110

Met Val Leu Leu Gly Cys Glu Leu Trp Ser Ala Val Ile Met Cys
                1115                    1120                    1125

Ala Thr Ile Ala Met Val Leu Val Asn Met Phe Gly Val Met Trp
                1130                    1135                    1140

Leu Trp Gly Ile Ser Leu Asn Ala Val Ser Leu Val Asn Leu Val
                1145                    1150                    1155

Met Ser Cys Gly Ile Ser Val Glu Phe Cys Ser His Ile Thr Arg
                1160                    1165                    1170

Ala Phe Thr Val Ser Met Lys Gly Ser Arg Val Glu Arg Ala Glu
                1175                    1180                    1185

Glu Ala Leu Ala His Met Gly Ser Ser Val Phe Ser Gly Ile Thr
                1190                    1195                    1200

Leu Thr Lys Phe Gly Gly Ile Val Val Leu Ala Phe Ala Lys Ser
                1205                    1210                    1215

Gln Ile Phe Gln Ile Phe Tyr Phe Arg Met Tyr Leu Ala Met Val
                1220                    1225                    1230

Leu Leu Gly Ala Thr His Gly Leu Ile Phe Leu Pro Val Leu Leu
                1235                    1240                    1245

Ser Tyr Ile Gly Pro Ser Val Asn Lys Ala Lys Ser Cys Ala Thr
                1250                    1255                    1260

Glu Glu Arg Tyr Lys Gly Thr Glu Arg Glu Arg Leu Leu Asn Phe
                1265                    1270                    1275

<210> SEQ ID NO 10
<211> LENGTH: 4650
<212> TYPE: DNA
<213> ORGANISM: Homo sapiens

<400> SEQUENCE: 10

| | | |
|---|---|---|
| gctcggggtg ctgaaacagc ccggggaagt agagccgcct ccggggagcc caaccagccg | 60 |
| aacgccgccg gcgtcagcag ccttgcgcgg ccacagcatg accgctcgcg gcctggccct | 120 |
| tggcctcctc ctgctgctac tgtgtccagc gcaggtgttt tcacagtcct gtgtttggta | 180 |
| tggagagtgt ggaattgcat atggggacaa gaggtacaat tgcgaatatt ctggcccacc | 240 |
| aaaaccattg ccaaaggatg gatatgactt agtgcaggaa ctctgtccag gattcttctt | 300 |
| tggcaatgtc agtctctgtt gtgatgttcg gcagcttcag acactaaaag acaacctgca | 360 |
| gctgcctcta cagtttctgt ccagatgtcc atcctgtttt tataacctac tgaacctgtt | 420 |
| ttgtgagctg acatgtagcc ctcgacagag tcagttttg aatgttacag ctactgaaga | 480 |
| ttacgttgat cctgttacaa accagacgaa acaaatgtg aaagagttac aatactacgt | 540 |
| cggacagggt tttgccaatg caatgtacaa tgcctgccgg gatgtggagg cccctcaag | 600 |
| taatgacaag gccctgggac tcctgtgtgg aaggacgct gacgcctgta atgccaccaa | 660 |
| ctggattgaa tacatgttca ataaggacaa tggacaggca ccttttacca tcactcctgt | 720 |
| gttttcagat tttccagtcc atgggatgga gcccatgaac aatgccacca aaggctgtga | 780 |
| cgagtctgtg gatgaggtca gcagccatg tagctgccaa gactgctcta ttgtctgtgg | 840 |
| ccccaagccc cagccccac ctcctcctgc tccctggacg atccttggct tggacgccat | 900 |
| gtatgtcatc atgtgtgatca cctacatggc gtttttgctt gtgtttttg gagcattttt | 960 |
| tgcagtgtgg tgctacagaa aacggtattt tgtctccgag tacactccca tcgatagcaa | 1020 |

| | |
|---|---|
| tatagctttt tctgttaatg caagtgacaa aggagaggcg tcctgctgtg accctgtcag | 1080 |
| cgcagcattt gagggctgct tgaggcggct gttcacacgc tggggtcttt tctgcgtccg | 1140 |
| aaaccctggc tgtgtcattt tcttctcgct ggtcttcatt actgcgtgtt cgtcaggcct | 1200 |
| ggtgtttgtc cgggtcacaa ccaatccagt tgacctctgg tcagccccca gcagccaggc | 1260 |
| tcgcctggaa aaagagtact ttgaccagca ctttgggcct ttcttccgga cggagcagct | 1320 |
| catcatccgg ccccctctca ctgacaaaca catttaccag ccatacccett cgggagctga | 1380 |
| tgtacccttt ggacctccgc ttgacataca gatactgcac caggttcttg acttacaaat | 1440 |
| agccatcgaa acattactg cctcttatga caatgagact gtgacacttc aagacatctg | 1500 |
| cttggcccct ctttcaccgt ataacacgaa ctgcaccatt ttgagtgtgt taaattactt | 1560 |
| ccagaacagc cattccgtgc tggaccacaa gaaaggggac gacttctttg tgtatgccga | 1620 |
| ttaccacacg cactttctgt actgcgtacg ggctcctgcc tctctgaatg atacaagttt | 1680 |
| gctccatgac cctgtctgg gtacgtttgg tggaccagtg ttcccgtggc ttgtgttggg | 1740 |
| aggctatgat gatcaaaact acaataacgc cactgcccett gtgattaccct tccctgtcaa | 1800 |
| taattactat aatgatacag agaagctcca gagggcccag gctgggaaaa agagtttat | 1860 |
| taattttgtg aaaaactaca gaatcccaa tctgaccatt tccttcactg ctgaacgaag | 1920 |
| tattgaagat gaactaaatc gtgaaagtga cagtgatgtc ttcaccgttg taattagcta | 1980 |
| tgccatcatg tttctatata tttccctagc cttggggcac atcaaaagct gtcgcaggct | 2040 |
| tctggtggat tcgaaggtct cactaggcat cgcgggcatc ttgatcgtgc tgagctcggt | 2100 |
| ggcttgctcc ttgggtgtct tcagctacat tgggttgccc ttgaccctca ttgtgattga | 2160 |
| agtcatcccg ttcctggtgc tggctgttgg agtggacaac atcttcattc tggtgcaggc | 2220 |
| ctaccagaga gatgaacgtc ttcaagggga aaccctggat cagcagctgg gcagggtcct | 2280 |
| aggagaagtg gctcccagta tgttcctgtc atccttttct gagactgtag cattttctt | 2340 |
| aggagcattg tccgtgatgc cagccgtgca caccttctct ctctttgcgg gattggcagt | 2400 |
| cttcattgac tttcttctgc agattacctg tttcgtgagt ctcttggggt tagacattaa | 2460 |
| acgtcaagag aaaaatcggc tagacatctt ttgctgtgtc agaggtgctg aagatggaac | 2520 |
| aagcgtccag gcctcagaga ctgtttgtt tcgcttcttc aaaaactcct attctccact | 2580 |
| tctgctaaag gactggatga gaccaattgt gatagcaata tttgtgggtg ttctgtcatt | 2640 |
| cagcatcgca gtcctgaaca agtagatat tggattggat cagtctcttt cgatgccaga | 2700 |
| tgactcctac atggtggatt atttcaaatc catcagtcag tacctgcatg cgggtccgcc | 2760 |
| tgtgtacttt gtcctggagg aagggcacga ctacacttct tccaaggggc agaacatggt | 2820 |
| gtgcggcggc atgggctgca acaatgattc cctggtgcag cagatattta acgcggcgca | 2880 |
| gctggacaac tacccgaa taggcttcgc ccctcgtcc tggatcgacg attattcga | 2940 |
| ctgggtgaag ccacagtcgt cttgctgtcg agtggacaat atcactgacc agttctgcaa | 3000 |
| tgcttcagtg gttgaccctg cctgcgttcg ctgcaggcct ctgactccgg aaggcaaaca | 3060 |
| gaggcctcag gggggagact tcatgagatt cctgcccatg ttcctttcgg ataaccctaa | 3120 |
| cccaagtgt ggcaaagggg gacatgctgc ctatagttct gcagttaaca tcctccttgg | 3180 |
| ccatggcacc agggtcggag ccacgtactt catgacctac cacaccgtgc tgcagacctc | 3240 |
| tgctgacttt attgacgctc tgaagaaagc ccgacttata gccagtaatg tcaccgaaac | 3300 |
| catgggcatt aacggcagtg cctaccgagt atttccttac agtgtgttt atgtcttcta | 3360 |

```
cgaacagtac ctgaccatca ttgacgacac tatcttcaac ctcggtgtgt ccctgggcgc    3420
gatatttctg gtgaccatgg tcctcctggg ctgtgagctc tggtctgcag tcatcatgtg    3480
tgccaccatc gccatggtct tggtcaacat gtttggagtt atgtggctct ggggcatcag    3540
tctgaacgct gtatccttgg tcaacctggt gatgagctgt ggcatctccg tggagttctg    3600
cagccacata accagagcgt tcacggtgag catgaaaggc agccgcgtgg agcgcgcgga    3660
agaggcactt gcccacatgg gcagctccgt gttcagtgga atcacactta caaaatttgg    3720
agggattgtg gtgttggctt tgccaaatc tcaaattttc cagatattct acttcaggat    3780
gtatttggcc atggtcttac tgggagccac tcacggatta atatttctcc ctgtcttact    3840
cagttacata gggccatcag taaataaagc caaaagttgt gccactgaag agcgatacaa    3900
aggaacagag cgcgaacggc ttctaaattt ctagccctct cgcagggcat cctgactgaa    3960
ctgtgtctaa gggtcggtcg gtttaccact ggacgggtgc tgcatcggca aggccaagtt    4020
gaacaccgga tggtgccaac catcggttgt ttggcagcag ctttgaacgt agcgcctgtg    4080
aactcaggaa tgcacagttg acttgggaag cagtattact agatctggag caaccacag    4140
gacactaaac ttctcccagc ctcttcagga agaaacctc attctttggc aagcaggagg    4200
tgacactaga tggctgtgaa tgtgatccgc tcactgacac tctgtaaagg ccaatcaatg    4260
cactgtctgt ctctcctttt aggagtaagc catcccacaa gttctatacc atatttttag    4320
tgacagttga gtttgtagat acactttata acatttata gttaaagag ctttattaat    4380
gcaataaatt aactttgtac acattttat ataaaaaaac agcaagtgat ttcagaatgt    4440
tgtaggcctc attagagctt ggtctccaaa aatctgtttg aaaaaagcaa catgttcttc    4500
acagtgttcc cctagaaagg aagagattta attgccagtt agatgtggca tgaaatgagg    4560
gacaaagaaa gcatctcgta ggtgtgtcta ctgggttta acttatttt ctttaataaa    4620
atacattgtt ttcctaaaaa aaaaaaaaa    4650
```

<210> SEQ ID NO 11
<211> LENGTH: 151
<212> TYPE: PRT
<213> ORGANISM: Homo sapiens

<400> SEQUENCE: 11

```
Met Arg Phe Leu Ala Ala Thr Phe Leu Leu Ala Leu Ser Thr Ala
1               5                   10                  15

Ala Gln Ala Glu Pro Val Gln Phe Lys Asp Cys Gly Ser Val Asp Gly
            20                  25                  30

Val Ile Lys Glu Val Asn Val Ser Pro Cys Pro Thr Gln Pro Cys Gln
        35                  40                  45

Leu Ser Lys Gly Gln Ser Tyr Ser Val Asn Val Thr Phe Thr Ser Asn
    50                  55                  60

Ile Gln Ser Lys Ser Ser Lys Ala Val Val His Gly Ile Leu Met Gly
65                  70                  75                  80

Val Pro Val Pro Phe Pro Ile Pro Glu Pro Asp Gly Cys Lys Ser Gly
                85                  90                  95

Ile Asn Cys Pro Ile Gln Lys Asp Lys Thr Tyr Ser Tyr Leu Asn Lys
            100                 105                 110

Leu Pro Val Lys Ser Glu Tyr Pro Ser Ile Lys Leu Val Val Glu Trp
        115                 120                 125

Gln Leu Gln Asp Asp Lys Asn Gln Ser Leu Phe Cys Trp Glu Ile Pro
    130                 135                 140
```

-continued

```
Val Gln Ile Val Ser His Leu
145                 150

<210> SEQ ID NO 12
<211> LENGTH: 920
<212> TYPE: DNA
<213> ORGANISM: Homo sapiens

<400> SEQUENCE: 12
acaggtcgcc tgactgggct cctccccggg cccgccccga caggtttgtc ttgtgaccgc      60
gggcggccgc tgcttctttc ccgagcttgg aacttcgtta tccgcgatgc gtttcctggc     120
agctacattc ctgctcctgg cgctcagcac cgctgcccag gccgaaccgg tgcagttcaa     180
ggactgcggt tctgtggatg gagttataaa ggaagtgaat gtgagcccat gccccaccca     240
accctgccag ctgagcaaag gacagtctta cagcgtcaat gtcaccttca ccagcaatat     300
tcagtctaaa agcagcaagg ccgtggtgca tggcatcctg atgggcgtcc cagttccctt     360
tcccattcct gagcctgatg gttgtaagag tggaattaac tgccctatcc aaaaagacaa     420
gacctatagc tacctgaata aactaccagt gaaaagcgaa tatccctcta taaaactggt     480
ggtggagtgg caacttcagg atgacaaaaa ccaaagtctc ttctgctggg aaatcccagt     540
acagatcgtt tctcatctct aagtgcctca ttgagttcgg tgcatctggc caatgagtct     600
gctgagactc ttgacagcac ctccagctct gctgcttcaa caacagtgac ttgctctcca     660
atggtatcca gtgattcgtt gaagaggagg tgctctgtag cagaaactga gctccgggtg     720
gctggttctc agtggttgtc tcatgtctct ttttctgtct taggtggttt cattaaatgc     780
agcacttggt tagcagatgt ttaattttt ttttaacaac attaacttgt ggcctctttc     840
tacacctgga aatttactct tgaataaata aaaactcgtt tgtcttgtca aaaaaaaaa     900 aaaaaaaaaa aaaaaaaaa                                                  920
```

VIRAL GENE THERAPY AS TREATMENT FOR CHOLESTEROL STORAGE DISEASE OR DISORDER

CROSS REFERENCE TO RELATED APPLICATIONS

This patent application is a divisional of U.S. patent application Ser. No. 15/565,065, filed Oct. 6, 2017, which is the U.S. National Stage of PCT/US2016/026524, filed Apr. 7, 2016, which claims the benefit of U.S. Provisional Patent Application No. 62/144,702, filed Apr. 8, 2015, and entitled VIRAL GENE THERAPY AS TREATMENT FOR CHOLESTEROL STORAGE DISEASE OR DISORDER, each of which is incorporated herein by reference in its entirety.

GOVERNMENT FUNDING

This invention was made with Government support under project numbers ZIA HG000068 13 and ZIA HG200318 13 by the National Institutes of Health, National Human Genome Research Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 47,383 Byte ASCII (Text) file named "750170_ST25.txt," dated Aug. 5, 2020.

BACKGROUND OF THE INVENTION

Niemann-Pick disease, type C (NPC) is a rare and fatal, autosomal recessive, neurodegenerative disease that can present in infants, children, or adults. Its incidence in persons of Western European descent is 1/90,000 (Wassif C A et al., "High incidence of unrecognized visceral/neurological late-onset Niemann-Pick disease, type C1, predicted by analysis of massively parallel sequencing data sets," Genet Med. 2015 Mar. 12). Approximately 95% of patients with NPC have mutations in NPC1, a gene implicated in intracellular cholesterol trafficking. Mutation of NPC1 causes intracellular accumulation of unesterified cholesterol in late endosomal/lysosomal structures and marked accumulation of glycosphingolipids, especially in neuronal tissue. Thus, NPC patients generally present with hepatosplenomegaly (enlargement of liver and spleen) and neurological degeneration.

A prenatal syndrome of nonimmune fetal hydrops can be the first symptom of NPC disease. Neonates can present with severe liver disease from infiltration of the liver and/or respiratory failure. Other infants, without liver or pulmonary disease, have hypotonia and developmental delay. The classic presentation occurs in mid-to-late childhood with the insidious onset of ataxia, vertical supranuclear gaze palsy (VSGP), and dementia. Regression is common. Seizures are frequent and neurological symptoms become disabling, making oral feeding impossible; death usually occurs in the late second or third decade from aspiration pneumonia. Adults can be more mildly affected and are more likely to present with dementia or psychiatric symptoms. There are no proven treatments for NPC, and after the diagnosis, fatal neurodegeneration is inevitable. The fact that most patients have disease onset in childhood makes the search for effective therapies urgent.

The diagnosis of NPC disease is confirmed by specialized biochemical testing that demonstrates cholesterol storage and is detected by filipin staining in cultured fibroblasts. Most individuals with NPC disease have NPC type 1, caused by mutations in NPC1; fewer than 20 individuals have been diagnosed with NPC type 2, caused by mutations in NPC2. Molecular genetic testing of NPC1 and NPC2 detects disease-causing mutations in approximately 94% of individuals with NPC disease, almost all of whom have mutations in NPC1. NPC disease, regardless of the locus and allele(s), is a recessive metabolic condition and the mutations are loss of function or reduced function. Therefore providing and expressing a single copy of the wild type gene can completely restore NPC1 or 2 enzymatic function.

A series of landmark studies conducted by the research group of Dr. William Pavan of the NHGRI/NIH led to the identification of both the mouse and human genes for NPC1 (Loftus et al. *Science* 277: 232-35; Carstea et al. *Science* 277: 228-31). A murine model of NPC, $Npc^{nih}$ (also called BALB/cNctr-Npc1$^{m1N}$/J), arising from a spontaneous frame-shift mutation in the Npc1 gene has been described and extensively characterized during these research efforts (Loftus et al. *Science* 277: 232-35). $Npc^{nih}$ homozygotes have an early, severe, and rapidly progressing disease, which is characterized by weight loss, ataxia, and lethality by 9 weeks of age. The mutation carried by this mouse is a null, and $Npc^{nih}$ homozygous mice fail to make Npc1 protein or mRNA. This animal model also displays neurological symptoms and early lethality: $Npc^{nih}$ homozygous mice uniformly begin losing weight by 6 weeks of age and do not survive past 9 weeks. Thus, these animals represent an ideal model of human NPC disease caused by loss of function mutations in the gene NPC1.

Over the years, other mouse models of NPC disease, specifically caused by varied natural or engineered mutations in the mouse Npc1 gene, have been generated but display less severe of a disease phenotype. All mouse models of NPC disease caused by mutation or other malfunction of the Npc1 gene in any mouse strain are treatable by the vector and derivatives described herein and are encompassed in said claims. Such models, as a group including $Npc^{nih}$ homozygous animals, are generally considered $Npc^{-/-}$ designating homozygous Npc loss-of-function alleles, of which $Npc^{nih}$ is paradigmatic.

Notwithstanding the development of such mouse models, no curative therapy for NPC yet exists. A strategy or methodology for clinically treating NPC and/or providing a curative therapy for NPC and/or its symptoms is urgently needed in the art. The present invention fulfills such a need.

SUMMARY OF THE INVENTION

The present invention provides, for the first time, gene therapy constructs comprising a therapeutic human nucleic acid molecule which is able to correct the cellular defect characteristic of certain cholesterol storage diseases or disorders, such as, Niemann-Pick type C disease ("NPC"), when the therapeutic human nucleic acid molecule is under control of a tissue-specific promoter, including, in certain embodiments, a neuronal-specific calcium/calmodulin-dependent protein kinase II (CaMKII) promoter or one broadly expressed, such as the elongation factor 1 alpha (EF1α) constitutive promoter or a derivative thereof. The inventors contemplate use of these vector constructs for gene therapy of certain cholesterol storage diseases or disorders, including NPC. Examples are provided which demonstrate the reduction of practice and the effectiveness of the present invention in the most established and well-characterized animal model of NPC.

More in particular, the invention provides compositions and methods for treating or preventing cholesterol storage diseases or disorders. In certain aspects, the present invention provides compositions and methods for treating or preventing Niemann-Pick disease, type C. In certain embodiments, the invention relates to compositions and methods for treating or preventing cholesterol storage diseases or disorders that are characterized by or associated with a risk of diminution of central nervous system (CNS) function, including NPC. In still other embodiments, the present invention relates to nucleic acid molecules encoding therapeutic transgenes, e.g., NPC1 or NPC2, which are capable of restoring the function lost to one or more defective genes or polypeptide products thereof, e.g., a mutant NPC1 or NPC2 gene. In yet other embodiments, the invention relates to pharmaceutical compositions that are suitable for administering therapeutically effective amounts the nucleic acid molecules of the invention. In still further embodiments, the present invention relates to methods for diagnosing NPC and/or monitoring the progress of gene therapy treatment of NPC by monitoring the expression and/or function of a therapeutic gene, e.g., NPC1 or NPC2.

The present invention, in still other embodiments, relates to methods of gene therapy involving administering in an effective amount a nucleic acid molecule comprising a therapeutic transgene, e.g., NPC1 or NPC2, in order to treat or prevent a cholesterol storage disease or disorder, including NPC. In still other embodiments, the present invention relates to methods of gene therapy involving administering, in an effective amount, an expression vector encoding NPC1 or NPC2 in order to treat or prevent a cholesterol storage disease or disorder, including NPC disease. In yet other embodiments, the nucleic acid molecule and/or expression vector may be selectively delivered to a target site or tissue, e.g., the central nervous system.

The nucleic acid molecules or gene therapy constructs in certain embodiments comprising one or more therapeutic transgenes, e.g., NPC1 or NPC2, which are under the control of at least one genetic regulatory element, such as a promoter. In certain embodiments, the promoter is a tissue-specific promoter that is capable of being expressed in the CNS. In some embodiments, the promoter is a neuronal-specific calmodulin promoter. In other embodiments, the promoter is an EF1α ("human elongation factor 1 alpha") constitutive promoter. In other embodiments the promoter is a novel, truncated variant of the EF1α ($_{miniEF1\alpha}$).

The present invention also relates to specific nucleic acid molecules comprising a therapeutic transgene, e.g., NPC1 or NPC2, under transcriptional control of a promoter that is capable of being expressed in the CNS, including a neuronal-specific calmodulin promoter or a $_{miniEF1\alpha}$ constitutive promoter. The invention also contemplates that such nucleic acid constructs may be engineered into any suitable gene therapy vector, such as a retrovirus, lentivirus adenovirus or adeno-associated virus (AAV) vector, nucleic acid such as plasmid DNA, peptide nucleic acids, or mRNA, including mRNAs that are contain modified bases to enhance in vivo expression. All forms of nucleic acids can be delivered without further modification, such as naked DNA, or packaged into nanoparticles or lipid nanoparticles and delivered in an appropriate fashion to produce NPC1 or 2 expression. In a particular embodiment, the background gene therapy vector is an AAV.

Through the manipulation of the nucleotide sequences provided by this invention by standard molecular biology techniques, variants of the NPC1 and NPC2 proteins may be made which differ in precise amino acid sequence from the disclosed proteins yet which maintain the basic functional characteristics of the disclosed NPC1 and NPC2 proteins or which are selected to differ in some characteristics from these proteins. Such variants are another aspect of the present invention as they may also be administered using the gene therapy vectors and tissue-specific promoters (e.g., neuronal-specific CaMKII or $_{mini}$CaMKII promoter) or constitutive promoters (e.g., EF1α or $_{miniEF1\alpha}$) of the invention.

In another embodiment, the vectors described here may be modified to encode versions of the NPC1 and NPC2 proteins that have been codon-optimized for expression in a test subject, such as a mouse or cat or human, or for use in patients with NPC disease.

The foregoing and other features and advantages of the invention will become more apparent from the following detailed description and accompanying drawings. Those skilled in the art will appreciate that the utility of this invention is not limited to the specific experimental modes and materials described herein.

In a preferred embodiment, the present invention is directed to a nucleic acid construct comprising: (1) a viral vector sequence; and (2) an NPC1 gene sequence under control of a mini-calmodulin promoter or a mini-elongation factor 1α ($_{shortminiEF1\alpha}$) promoter.

The viral vector can be an adeno-associated viral (AAV) vector.

The nucleic acid construct can comprise a sequence selected from the group consisting of SEQ ID NO: 1 and SEQ ID NO: 7.

The nucleic acid construct can be used to treat or prevent a cholesterol storage disease or disorder in a subject, said method comprising: administering a nucleic acid construct of any one of the preceding claims and a pharmaceutically acceptable viral carrier to a subject, thereby treating or preventing the cholesterol storage disease or disorder in said subject.

The cholesterol storage disease or disorder can be Niemann-Pick disease, Type C.

The subject can be a mouse or other animal, e.g., an experimental animal. The animal can be a Npc1 knockout mouse.

The subject can also be a human, who has or is at risk of having NPC.

The nucleic acid construct can be encapsidated with an AAV serotype 9 capsid.

The concentration of the nucleic acid construct in the viral carrier-nucleic acid construct composition can be $5 \times 10^{12}$ gc/ml or greater ("genome copy" per ml).

The pharmaceutically acceptable viral carrier can be AAV.

The AAV can be selected from the group consisting of AAV2, AAV3, AAV4, AAV5, AAV6, AAV7, AAV8, AAV9, AAV rh8, AAVrh10, AAVrh33, AAV rh34, AAV Anc80, or AAV PHP.B.

The pharmaceutically acceptable viral carrier can comprise a viral capsid selected from the group consisting of AAV2, AAV3, AAV4, AAV5, AAV6, AAV7, AAV8, AAV9, AAV rh8, AAVrh10, AAVrh33, AAV rh34, AAV Anc80 or AAV PHP.B viral capsid.

In another aspect, the invention relates to a method for treating Neimann-Pick disease, Type C in a subject by gene therapy comprising administering a composition comprising a therapeutically effective amount of gene therapy construct comprising (1) a viral vector sequence; and (2) an NPC1 gene sequence under control of a mini-calmodulin promoter or a mini-elongation factor 1α ($_{mini}$EF1α) promoter, and a pharmaceutically acceptable carrier.

The viral vector can be an adeno-associated viral (AAV) vector.

The gene therapy construct can comprise a sequence selected from the group consisting of SEQ ID NO: 1 (AAV.$_{mini}$CaMKII NPC1.RBG) and SEQ ID NO: 7 (pAAV-$_{mini}$EF1α-NPC1-RB G).

The subject can be a mouse or other animal, e.g., an experimental animal. The animal can be an Npc1 knockout mouse.

The subject can also be a human, who has or is at risk of having NPC.

The gene therapy construct can be encapsidated with an AAV serotype 9 capsid.

The composition can comprise the gene therapy construct at a concentration of $5 \times 10^{12}$ gc/ml or greater.

The viral vector sequence can be AAV, which can be selected from the group consisting of AAV2, AAV3, AAV4, AAV5, AAV6, AAV7, AAV8, AAV9, AAV rh8, AAVrh10, AAVrh33, AAV rh34, AAV Anc80 or AAV PHP.B.

The gene therapy construct can comprise a viral capsid selected from the group consisting of AAV2, AAV3, AAV4, AAV5, AAV6, AAV7, AAV8, AAV9, AAV rh8, AAVrh10, AAVrh33, AAV rh34, AAV Anc80 or AAV PHP.B viral capsid.

Other aspects of the invention are described in, or are obvious from, the following disclosure, and are within the ambit of the invention.

BRIEF DESCRIPTION OF THE DRAWINGS

The following detailed description, given by way of example, but not intended to limit the invention solely to the specific embodiments described, may best be understood in conjunction with the accompanying drawings. Reference will now be made, by way of example, to the accompanying drawings which show example embodiments of the present application.

SEQUENCE LISTING

Figure 1:
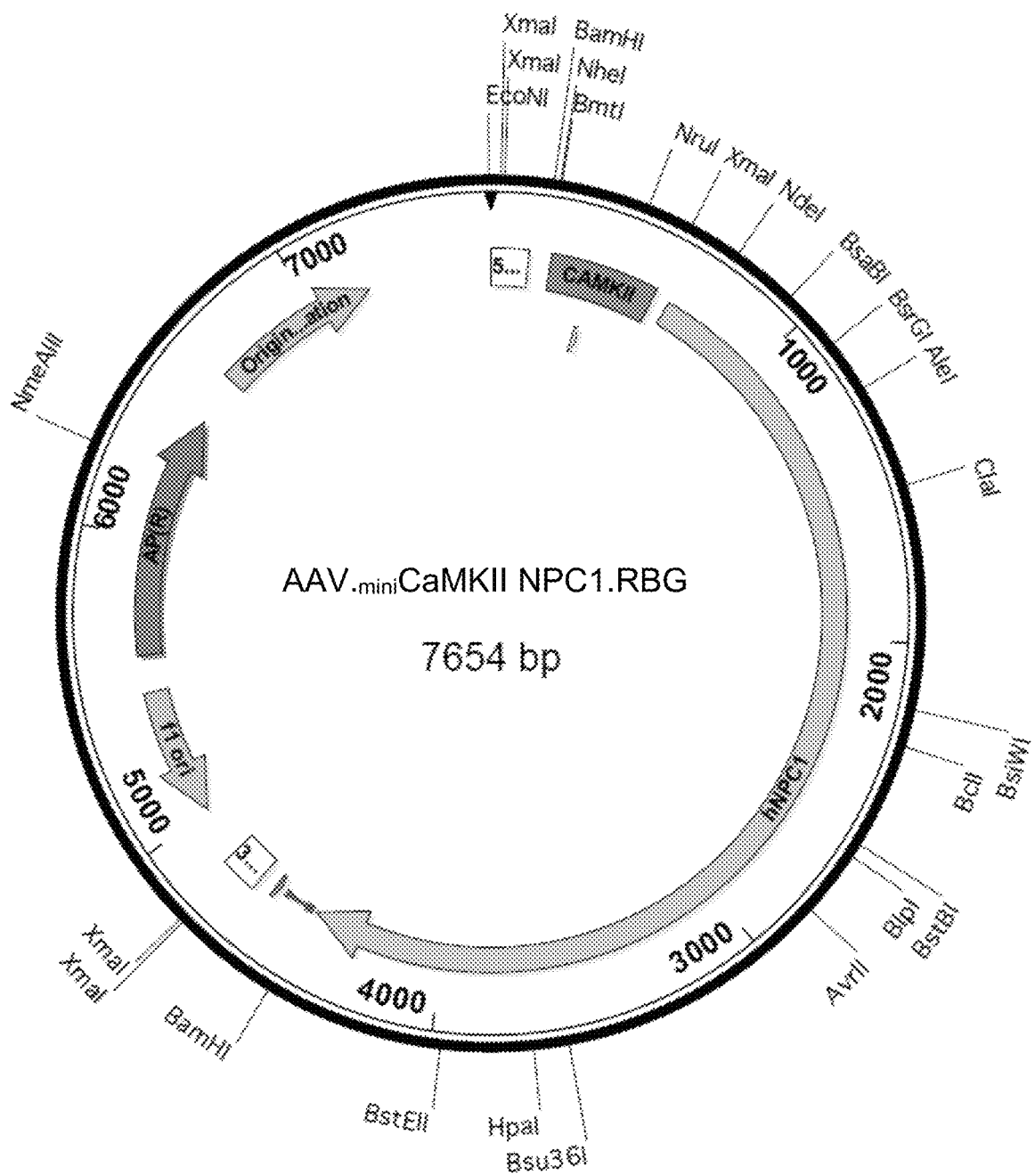
FIG. 1 shows a map of the $_{mini}$calmodulin-NPC plasmid (pAAV.$_{mini}$CaMKII NPC1.RBG) as disclosed herein for AAV-mediated delivery in AAV-$_{mini}$calmodulin-NPC.
Figure 2:
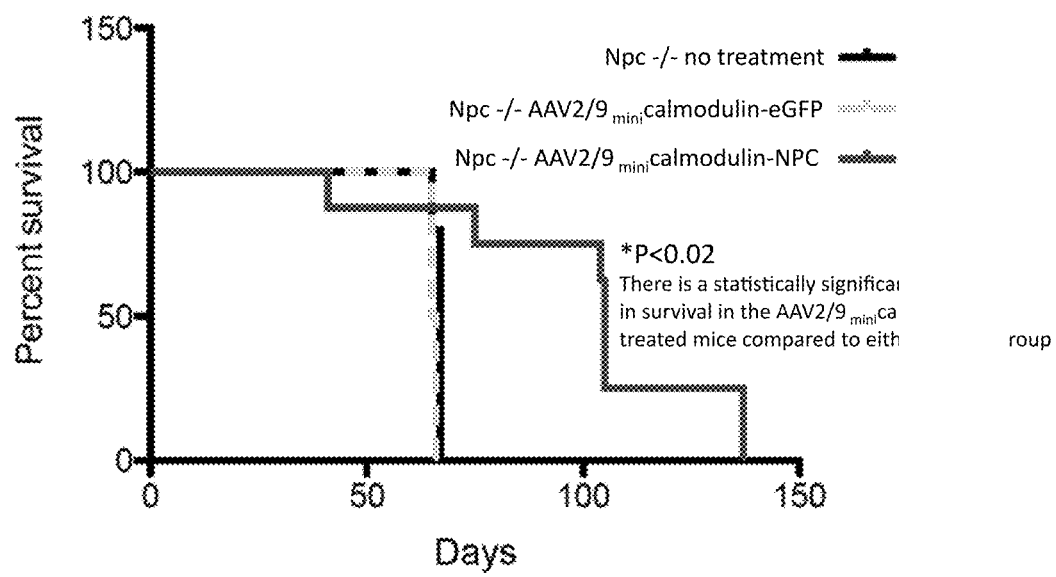
FIG. 2 shows survival in Npc$^{nih}$ homozygous mice (n=10) after no treatment (black hatched lines), treatment with a AAV2/9.$_{mini}$CaMKII eGFP.RBG reporter vector (n=6) or treatment with AAV2/9.$_{mini}$CaMKII NPC1.RBG (n=9).
Figure 3:
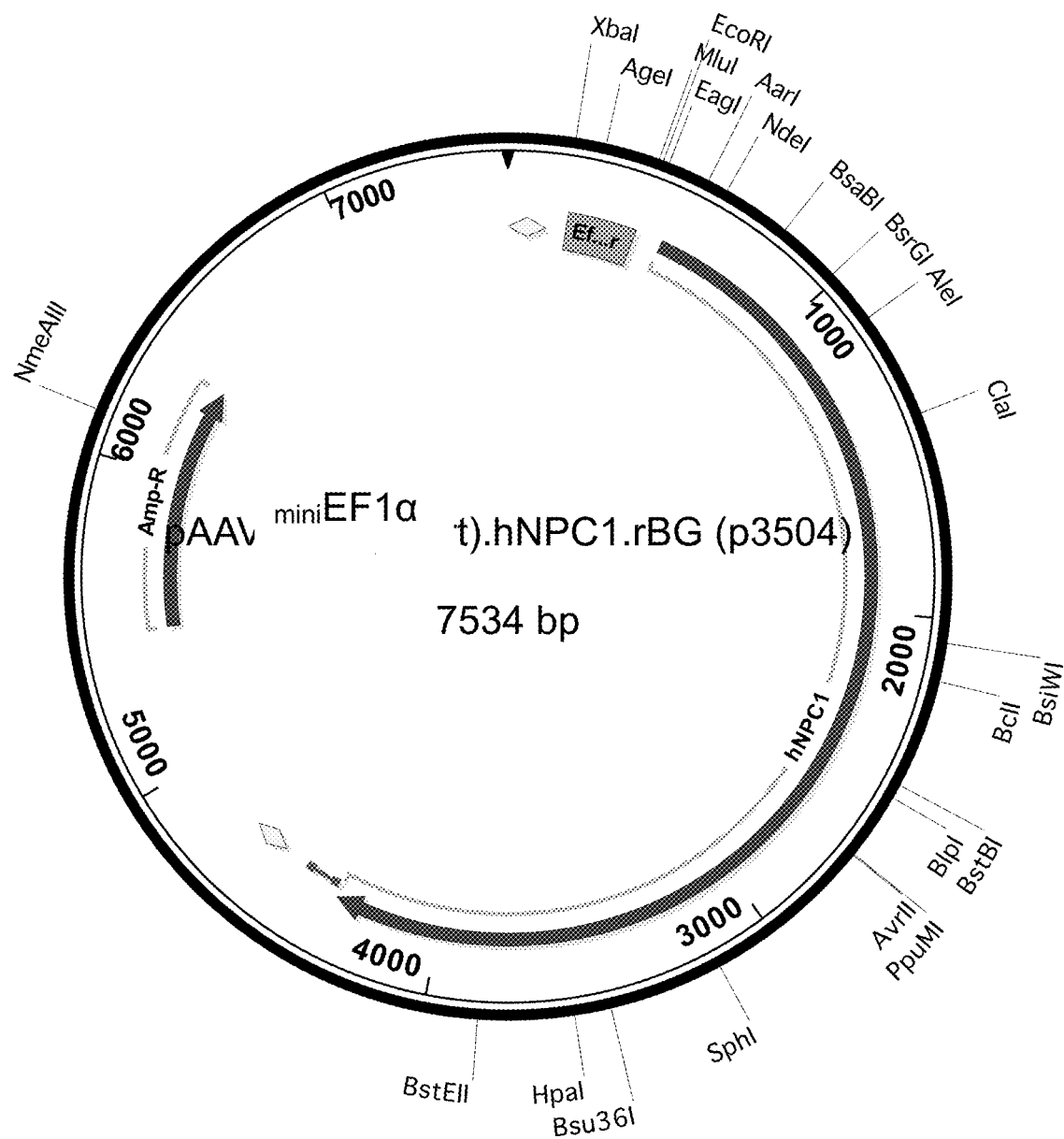
FIG. 3. Map of AAV-$_{mini}$EF1α-NPC1 showing important vector elements. The full length EF1α promoter was truncated and tested for the ability to drive eGFP expression in a transfection experiment using 293T cells (not presented). The promoter fragment was then introduced into an AAV vector in front of the full length human NPC1 cDNA, followed a rabbit beta globin poly A signal, and flanked by AAV2 inverted terminal repeats (ITR). The resulting vector was packaged into an AAV using a serotype 9 capsid to create AAV2/9-$_{mini}$EF1α-NPC1 or AAV9-$_{mini}$EF1α-NPC1.

The specification includes a Sequence Listing appended herewith which includes sequences, as follows:
SEQ ID NO: 1: Nucleotide sequence of AAV.$_{mini}$CaMKII NPC1.RBG; SEQ ID NO: 2: Nucleotide sequence of the 5' inverted terminal repeat (5' ITR) of AAV.$_{mini}$CaMKII NPC1.RBG;
SEQ ID NO: 3: Nucleotide sequence of the CaMKII promoter ($_{mini}$calmodulin promoter) of AAV.$_{mini}$CaMKII NPC1.RBG;
SEQ ID NO: 4: Nucleotide sequence of the hNPC1 cDNA of AAV.$_{mini}$CaMKII NPC1.RBG;
SEQ ID NO: 5: Nucleotide sequence of the rabbit globin polyA of AAV.$_{mini}$CaMKII NPC1.RBG;
SEQ ID NO: 6: Nucleotide sequence of the 3' inverted terminal repeat (3' ITR) of AAV.$_{mini}$CaMKII NPC1.RBG;
SEQ ID NO: 7: Nucleotide sequence of AAV$_{mini}$EF1α-NPC;
SEQ ID NO: 8: Nucleotide sequence of the EF1α promoter of AAV2/9-$_{mini}$EF1α-NPC;
SEQ ID NO: 9: NPC1 amino acid sequence;
SEQ ID NO: 10: NPC1 cDNA nucleotide sequence;
SEQ ID NO: 11: NPC2 amino acid sequence; and
SEQ ID NO: 12: NPC2 cDNA nucleotide sequence.

DETAILED DESCRIPTION OF THE INVENTION

The present invention is directed, at least in part, to compositions and methods for treating or preventing cholesterol storage diseases or disorders, such as Niemann-Pick disease, type C caused by mutation or malfunction of the NPC1 and/or NPC2 enzymes, which are encoded by the NPC1 and NPC2 genes, respectively. In certain aspects, compositions of the instant invention include one or more gene therapy constructs comprising NPC1 and/or NPC2 genes, or derivatives and/or mutants thereof, which are operably linked to at least a promoter element that is capable of being expressed in a tissue of the central nervous system. In certain embodiments, the promoter is a neuronal-specific calmodulin promoter. In other embodiments, the promoter is a constitutive promoter, e.g., an EF1α or $_{mini}$EF1α constitutive promoter, which is capable of being expressed in neuronal as well as other tissues. As demonstrated by a reduction to practice using accepted NPC mouse models, the gene therapy vectors of the present invention were effective in treating and/or preventing NPC.

In order to facilitate review of the various embodiments of the invention, the following definitions of terms and explanations of abbreviations are provided, as follows:

Definitions

The instant invention provides for the therapeutic or prophylactic use of gene therapy vectors to achieve treatment of subjects having or at risk of developing a cholesterol storage disease or disorder. In certain embodiments, the invention provides compositions and methods for treating or preventing Niemann-Pick disease, type C1, either by delivery of the vector to the CNS in a targeted manner, or systemically, using recombinant AAV viral vectors (e.g., AAV9 viral vectors) to achieve effective transgene delivery in a subject and/or the cells of a subject. In related embodiments, the transgene is NPC1 or functional variant or fragment thereof. In other embodiments, the transgene is NPC2 or functional variant or fragment thereof.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

General Terms

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The term "obtaining" is understood herein as manufacturing, purchasing, or otherwise coming into possession of.

As used herein, "kits" are understood to contain at least the non-standard laboratory reagents of the invention and one or more non-standard laboratory reagents for use in the methods of the invention.

The terms "about" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Terms Relating to NPC

The term Niemann-Pick disease, Type C or abbreviated as "NPC," refers to the disorder as it is known in the medical art, and is distinct from Type A or B. NPC patients are not able to metabolize cholesterol and other lipids properly within the cell. Consequently, excessive amounts of cholesterol accumulate within the liver and spleen and excessive amounts of other lipids accumulate in the brain. NPC causes a secondary reduction of ASM (acid sphingomyelinase) activity such as is characteristic of Type A and B. Type C Niemann-Pick disease has an estimated 500 cases diagnosed worldwide. It is believed, however, that the number of people affected by NPC is higher, but diagnostic difficulties do not allow an accurate assessment of the occurrence rate. NPC has been initially diagnosed as a learning disability, mild retardation, "clumsiness," and delayed development of fine motor skills. It is not uncommon for a family to spend several years seeking a diagnosis before NPC is identified. NPC is always fatal. The majority of children with NPC die before age 20 (many die before the age of 10). Late onset of symptoms can lead to longer life spans but it is extremely rare for any person with NPC to reach age 40. A recent study based on genomic analyses suggests the incidence of infantile onset NPC is 1:90,000 but when all forms are considered, including the adult onset variants, the disease may be as common as 1/19,000-1/36,00. There is currently no curative therapy for any form of NPC disease.

The term "NPC1" refers to the wildtype NPC1 gene or protein, various mutant forms of which are associated with Neimann-Pick Type C disease by leading to the accumulation of intracellular unesterified cholesterol. For convenience, the human gene is referred to as hNPC1 or NPC1 and the murine gene as mNPC1 or Npc1 (this same nomenclature is also used to distinguish between the human and murine cDNAs and proteins). Where no "h" or "m" designation is given, reference to the human NPC1 gene generally is intended. The definition of an NPC1 gene includes the various sequence polymorphisms that exist in the species in question, i.e., the term "hNPC1" or a wildtype hNPC1 encompasses all various sequence polymorphisms in humans.

The NPC1 protein or a derivative may be functionally characterized by its ability, when expressed in NPC cells, to correct the lysosomal cholesterol accumulation phenotype that is characteristic of such cells. Thus, "NPC1 protein biological activity" refers to the ability of a protein to correct the lysosomal cholesterol accumulation phenotype that is characteristic of NPC cells.

A "wildtype NPC1 protein" refers to any protein encoded by a wild-type gene that is capable of having normal (level of function absent disease or disorder) biological activity when expressed or introduced in vivo. Such functionality can be tested by any means known to establish functionality of a protein.

The term "NPC1 derivative gene," which can include a "mutant NPC1 gene," refers to any non-wildtype NPC1 sequence. Typically, a "mutant NPC1 gene" refers to a non-wildtype sequence that results in an aberrant functioning NPC1 protein, and thus, NPC disease. However, the term "NPC1 derivative gene" is meant to be broad enough to encompass an NPC1 mutant gene, but also any other NPC1 gene carrying a genetic change that may result an NPC1 protein having any of an increase, a decrease, or no change in activity as compared to the wildtype protein.

The term "NPC1 protein, derivative, or functional variant thereof," which can include a "mutant NPC1 protein," refers to any non-wildtype NPC1 sequence or fragment thereof. Typically, a "mutant NPC1 protein" refers to a non-wildtype NPC1 polypeptide that has an aberrant function as compared to a wildtype NPC1 protein, and which results in NPC1 disease. However, the term "NPC1 protein, derivative, or functional variant thereof" is meant to be broad enough to encompass an NPC1 mutant protein, but also any other NPC1 protein carrying a genetic change (including a fragment) that may result an NPC1 protein having any of an increase, a decrease, or no change in activity as compared to the wildtype NPC1 protein. In the case of the present invention, the "NPC1 protein, derivative, or functional variant thereof" can also refer to homologous NPC1 proteins from non-human sources, e.g., mouse, monkey, horse, rabbit, and the like.

The term "NPC2" refers to the wildtype NPC1 gene, various mutant forms of which are associated with Neimann-Pick Type C disease by leading to the accumulation of intracellular unesterified cholesterol. For convenience, the human gene is referred to as hNPC2 or NPC2 and the murine gene as m NPC2 or Npc2 (this same nomenclature is also used to distinguish between the human and murine cDNAs and proteins). Where no "h" or "m" designation is given, reference to the human NPC2 gene generally is intended. The definition of an NPC2 gene includes the various sequence polymorphisms that exist in the species in question, i.e., the term "hNPC2" or a wildtype hNPC2 encompasses all various sequence polymorphisms in humans.

The term "NPC2 derivative gene," which can include a "mutant NPC2 gene," refers to any non-wildtype NPC2 sequence. Typically, a "mutant NPC2 gene" refers to a non-wildtype sequence that results in an aberrant functioning NPC2 protein, and thus, NPC disease. However, the term "NPC2 derivative gene" is meant to be broad enough to encompass an NPC2 mutant gene, but also any other NPC2 gene carrying a genetic change that may result an NPC2 protein having any of an increase, a decrease, or no change in activity as compared to the wildtype protein.

The term "NPC2 protein, derivative, or functional variant thereof," which can include a "mutant NPC2 protein," refers to any non-wildtype NPC2 sequence or fragment thereof. Typically, a "mutant NPC2 protein" refers to a non-wildtype NPC2 polypeptide that results has an aberrant function as compared to a wildtype NPC1 protein, and which results in NPC2 disease. However, the term "NPC2 protein, derivative, or functional variant thereof" is meant to be broad enough to encompass an NPC2 mutant protein, but also any other NPC2 protein carrying a genetic change (including a fragment) that may result an NPC2 protein having any of an increase, a decrease, or no change in activity as compared to the wildtype NPC2 protein. In the case of the present invention, the "NPC2 protein, derivative, or functional variant thereof" can also refer to homologous NPC2 proteins from non-human sources, e.g., mouse, monkey, horse, rabbit, and the like.

The term "NPC sufferer" or "NPC homozygote" refers to a person who carries a mutant NPC1 or NPC2 gene, such that the person exhibits clinical symptoms of Niemann-Pick type C disease.

The term "NPC carrier" or "NPC heterozygote" refers to a person who does not exhibit clinical symptoms of NPC but who carries one mutant form of the NPC1 or NPC2 gene and may transmit this mutant gene to progeny.

As used herein, the term "cholesterol storage disease or disorder" is meant to refer to a disease or disorder of or related to cholesterol metabolism, optionally that is treatable via use of gene therapy for delivery of NPC to a subject. Exemplary "cholesterol storage disease or disorders" include but are not limited to Niemann-Pick disease, type C1. Whether cholesterol storage and related pathophysiology may be impacted by NPC1 function in other conditions is certain and extends the utility of NPC directed therapies, specifically NPC1 gene therapy, toward other more common disorders in the future. For example, a subset of neuropsyciatric disorders, such as dementia, seizures, and atherosclerotic brain disease might to be influenced by or improved after cholesterol reduction mediated by NPC1 activity and as such, these groups of patients might be candidates for NPC1 viral gene therapy.

Terms Relating to Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization; B. D. Hames & S. J. Higgins eds. (1985); Transcription And Translation; [B. D. Hames & S. J. Higgins, eds. (1984); Animal Cell Culture; R. I. Freshney, ed. (1986); Immobilized Cells And Enzymes; IRL Press, (1986); B. Perbal, A Practical Guide To Molecular Cloning (1984); F. M. Ausubel et al. (eds.), Current Protocols in Molecular Biology, John Wiley & Sons, Inc. (1994).

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein, may be associated with other proteins or nucleic acids, or both, with which it associates in the cell, or with cellular membranes if it is a membrane-associated protein. In a specific embodiment, an isolated NPC1 protein is a recombinant NPC1 protein expressed from an expression vector. An isolated material may be, but need not be, purified.

As used herein, the term "cDNA" (complementary DNA) refers to a piece of DNA lacking internal, non-coding segments (introns) and regulatory sequences that determine transcription. cDNA can be synthesized in the laboratory by reverse transcription from messenger RNA extracted from cells.

As used herein, the term "ORF" (open reading frame) refers to a series of nucleotide triplets (codons) coding for amino acids without any termination codons. These sequences are usually translatable into a peptide.

As used herein, the term "ortholog" refers to two nucleotide sequences that share a common ancestral sequence and diverged when a species carrying that ancestral sequence split into two species. Orthologous sequences are also homologous sequences.

As used herein, the terms "probes" and "primers" refers to oligonucleotide sequences that may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987). "Primers" are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the human NPC1 cDNA or gene will anneal to a-target sequence such as an NPC1 gene homolog from rat contained within a genomic rat genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the NPC1 cDNA or gene sequences.

The invention thus includes isolated nucleic acid molecules that comprise specified lengths of the disclosed NPC1 DNA (or cDNA) or gene sequences. Such molecules may comprise at least 20, 25, 30, 35, 40 or 50 consecutive nucleotides of these sequences and may be obtained from any region of the disclosed sequences.

As used herein, a "vector" nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. A vector may include a "gene transfer vector," "gene therapy vector," or "gene therapy contruct," or similar terms, which refer to specific vector constructs that are suitable to conduct gene transfer to administer a desired gene.

The terms "vector," "cloning vector," and "expression vector" mean the vehicle by which an ASM DNA or RNA sequence (e.g., a foreign gene) can be introduced into a host cell so as to transform the host and promote expression (e.g., transcription and translation) of the introduced sequence. Vectors include any genetic element, such as a plasmid, phage, transposon, cosmid, chromosome, virus, virion, etc., which is capable of replication when associated with the proper control elements and which can transfer ASM gene sequences between cells. Thus, the term includes cloning and expression vehicles, as well as viral vectors.

As used herein, the term "expression system" means a host cell and compatible vector under suitable conditions, e.g., for the expression of an NPC1 protein coded for by foreign DNA carried by the vector and introduced to the host cell. Common expression systems include E. coli host cells and plasmid vectors, insect host cells such as Sf9, Hi5 or S2 cells and Baculovirus vectors, and expression systems, and mammalian host cells and vectors. The term "expression system" also may refer to a suitable gene therapy vector, which may be delivered by any means, including ex vivo and in vivo methods.

The term "host cell" means any cell of any organism that is selected, modified, transformed, grown, or used or manipulated in any way, for the production of a substance by the cell, for example the expression by the cell of a human ASM gene, including a DNA or RNA sequence, or the NPC1 enzyme. Host cells can further be used for preliminary evaluation of other assays. A "recombinant DNA molecule" is a DNA molecule that has undergone a molecular biological manipulation or engineering. In one embodiment of the invention, the host cell is a fibroblast.

A "gene" is a sequence of nucleotides that code for a "gene product". Generally, a gene product is a protein. However, a gene product can also be another type of molecule in a cell, such as an RNA (e.g., a tRNA or a rRNA). For the purposes of the present invention, a gene product also refers to an mRNA sequence which may be found in a cell. As used herein, a gene can refer to the nucleotide sequences encoding wild-type or mutant NPC1 or NPC2 genes.

As used herein, a "transformed cell" is a cell into which has been introduced a nucleic acid molecule by molecular biology techniques or gene therapy techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration and includes both in vitro and in vivo conditions.

As used herein, the term "purified" does not require absolute purity; rather, it is intended as a relative term. Thus, for example, a purified NPC1 protein preparation is one in which the NPC1 protein is more pure than the protein in its natural environment within a cell. Preferably, a preparation of an NPC1 protein is purified such that the NPC1 protein represents at least 50% of the total protein content of the preparation.

As used herein, the term "operably linked" refers to where a first nucleic acid sequence (e.g., an NPC1 gene) is operably linked with a second nucleic acid sequence (e.g., a promoter sequence) when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

As used herein, the term "recombinant nucleic acid" is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

As used herein, the term "sequence identity" refers to the similarity between two nucleic acid sequences, or two amino acid sequences and is expressed in terms of the similarity between the sequences, otherwise referred to as sequence identity. Sequence identity is frequently measured in terms of percentage identity (or similarity or homology); the higher the percentage, the more similar the two sequences are. Homologs of the human and mouse NPC1 proteins will possess a relatively high degree of sequence identity when aligned using standard methods.

Methods of alignment of sequences for comparison are well-known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI online site under the "BLAST" heading. A description of how to determine sequence identity using this program is available at the NCBI online site under the "BLAST overview" subheading.

Homologs of the disclosed NPC1 and NPC2 proteins are typically characterized by possession of at least 70% sequence identity counted over the full length alignment with the disclosed amino acid sequence of either the human or mouse NPC1/NPC2 sequences using the NCBI Blast 2.0, gapped blastp set to default parameters. Proteins with even greater similarity to the reference sequences will show increasing percentage identities when assessed by this method, such as at least 75%, at least 80%, at least 90% or at least 95% sequence identity. When less than the entire sequence is being compared for sequence identity, homologs will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI online site under the "Frequently Asked Questions" subheading. One of skill in the art will appreciate that these sequence identity ranges are provided for guidance only; it is entirely possible that strongly significant homologs could be obtained that fall outside of the ranges provided. The present invention provides not only the peptide homologs are described above, but also nucleic acid molecules that encode such homologs, such as those generated by codon optimization. In an embodiment, changing the nucleotide sequence on the corresponding codons will generate a synthetic NPC1 or NPC2 gene that would have improved translation efficiency and detection in the presence of the endogenous gene.

One indication that two nucleic acid sequences are substantially identical is that the polypeptide which the first nucleic acid encodes is immunologically cross reactive with the polypeptide encoded by the second nucleic acid (e.g., a human NPC1 protein and an NPC1 homolog from another species, or a variant human NPC1 protein).

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993) and are otherwise known in the art.

Terms Relating to Gene Therapy

The term "gene therapy" refers to a method of changing the expression of an endogenous gene by exogenous administration of a gene, i.e., a wildtype or mutant NPC1 or NPC2 gene. As used herein, gene therapy also refers to the replacement of a defective NPC1 or NPC2 gene, or replacement of a missing NPC1 or NPC2 gene, by introducing a functional gene or portion of a gene corresponding to the defective or missing NPC1 or NPC2 gene into somatic or stem cells of an individual in need. Gene therapy can be accomplished by "ex vivo" methods, in which differentiated or somatic stem cells are removed from the individual's body followed by the introduction of a normal copy of the defective gene into the explanted cells using a viral vector as the gene delivery vehicle. In addition, in vivo transfer involves direct gene transfer into cells in the individual in situ using a broad range of viral vectors (e.g., AAV), liposomes, nanoparticles, protein:DNA complexes, modified nucleic acids or naked DNA in order to achieve a therapeutic outcome.

The term "transgene" refers to a polynucleotide that is introduced into a cell of and is capable of being expressed under appropriate conditions and confers a desired property to a cell into which it was introduced, or otherwise leads to a desired therapeutic outcome.

The terms "genome particles (gp)," or "genome equivalents," or genome copies (gc) as used in reference to a viral titer, refer to the number of virions containing the recombinant AAV DNA genome, regardless of infectivity or functionality. The number of genome particles in a particular vector preparation can be measured by procedures such as described elsewhere herein, or for example, in Clark et al. (1999) *Hum. Gene Ther.*, 10:1031-1039; Veldwijk et al. (2002) *Mol. Ther.*, 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described elsewhere herein, or for example, in Xiao et al. (1997) *Exp. Neurobiol.*, 144:113-124; or in Fisher et al. (1996) *J. Virol.*, 70:520-532 (LFU assay).

Terms Relating to Therapeutic Application

The present invention further provides a method for the prevention or treatment of Type A and Type B NPD, which method comprises increasing the expression or activity of the mutant ASM enzyme, or by increasing the activity of recombinant, wild-type replacement ASM enzyme, in a subject or patient in need of such treatment.

As used herein, the term "administering" is meant to refer to a means of providing the composition (e.g., to the subject in a manner that results in the composition being inside the subject's body. Such an administration can be by any route including, without limitation, subcutaneous, intradermal, intravenous, intra-arterial, intraperitoneal, sublingual, buccal, and intramuscular. In certain embodiments, the delivery may be appropriate for CNS delivery, e.g., epidural, intracerebral, or intracerebroventricular.

The invention provides a number of compositions (e.g., sequences and vectors) that are useful for the development of highly specific drugs to treat or prevent a disease or disorder in a subject, as further characterized by the methods delineated herein. In addition, the methods of the invention provide a facile means to identify therapies that are safe for use in subjects. Other disorders that can feature cholesterol storage are contemplated, including adult forms of dementia and conditions that may be caused, in part, by diminished activity of NPC1.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

A "subject" or "patient" is a human or an animal that has developed, or is likely to develop NPC disease, more particularly a mammal, preferably a rodent or a primate, and most preferably a human. In one embodiment, the patient is a member of the Ashkenazi Jewish population who has been diagnosed with, or who has been identified as having an increased risk of developing NPC disease due to inherited mutations in the NPC1 or NPC2 gene. In another embodiment, the patient is a member of the French Canadian population of Nova Scotia, an inhabitant of the Maghreb region (Tunisia, Morocco, Algeria) of North Africa, or a member of the Spanish-American population of southern New Mexico and Colorado. However, Niemann-Pick disease is pan-ethnic, and the term subject encompasses anyone in the world having, or genetically at risk of developing, NPC disease. The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Treatment", or "treating" as used herein, is defined as the application or administration of a therapeutic agent (e.g., an AAV-NPC vector) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. In the context of the present invention, the symptoms that may be alleviated can include, but are not limited to, the accumulation of sphingomyelin in reticuloendothelial lysosomes, which results in hepatosplenomegaly, psychomotor retardation, pulmonary abnormalities, progressive neurodegeneration. In some instances, treatment will prevent death resulting from NPC disease.

The term "prevention" refers to the prevention of the onset of the disease, which means to prophylactically interfere with a pathological mechanism that results in the disease. In the context of the present invention, such a pathological mechanism can be an increase expression of mutant NPC1 or NPC2.

The terms "effective dose" or "effective dosage" or "therapeutically effective amount" are defined as an amount sufficient to achieve or at least partially achieve the desired effect. The term "therapeutically effective dose" is defined as an amount sufficient to cure or at least partially arrest the disease and its complications in a patient already suffering from the disease or prevent the disease prophylactically. The term "patient" includes human and other mammalian subjects that receive either prophylactic or therapeutic treatment. As it pertains to the instant invention, the term "therapeutically effective amount" also is used herein to mean an amount or dose of a gene therapy vector encoding NPC1 or NPC2 (or a mutant or functional variant thereof) sufficient to increase the level of NPC1 or NPC2 activity over the mutant or defective level to about 3-5%, preferably by about 10%, and more preferably by about 30%, or about 40%, or about 50%, or about 60%, or about 70%, or about 80%, or about 90%, or about 95%, or even up to 100% of the level found in normal cells. Preferably, a therapeutically effective amount can ameliorate or prevent a clinically significant deficit in NPC1 or NPC2 in the subject. Alternatively, a therapeutically effective amount is sufficient to cause an improvement in a clinically significant condition in the subject, e.g., amelioration of progressive neurodegeneration in Type C NPD patients.

Certain methodologies of the instant invention include at least one step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a gene therapy methodology, as described herein. For example, a transcription rate, mRNA level, translation rate, protein level, biological activity, cellular characteristic or property, genotype, phenotype, etc. can be determined prior to introducing an AAV or other vector of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Other definitions appear in context throughout the disclosure.

Gene Therapy Vectors

In one aspect, the present invention relates to gene therapy vectors or constructs comprising NPC1 and/or NPC2 genes, or derivatives and/or mutants thereof, which are operably linked to at least a promoter element that is capable of being expressed in a tissue of the central nervous system. In certain embodiments, the promoter is a neuronal-specific calmodulin promoter or derivative thereof. In other embodiments, the promoter is a constitutive promoter, e.g., an EF1α constitutive promoter or derivative thereof, which is capable of being expressed in neuronal tissues. As demonstrated by a reduction to practice using accepted NPC mouse models, the gene therapy vectors of the present invention were effective in treating and/or preventing NPC.

In certain embodiments, the gene therapy vectors or constructs comprise an NPC1 gene, or a derivative and/or mutant NPC1 gene. The NPC1 gene, including any derivatives and/or mutants thereof, can encode a wildtype NPC1 polypeptide, any a functional fragment or variant thereof. The variants or functional fragments of NPC1 may have increased or decreased activity as compared to a wildtype NPC1 protein, or the activity may be unchanged.

In certain other embodiments, the gene therapy vectors or constructs comprise an NPC2 gene, or a derivative and/or mutant NPC2 gene. The NPC2 gene, including any derivatives and/or mutants thereof, can encode a wildtype NPC2 polypeptide, any a functional fragment or variant thereof. The variants or functional fragments of NPC2 may have increased or decreased activity as compared to a wildtype NPC2 protein, or the activity may be unchanged.

The NPC1 and/or NPC2 genes or nucleotide sequences comprising a coding region for NPC1 and/or NPC2 proteins may be obtained from any source, including human, mouse, horse, pig, monkey, and the like. The nucleotide sequences encoding NPC1 and/or NPC2 in human, and NPC1 and/or NPC2 homologs from species other than human, are generally known in the art and can be obtained from public sequence repositories, including, for example, GenBank. In particular, cDNA sequences encoding NPC1 and/or NPC2 proteins (or variants thereof) may also be obtained from public sequence repositories such as GenBank.

For example, the following NPC1 sequences (or any variants comprising or genetically modified to comprise any mutations that encode a functional variant NPC1) are contemplated for use in the gene therapy constructs of the present invention:

GenBank Accession No. BC063302 (*Homo sapiens* Niemann-Pick disease, type C1, mRNA (cDNA clone), which provides the NPC1 cDNA coding sequence (SEQ ID NO: 10, FIG. 13) and the NPC1 polypeptide amino acid sequence (SEQ ID NO: 9, FIG. 12);

GenBank Accession No. BC117178 (*Homo sapiens* NPC1 (Niemann-Pick disease, type C1, gene)-like 1 mRNA (cDNA clone), which provides a variant NPC1 cDNA coding sequence and NPC1 polypeptide amino sequence;

GenBank Accession No. BC143756 (*Homo sapiens* NPC1 (Niemann-Pick disease, type C1, gene)-like 1, mRNA (cDNA clone), which provides a variant NPC1 cDNA coding sequence and NPC1 polypeptide amino sequence;

GenBank Accession No. AF258783.1 (*Felis catus* Niemann-Pick type C1 disease protein (NPC1) mRNA, complete cds) which provides cat NPC1 cDNA coding sequence and cat NPC1 polypeptide amino sequence;

GenBank Accession No. BC054539 (Mouse Npc1 (Niemann-Pick disease, type C1, gene) mRNA (cDNA clone), which provides mouse Npc1 cDNA coding sequence and mouse NPC1 polypeptide amino sequence;

GenBank Accession No. BC151276 (Bovine NPC1 (Niemann-Pick disease, type C1, gene) mRNA (cDNA clone), which provides bovine NPC1 cDNA coding sequence and bovine NPC1 polypeptide amino sequence; and GenBank Accession No. BC090541 (Zebrafish NPC1 (Niemann-Pick disease, type C1, gene) mRNA (cDNA clone), which provides Zebrafish NPC1 cDNA coding sequence and Zebrafish NPC1 polypeptide amino sequence.

The disclosed subject matter further encompasses any NPC1 gene and/or polypeptide sequence not expressly indicated here, but which is publicly available at the time of the present invention, or which becomes available after the time of the invention.

For example, the following NPC2 sequences (or any variants comprising or genetically modified to comprise any mutations that encode a functional variant NPC2) are contemplated for use in the gene therapy constructs of the present invention:

GenBank Accession No. BC002532 (*Homo sapiens* Niemann-Pick disease, type C2, mRNA (cDNA clone), which provides the NPC2 cDNA coding sequence (SEQ ID NO: 12) and the NPC2 polypeptide amino acid sequence (SEQ ID NO: 11);

GenBank Accession No. KJ893081 (Synthetic construct *Homo sapiens* clone ccsbBroadEn_02475 NPC2 gene, encodes complete protein), which provides the NPC2 cDNA coding sequence and the NPC2 polypeptide amino acid sequence;

GenBank Accession No. BC045895 (Zebrafish Niemann-Pick disease, type C2, mRNA (cDNA clone), which provides the Zebrafish NPC2 cDNA coding sequence and the Zebrafish NPC2 polypeptide amino acid sequence;

GenBank Accession No. NM_173918 (Bovine Niemann-Pick disease, type C2, mRNA (cDNA clone), which provides the Bovine NPC2 cDNA coding sequence and the Bovine NPC2 polypeptide amino acid sequence;

GenBank Accession No. BC102504 (Bovine Niemann-Pick disease, type C2, mRNA (cDNA clone), which provides the Bovine NPC2 cDNA coding sequence and the Bovine NPC2 polypeptide amino acid sequence; and GenBank Accession No. NM_214206 (Pig Niemann-Pick disease, type C2, mRNA (cDNA clone), which provides the pig NPC2 cDNA coding sequence and the Pig NPC2 polypeptide amino acid sequence.

The disclosed subject matter further encompasses any NPC2 gene and/or polypeptide sequence not expressly indicated here, but which is publicly available at the time of the present invention, or which becomes available after the time of the invention.

In preferred embodiments, the transgene encodes a biologically active molecule, expression of which in the subject, e.g., in the CNS of a subject, results in at least partial correction of the cholesterol storage disease or disorder, for example, Niemann-Pick disease, Type C. In some embodiments, the transgene encodes NPC1 (or a functional variant and/or fragment thereof). In other embodiments, the transgene encodes NPC2 (or a functional variant and/or fragment thereof). The genomic and functional mRNA, cDNA and corresponding polypeptide sequences of human, mouse, or other species NPC1 and NPC2 genes and proteins are known, as indicated above, and in particular are available as GenBank Accession Nos.: NM_000271.4; NM_008720.2; NM_006432.3; NM_023409.4; and corresponding polypeptides NP_000262.2; NP_032746.2; NP_006423.1; and NP_075898.1.

Nucleotide sequences encoding NPC1 or NPC2 genes (or variants thereof) may be obtained by any known molecular biology technique, including by cloning, synthesis, or PCR amplification. Oligonucleotides for using in amplification reactions and/or probes for use in gene cloning may be synthesized or otherwise obtained by any known means and based on the nucleotide sequences that flank the desired gene or coding region encoding the NPC1 or NPC2 target genes. Methods and techniques for gene cloning and/or PCR amplification are well known in the art and are discussed elsewhere herein.

The gene therapy constructs described herein also comprise a vector (or gene therapy expression vector) into which the gene of interest (e.g., NPC1 or NPC2 gene) is cloned or otherwise which includes the gene of interest in a manner such that the nucleotide sequences of the vector allow for the expression (constitutive or otherwise regulated in some manner) of the gene of interest. The vector constructs herein described include any suitable gene expression vector that is capable of being delivered to a tissue of interest (e.g., CNS) and which will provide for the expression of the gene of interest in the selected tissue of interest (e.g., CNS). In a preferred embodiment, the gene therapy vector is capable of efficient delivery to a tissue of the central nervous system, including the spine and the brain, and in particular, is capable of crossing the blood-brain barrier of the brain.

In a preferred embodiment, the vector is an adeno-associated virus (AAV) vector because of the capacity of AAV vectors to cross the blood-brain barrier and transduction of neuronal tissue. In the methods disclosed herein, AAV of any serotype can be used, though in certain embodiments, it is advantageous to use a vector that is capable of undergoing retrograde axonal transport in a disease-compromised brain. The serotype of the viral vector used in certain embodiments of the invention is selected from the group consisting of AAV1, AAV2, AAV3, AAV4, AAV5, AAV6, AAV7, AAV8, AAV9, AAVrh8, AAVrh10, AAVrh33, AAV rh34, AAV Anc80, AAV PHP.B, and others (see, e.g., Gao et al. (2002) PNAS, 99:11854-11859; and Viral Vectors for Gene Therapy: Methods and Protocols, ed. Machida, Humana Press, 2003, incorporated herein by reference). Other serotype besides those listed herein are also contemplated. In certain exemplary embodiments, AAV 2/9 is used. The herein disclosed compositions and methods may also use AAV chimeric vectors, whereby portions of AAV are fused with other similar vectors, such as Adenovirus.

AAV vectors are derived from single-stranded (ss) DNA parvoviruses that are nonpathogenic for mammals (reviewed in Muzyscka (1992) Curr. Top. Microb. Immunol., 158:97-129, incorporated herein by reference). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, the AAV backbone, comprising sequences between two AAV inverted terminal repeats (ITRs), is pseudotyped using the serotype 2 capsid to create an AAV2 vector. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003, incorporated herein by reference). Additionally, AAV-based gene therapy targeted to cells of the CNS has been described in U.S. Pat. Nos. 6,180,613 and 6,503,888 (each of which are incorporated herein by reference).

Optionally, the AAV viral capsid is AAV2/9, AAV9, AAVrh8, AAVrh10, AAV Anc80, or AAV PHP.B.; however, the serotype of the viral capsid used in certain embodiments of the invention can be selected from among known viral capsids, including AAV viral capsids of other known serotypes.

Optionally, the gene therapy vector, e.g., AAV or AAV-based vector, can be modified to improve virus uptake into the target tissue of interest (e.g., CNS), viral stability, and tropism. For example, the capsid of an AAV vector may be modified with a ligand (e.g., synthetic or naturally occurring small molecule, peptide, or polypeptide, or other biomolecule) that binds to a receptor at or in the tissue of interest (e.g., CNS). Other modification are possible to improve and/or enhance the functional properties of the vector being used to both target the tissue of interest and allow the construct to enter and effectively transduce the target cells. Such modifications will be within the skill set of a person having ordinary skill in the art.

Further information regarding the use of AAV vectors can be found in the art, for example, in Kaplitt et al. (1994) Nat. Genet., 8:148-154; Bartlett et al. (1998) Hum. Gene Ther., 9:1181-1186; and Passini et al. (2002) J. Neurosci., 22:6437-6446, each of which are incorporated herein by reference. Furthermore, these viral vectors can transduce a variety of CNS cell types, including neurons, when delivered by the systemic route, intrathecal route or by direct brain injection.

As further contemplated herein, the gene therapy vectors may comprise a transgene (e.g., NPC1 or NPC2) that is operably linked to a promoter or other genetic transcriptional and/or translational control elements. Certain AAV vectors pre-engineered with or comprising promoters can be obtained from public sources, including, for example www.vectorbiolabs.com or www.addgene.org, which are incorporated herein by reference.

In certain embodiments, the promoter is promoter which is capable of efficient inducible expression in the CNS. In still other embodiments, the promoter is constitutively active in the CNS. In certain preferred embodiments, the promoter provides for selective expression in the CNS, and expression outside of the CNS is limited or entirely absent. Promoter sequences having differing characteristics and expression profiles are well known in the art, including those that are tissue-specific, tissue-non-specific, constitutive, and inducible. Reference can be further made to, for example, Papadakis et al., "Promoters and Control Elements: Designing Expression Cassettes for Gene Therapy," Current Gene Therapy, 2004, 4, 89-113, the contents of which are incorporated herein by reference. Promoters contemplated by the present invention include, but are not limited to: Apo A-I, ApoE, serpina (TBG), alpha-1-antitrypsin (hAAT) (liver specific); MCK (muscle specific); GFAP, NSE, Synapsin I, Preproenkephalin, Dopamine b-hydroxylase (dbH), Prolactin, Myelin basic protein (neuronal-specific), GUSB, CBA, CAG and Ankyrin (erythroid specific).

In a particular embodiment, the disclosed compositions and methods utilize an AAV vector in conjunction with a $_{mini}$-calmodulin promoter (aka CaMKII or $_{mini}$CaMKII promoter) (SEQ ID NO: 3) where CaMKII or $_{mini}$CaMKII can be from human or mouse or any other mammal and has neuronal-specific tropism and expression characteristics.

In another particular embodiment, the disclosed compositions and methods utilize an AAV vector in conjunction with an elongation factor 1-alpha promoter (aka EF1α promoter) (SEQ ID NO: 8) which is constitutive and expresses in neuronal tissues. For the purpose of this document EF1α can be intact or truncated and terms EF1α or EF1α(short) or $_{mini}$EF1α can be used interchangeably. Also, EF1α is same as Ef1α and can be obtained from human or mouse.

Methods of Treatment

In one aspect, the present invention provides methods for treating a cholesterol storage disease or disorder in mammals, such as Neimann-Pick disease, Type C. In preferred embodiments, the populations treated by the methods of the invention include, but are not limited to, patients having or at risk for developing a cholesterol storage disease or disorder, e.g., Niemann-Pick disease, type C1, particularly, if such a disease affects the CNS. In an illustrative embodiment, the disease is Niemann-Pick disease, Type C1.

In certain aspects of the invention, the method of treating a cholesterol storage disease or disorder comprises administration of a high titer gene therapy vector described herein (e.g., an AAV-based gene therapy vector) carrying a therapeutic transgene so that the transgene product is expressed at a therapeutic level in the CNS of a subject. In some embodiments, the viral titer of the composition is at least: (a) 5, 6, 7, 8, 8.4, 9, 9.3, 10, 15, 20, 25, or $50 \times 10^{12}$ gc/ml; (b) 5, 6, 7, 8, 8.4, 9, 9.3, 10, 15, 20, 25, or $50 \times 10^{9}$ to/ml; or (c) 5, 6, 7, 8, 8.4, 9, 9.3, 10, 15, 20, 25, or $50 \times 10^{10}$ iu/ml. In further embodiments, the administration is accomplished by direct intraparenchymal injection of solution comprising a high titer gene therapy vector described herein (e.g., an AAV-based gene therapy vector) into the diseased brain, thereafter the transgene is expressed distally, contralaterally or ipsilaterally, to the administration site at a therapeutic level at least 2, 3, 5, 8 10, 15, 20, 25, 30, 35, 40, 45, or 50 mm from the administration site.

In further embodiments, the administration is accomplished by direct intrathecal injection of a solution comprising a high titer gene therapy vector described herein (e.g., an AAV-based gene therapy vector) into the spinal fluid compartment, as is routine for practioners of the art, and thereafter the transgene is expressed distally, contralaterally, ipsilaterally and globally in the CNS, to the administration site at a therapeutic level at least 2, 3, 5, 8 10, 15, 20, 25, 30, 35, 40, 45, or 50 mm from the administration site.

In certain embodiments, the transgene product (e.g., NPC1 or NPC2 polypeptide) is expressed at a therapeutic level in a second site within the CNS distal to the first site. The distance between the first and the second sites is defined as the minimal distance region between the site of administration (first site) and the boundary of the detectable transduction of the distal site (second site) as measured using procedures known in the art, e.g., magnetic resonance imaging including spectroscopy or direct brain biopsy. Some neurons in the CNS of larger mammals may span large distances by virtue of their axonal projections. For example, in humans, some axons may span a distance of 1000 mm or greater. Thus, in various methods of the invention, a gene therapy vector of the invention can be axonally transported along the entire length of the axon at such a distance to reach and transduce the parent cell body.

A site of vector administration within the CNS can be chosen based on the desired target region of neuropathology and, optionally, the topology of brain circuits involved when an administration site and the target region have axonal connections. In certain embodiments, the target region can be defined, for example, using 3-D stereotaxic coordinates. In some embodiments, the administration site is chosen so that at least 0.1, 0.5, 1, 5, or 10% of the total amount of vector injected is delivered distally at the target region of at least 1, 200, 500, or 1000 mm$^3$. An administration site may be localized in a region innervated by projection neurons connecting distal regions of the brain. For example, the substantia nigra and ventral tegmental area send dense projections to the caudate and putamen (collectively known as the striatum). Neurons within the substantia nigra and ventral tegmentum can be targeted for transduction by retrograde transport of a gene therapy construct described herein (e.g., AAV based vector) following injection into the striatum. As another example, the hippocampus receives well-defined, predictable axonal projections from other regions of the brain. Other administration sites may be localized, for example, in the spinal cord, brainstem (medulla and pons), mesencephalon, cerebellum, diencephalon (thalamus, hypothalamus), telencephalon (corpus striatum, cerebral cortex, or, within the cortex, the occipital, temporal, parietal or frontal lobes), or combinations thereof.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Sterotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000. If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

In certain embodiments, the target site can be located any region of the CNS, including the brain and the spinal cord, that contains a neurons that project to the first (administration) site. In some embodiments, the second site is in a region of the CNS chosen from the substantia nigra, the medulla oblongata, or the spinal cord.

To deliver a gene therapy vector described herein specifically to a particular region of the central nervous system, especially to a particular region of the brain, it may be administered by stereotaxic microinjection. For example, on the day of surgery, patients will have the stereotaxic frame base fixed in place (screwed into the skull). The brain with stereotaxic frame base (MM-compatible with fiduciary markings) will be imaged using high resolution MM. The MM images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector in a pharmaceutically acceptable carrier will then be injected. The AAV vector is then administered by direct injection to the primary target site and retrogradely transported to distal target sites via axons. Additional routes of administration may be used, e.g., superficial cortical application under direct visualization, or other non-stereotaxic application.

Optionally, non-CNS delivery can also be performed, e.g., for cholesterol storage diseases or disorders where non-CNS delivery would also be desirable. Such non-CNS delivery of the compositions (e.g., constructs) of the instant invention can be performed in addition to or as an alternative to CNS delivery. In certain such embodiments, injection, e.g., intravenous, intraperitoneal, etc. injection can be performed using the compositions of the instant invention. Direct delivery to large peripheral nerves is also considered.

In yet another method, a suitable AAV vector configured to express NPC1 or NPC2 can be encapsidated with a capsid known to afford transduction of the blood brain barrier and further penetration of the CNS and its elements. In this embodiment, the AAV vector can be delivered systemically, by IV infusion, and engender both peripheral and CNS correction, depending upon the promoter and serotype of the vector.

The total volume of material to be administered, and the total number of vector particles to be administered, will be determined by those skilled in the art based upon known aspects of gene therapy. Therapeutic effectiveness and safety can be tested in an appropriate animal model. For example, for NPC, in any Npc1$^{-/-}$ model mouse such as the Npc$^{nih}$ homozygous mice.

In experimental mice, the total volume of injected vector, e.g., AAV vector, solution is, for example, between 1 to 10 µl. For other mammals, including the human brain, volumes and delivery rates are appropriately scaled. For example, it has been demonstrated that volumes of 150 µl can be safely injected in the primate brain (Janson et al. (2002) *Hum. Gene Ther.*, 13:1391-1412). Treatment may consist of a single injection per target site, or may be repeated along the injection tract, if necessary. Multiple injection sites can be used. For example, in some embodiments, in addition to the first administration site, a composition comprising a gene therapy vector described herein carrying a transgene is administered to another site that can be contralateral or ipsilateral to the first administration site.

In another aspect, the invention provides a method of delivering a transgene product to a target cell of the CNS, which is a neuron or a glial cell, in a mammal afflicted with a cholesterol storage disease or disorder, e.g., Niemann-Pick disease, type C. The method comprises contacting an axonal ending of a neuron with a composition comprising an AAV vector carrying at least a part of a gene encoding a therapeutic transgene product, e.g., NPC1; allowing the viral particles to be endocytosed and retrogradely transported intracellularly along the axon to the nucleus of the neuron; allowing the transgene product to be expressed and transported within the membrane(s) of the neuron, wherein the transgene product thereby alleviates pathology related to cholesterol storage. In some embodiments, the concentration of the AAV vector in the composition is at least: (a) 5, 6, 7, 8, 8.4, 9, 9.3, 10, 15, 20, 25, or 50×10$^{12}$ gc/ml; (b) 5, 6, 7, 8, 8.4, 9, 9.3, 10, 15, 20, 25, or 50×10$^9$ to/ml; or (c) 5, 6, 7, 8, 8.4, 9, 9.3, 10, 15, 20, 25, or 50×10$^{10}$ iu/ml.

The present invention provides for both prophylactic and therapeutic methods of treating a subject at risk of (or susceptible to) a disease or disorder caused, in whole or in part, by altered cholesterol storage, optionally treatable via selective or systemic delivery of a NPC1- and/or NPC2-containing gene therapy vector to a subject.

In certain aspects, the invention provides a method for preventing in a subject, a disease or disorder as described herein (including, e.g., NPC), by administering to the subject a gene therapy composition. Subjects at risk for the disease can be identified by, for example, one or a combination of diagnostic or prognostic assays known in the art (e.g., genetic assessment of the subject and/or phenotypic assessment). Administration of a prophylactic agent can occur prior to the detection of, e.g., NPC in a subject, or the manifestation of symptoms characteristic of the disease or disorder, such that the disease or disorder is prevented or, alternatively, delayed in its progression.

Another aspect of the invention pertains to methods of treating subjects therapeutically, i.e., altering the onset of symptoms of the disease or disorder. These methods can be performed in vitro (e.g., by culturing the cell with the gene therapy composition) or, alternatively, in vivo (e.g., by administering the gene therapy composition to a subject).

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with the gene therapy transgene of the present invention to that individual's drug response genotype. Pharmacogenomics allows a clinician or physician to target prophylactic or therapeutic treatments to patients who will most benefit from the treatment and to avoid treatment of patients who will experience toxic drug-related side effects.

Gene Therapy Compositions

The invention, in part, pertains to a gene therapy composition comprising the NPC-providing vectors as described herein. The gene therapy composition of the invention can gain entry into a cell or tissue, e.g., a CNS cell or tissue, for treating or preventing NPC disease or mitigating the complications, such as liver disease, neurological decline or seizures.

Advantageously, the gene therapy composition of the invention provides for a controlled delivery of an active gene, especially a therapeutic gene, to a site of action at an optimum rate and therapeutic dose. Thus, improvements in therapeutic index may be obtained by modulating the distribution of the active ingredient in the body and/or by modulating the promoter used in such gene therapy construct. Association of the gene therapy vector and/or viral vector containing such gene therapy vector with a delivery system enables, in particular, its specific delivery to the site of action or its controlled expression of a gene after targeting the action site. By reducing the amount of active gene therapy vector distributes to any compartments in which its presence is not desired, it is possible to increase the efficacy of the gene therapy agent, and to reduce any toxic side effects or even modify or restore activity of gene therapy agents. In this application, the capsid serotype can influence route of delivery, cellular transduction efficacy, and dose required for a therapeutic effect. The promoter of the vector further dictates cell type expression i.e., in all cells or only neurons and the degree to which expression occurs at the cellular level. As such, some promoters are stronger than others, and produce higher transgene expression. In another embodiment, microRNA (miRNA) binding sites are embedded in the 3' untranslated region of the therapeutic transgene to provide a cell specific inhibition of translation if the NPC transgene product is toxic in one cell type compared to another. This approach would minimize off target expression in cell types other than neurons if needed.

The invention also relates to pharmaceutical or diagnostic compositions comprising the NPC-including vectors of the invention and a pharmaceutically acceptable carrier. As such, direct RNA or DNA or modified forms if such, including peptide or covalently modified nucleic acids, injections in the brain or other locations are considered using the therapeutic transgenes described in this application. In another embodiment, nanoparticles containing nucleic acids encoding NPC1 are used for gene delivery. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

In certain embodiments, the present invention provides for a viral vector composition comprising a gene therapy agent (e.g., NPC1 or NPC2 operably linked to a tissue-specific or systemic promoter, optionally within a plasmid corresponding to the form of viral delivery system employed, e.g., AAV viral vector plasmid) of the present invention. The active viral vector can be suitably formulated and introduced into the environment of the cell by any means that allows for a sufficient portion of the sample to enter the cell to induce expression of the gene therapy agent, if it is to occur. Many formulations for AAV and other vector-based gene therapy delivery are known in the art and can be used.

Such compositions can include the gene therapy agent and a pharmaceutically acceptable carrier. Supplementary active compounds can also be incorporated into the compositions. The AAV capsid can likewise be modified to improve uptake and viral stability, and alter trophism.

A gene therapy composition can be formulated to be compatible with its intended route of administration. Examples of routes of administration include parenteral, e.g., intravenous, intracranial, intrathecal, intraventricular, intramuscular, intrahepatic, intradermal, subcutaneous, oral (e.g., inhalation, buccal, sublingual, intranasal), transdermal (topical), transmucosal, and rectal administration. Nucleic acids can be delivered using electrical or magnetic stimulation, or direct physical uptake using hydrodynamic pressure. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Gene therapy compositions suitable for injectable use can include sterile aqueous solutions or dispersions and sterile powders for the extemporaneous preparation of sterile injectable solutions or dispersion. For intravenous administration, in certain embodiments, carriers can include physiological saline, bacteriostatic water, Cremophor EL® (BASF, Parsippany, N.J.) or phosphate buffered saline (PBS). However, the art as relates to a specific viral delivery vector will be known to the skilled artisan and will provide appropriate constituents for a gene therapy vector composition. A composition for injection must be sterile (apart from the AAV or other viral vector employed for delivery) and should be fluid to the extent that easy syringability exists. In certain embodiments, such compositions are stable under the conditions of manufacture and storage and are preserved against the contaminating action of microorganisms such as bacteria and fungi. Exemplary carriers can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the gene therapy vectors disclosed herein in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

For administration by inhalation, gene delivery compositions can be delivered in the form of an aerosol spray from pressured container or dispenser which contains a suitable propellant, e.g., a gas such as carbon dioxide, or a nebulizer. Such methods include those described in U.S. Pat. No. 6,468,798, which is incorporated herein by reference.

The data obtained from the cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For a compositions used in the method of the invention, the therapeutically effective dose can be estimated initially from cell culture assays. A dose may be formulated in animal models to achieve a circulating plasma concentration range that includes the $IC_{50}$ (i.e., the concentration of the test compositions which achieves a half-maximal inhibition of symptoms) as determined in cell culture. Such information can be used to more accurately determine useful doses in humans. Levels in plasma may be measured, for example, by high performance liquid chromatography.

Expression constructs of the invention can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057) or by any aforementioned delivery route. The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The expression constructs may be constructs suitable for use in the appropriate expression system and include, but are not limited to retroviral vectors, linear expression cassettes, modified mRNAs, plasmids and viral or virally-derived vectors, as known in the art. The nucleic acids can be modified covalently, such as peptide nucleic acids or base modified ribonucleic acids. Such expression constructs may include one or more promoters as detailed elsewhere herein.

Suitable amounts of a gene therapy composition must be introduced and these amounts can be empirically determined using standard methods.

The gene therapy composition can be formulated as a composition which comprises a pharmacologically effective amount of a transgene and/or viral vector containing a transgene, and pharmaceutically acceptable carrier. A pharmacologically or therapeutically effective amount refers to that amount of gene therapy agent effective to produce the intended pharmacological, therapeutic or preventive result. The phrases "pharmacologically effective amount" and "therapeutically effective amount" or simply "effective amount" refer to that amount of a gene therapy transgene effective to produce the intended pharmacological, therapeutic or preventive result. For example, if a given clinical treatment is considered effective when there is at least a 20% increase in a measurable parameter associated with a disease or disorder, a therapeutically effective amount of a gene therapy composition for the treatment of that disease or disorder is the amount necessary to effect at least a 20% increase in that parameter. In another example, if a given clinical treatment is considered effective when there is at least 10%, 20%, 30%, 40%, 50%, 60%, 70%, or 80% or more increase in a measurable parameter associated with a disease or disorder, a therapeutically effective amount of a gene therapy composition for the treatment of that disease or disorder is the amount necessary to effect at least a 10%, 20%, 30%, 40%, 50%, 60%, 70%, or 80% or more increase in that parameter.

Markers of Transgene Expression/Activity

Toxicity and therapeutic efficacy of gene delivery compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Gene therapy compositions which exhibit high therapeutic indices are preferred. While gene therapy compositions that exhibit toxic side effects may be used, care should be taken to design a delivery system that targets such compositions to the site of affected tissue in order to minimize potential damage to uninfected cells and, thereby, reduce side effects.

In certain embodiments, membrane localization, including intracellular localization of a transgene or product thereof, e.g., NPC1, is assessed in the subject and/or in cells of the subject. In other embodiments, assessment of the efficacy of NPC1 transgene delivery is performed via measurement of cholesterol uptake (e.g., endocytic cholesterol uptake) of the cells of a subject and/or via phenotypic assessment of a subject before and after administration of the AAV-NPC composition(s). Such assessment can be performed within days of administration of an AAV-NPC composition of the invention, or can be performed at a time of, e.g., one week, two weeks, three weeks, one month, two months, three months, four months, five months, six months, one year or more post-administration. The use of previously described biomarkers such as unesterified cholesterol, sphingomyelin, bis(monoacylglycero)phosphate, glucosylceramide, lactosylceramide, globotriaosylceramide, free sphingosine, gangliosides GM2 and GM3; galectin-3 (LGALS3) a pro-inflammatory molecule, and cathepsin D (CTSD), a lysosomal aspartic protease; and cholesterol oxidation products and neurosteroids such as cholestane-3β,5α,6β-triol ('triol'), a cholesterol oxidation product that is elevated 10-fold in the plasma of NPC1 subjects, and 24(S)-hydroxycholesterol (24(S)-HC), an enzymatically generated oxygenated cholesterol that is reduced in the plasma of NPC1 subjects. Untargeted metabolomics are likewise envisioned to monitor the efficacy and activity of AAV gene therapy for NPC.

In certain embodiments, prior to treatment, a subject is assessed for the identity of genetic deficiency that has produced NPC in the subject—whether NPC1 or NPC2 and the subject is then administered an appropriate NPC1 or NPC2 transgene depending upon the outcome of such assessment. In another embodiment, the transgene encodes a transgene that has been codon optimized for human expression designated coNPC1 or coNPC2. Methods for diagnosing NP disease can be found, for example, in U.S. Pat. Nos. 4,039,388, 5,686,240, 6,426,198, and 7,045,675 each of which are incorporated by reference.

The invention further provides a method to treat related disorders of unesterified cholesterol accumulation, such as atherosclosis.

The level or activity of a transgene mRNA or polypeptide can be determined by a suitable method now known in the art or that is later developed, e.g., analyzing expression levels by PCR, hybridization, microarrays, or other similar methodologies. Suitable primers, probes, and oligonucleotides capable of performing such detection will be known and readily obtainable in the art. It can be appreciated that the method used to measure a transgenic mRNA and/or the expression of a transgenic protein can depend upon the nature of the transgene. Such measurements can be made on cells, cell extracts, tissues, tissue extracts or other suitable source material.

The determination of whether the expression of a transgene has been increased can be by a suitable method that can reliably detect changes in RNA or protein levels. In certain embodiments, the determination is made by introducing into the environment of a cell a gene therapy composition of the invention such that at least a portion of the gene therapy vector enters the cytoplasm (optionally, the nucleus; optionally, with nuclear chromosomal integration), and then measuring the level of the transgene RNA and/or polypeptide. The same measurement is made on identical untreated cells and the results obtained from each measurement are compared.

Combination Therapies

It is contemplated that the compositions of the current invention can be combined with other proposed therapies (e.g., for NPC) to slow disease progression and ameliorate symptoms, even in patients with advanced disease. There are no published standards of care for NPC other than symptomatic treatment of disease manifestations—seizures are controlled as possible and supportive care is provided as needed. In one embodiment, AAV gene therapy would be combined with the pharmaceutical excipient 2-hydroxypropyl-β-cyclodextrin (HPβCD). In another, AAV gene therapy would be combined therapies shown to have modest efficacy in mouse models or cell culture studies including treatment with antioxidants such as N-acetylcysteine; vitamin E or derivatives such as α-tocopherol or δ-tocopherol; miglustat, a small imino sugar that partially inhibits glucosylceramide synthase and the synthesis of all glucosylceramide-based glycosphingolipids; curcumin to compensates for the lysosomal calcium defect by elevating cytosolic calcium; the non-steroidal anti-inflammatory drug ibuprofen or related compounds to reduce central nervous system inflammation; donepezil, a widely used acetylcholinesterase (AChE) inhibitor; or Histone deacetylase inhibitors (HDACi) such as vorinostat. In another embodiment, AAV gene therapy would be combined with other therapies that have a theoretical basis for efficacy—such as those that influence cholesterol metabolism, but have limited efficacy to date. These include the cholesterol-lowering agents cholestyramine, lovastatin, and nicotinic acid as well as a low-cholesterol diet Dosage Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In certain embodiments, a suitable dosage unit of a transgene vector is in the range of 0.001 to 0.25 milligrams per kilogram body weight of the recipient per day, or in the range of 0.01 to 20 micrograms per kilogram body weight per day, or in the range of 0.001 to 5 micrograms per kilogram of body weight per day, or in the range of 1 to 500 nanograms per kilogram of body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. A gene therapy composition comprising the transgene can be administered once or on multiple occasions.

Data can be obtained from cell culture assays and animal studies to formulate a suitable dosage range for humans. The dosage of compositions of the invention can lie within a range of circulating concentrations that include the $ED_{50}$ (as determined by known methods) with little or no toxicity. The dosage may vary within this range depending upon the dosage form employed and the route of administration utilized. For a composition used in the method of the invention, the therapeutically effective dose can be estimated initially from cell culture assays. A dose may be formulated in animal models to achieve a circulating plasma concentration range of the composition that includes the $IC_{50}$ (i.e., the concentration of the test compound which achieves a half-maximal inhibition of symptoms) as determined in cell culture. Such information can be used to more accurately determine useful doses in humans. Levels of a gene therapy composition in plasma may be measured by standard methods, for example, by high performance liquid chromatography.

In certain embodiments, the dosage may be in terms of vector concentration. For example, the concentration of gene therapy vector described herein is at least: (a) 5, 6, 7, 8, 8.4, 9, 9.3, 10, 15, 20, 25, or $50 \times 10^{12}$ gc/ml; (b) 5, 6, 7, 8, 8.4, 9, 9.3, 10, 15, 20, 25, or $50 \times 10^{9}$ to/ml ("transducing units per ml"); (c) 5, 6, 7, 8, 8.4, 9, 9.3, 10, 15, 20, 25, or $50 \times 10^{10}$ iu/ml ("international units per ml"), or (d) 5, 6, 7, 8, 8.4, 9, 9.3, 10, 15, 20, 25, or $50 \times 10^{10}$ pfu/ml ("plaque forming units per ml").

Kits and/or Pharmaceutical Packages

The gene therapy compositions of the invention can be included in a kit and/or pharmaceutical package, container, pack, or dispenser together with instructions for administration.

The disclosure provides kits for the treatment or prevention of disease, e.g., NP disease, Type C. In one embodiment, the kit includes a therapeutic or prophylactic composition containing an effective amount of an agent of the invention (e.g., NPs) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject having or at risk of developing a disease. The instructions will generally include information about the use of the composition for the treatment or prevention of the disease (e.g., NPC). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The present invention is described by reference to the following Examples, which are offered by way of illustration and are not intended to limit the invention in any manner. Standard techniques well known in the art or the techniques specifically described below were utilized.

Example 1. Neuron-Specific Adeno-Associated Viral (AAV) Vector For NPC1 Delivery To develop a new class of gene-based therapeutics for NPC in humans, a series of adeno-associated viral (AAV) vectors were developed for delivery of the NPC1 gene, first to neurons and then to other cell types. An NPC1 gene was engineered for expression under the control of the calmodulin promoter. This expression cassette was cloned into an empty AAV2 vector, which created AAV-$_{mini}$calmodulin-NPC1. This vector was encapsidated with an AAV serotype 9 capsid and used to produce AAV2/9 $_{mini}$calmodulin-NPC.

The pre-clinical efficacy of AAV-$_{mini}$calmodulin-NPC as a treatment for NPC was accomplished in vivo. Npc1$^{-/-}$ mice (n=9) received 1×10$^{12}$ GC of AAV9-$_{mini}$CaMKII-NPC1 or an equivalent reporter control, AAV9-$_{mini}$CaMKII-GFP (n=6), between 20 and 25 days of life delivered by retroorbital injection. To achieve neuronal transduction, we relied upon the well-established property of AAV9 vectors to cross the blood-brain barrier and transduce neurons after systemic delivery. Relative to the untreated or AAV-GFP treated Npc1$^{-/-}$ mice [mean survival 66 days], the Npc1$^{-/-}$ mice that received AAV9-$_{mini}$CaMKII-NPC1 exhibited an increased life span (mean survival 105 days; P<0.02) Systemic delivery by retroorbital injection of AAV2/9 $_{mini}$calmodulin-NPC into Npc1$^{-/-}$ mice resulted in increased survival and mitigation of disease related symptoms. These results established this AAV as a successful gene therapeutic for NPC.

Example 2. Adeno-Associated Viral (AAV) Vector For NPC1 Delivery and Ubiquitous Expression A similar vector expressing the NPC1 gene from the elongation factor 1α (EF1α) promoter is also synthesized. While AAV2/9 $_{mini}$calmodulin-NPC directed the expression of NPC in neurons, the AAV2/9-$_{mini}$EF1α-NPC is expected to produce more widespread expression, because the elongation factor 1α promoter is known to direct expression in all cell types (ubiquitous). This gene therapy vector could be used to treat neurological, hepatic and other extraCNS symptoms in NPC patients. A truncated promoter was used to first create and AAV that expressed eGFP as a control. This AAV is called AAV-$_{mini}$EF1α-eGFP. Next, eGFP was excised, the WPRE element was removed both were replaced with the human NPC1 cDNA to create AAV-$_{mini}$EF1α-NPC1 and used to treat Npc1$^{-/-}$ mice.

Example 3. Therapeutic Treatment of NPC Subjects Using Adeno-Associated Viral (AAV) Vector For NPC1 Neuron-Specific Delivery Human NPC subjects are identified via methods known in the art, optionally including genetic testing of NPC1 and/or NPC2 loci to confirm phenotype-based diagnoses. NPC subjects are administered AAV-$_{mini}$calmodulin-NPC (optionally, AAV2/9 $_{mini}$calmodulin-NPC) by injection as a treatment for NPC. Other AAV serotypes will be used, such as AAVrh8 and AAV rh10. Following injection, one or more NPC-associated phenotypes (e.g., seizure incidence) and biomarkers (e.g., gangliosides, unesterified cholesterol) are assessed in treated NPC subjects and/or the level(s) of NPC1 or NPC2 mRNA or polypeptide expression is measured in the cells of NPC subjects, and is compared to a suitable control (e.g., baseline measurements pre-treatment, a control population of NPC subjects, etc.). The in vivo therapeutic efficacy of gene therapy treatment employing AAV and the AAV-$_{mini}$calmodulin-NPC vector of the invention is thereby identified.

Example 4. Therapeutic Treatment of NPC Subjects NPC1 Delivery and Ubiquitous Expression Human NPC subjects are identified via methods known in the art, optionally including genetic testing of NPC1 and/or NPC2 loci to confirm phenotype-based diagnoses. NPC subjects are administered AAV-$_{mini}$EF1α-NPC1 (optionally, AAV2/9 AAV-$_{mini}$EF1α-NPC1) by injection as a treatment for NPC. Other AAV serotypes will be used, such as AAVrh8 and AAV rh10. Following injection, one or more NPC-associated phenotypes (e.g., seizure incidence) and biomarkers (e.g., gangliosides, unesterified cholesterol, measures of hepatic function) are assessed in treated NPC subjects and/or the level(s) of NPC1 or NPC2 mRNA or polypeptide expression is measured in the cells of NPC subjects, and is compared to a suitable control (e.g., baseline measurements pre-treatment, a control population of NPC subjects, etc.). The in vivo therapeutic efficacy of gene therapy treatment employing AAV and the AAV-$_{mini}$EF1α-NPC1 vector of the invention is thereby identified.

Figure 4A:
FIG. 4 (A-G) show neuronal distribution of GFP in the Npc1$^{-/-}$ mouse brain after retro-orbital injection of AAV2/9-$_{mini}$CaMKII-GFP. (a) Excerpt from the Allen Brain Atlas, demonstrating the neuronal expression pattern of CaMKII in the wild type mouse brain. (b) Immunofluorescence of AAV9-$_{mini}$CaMKII-GFP in the Npc1$^{-/-}$ brain after retro-orbital injection. (c-g) Co-localization of the GFP signal with NeuN immunofluorescence, indicating incorporation of AAV2/9-$_{mini}$CaMKII-GFP into neuronal populations, including cortical pyramidal neurons (d, color removed in e to show double labeling, arrowheads) and CA3 hippocampal neurons (f, color removed in g to show double labeling, arrowheads).

Example 5. AAV9-$_{mini}$CaMKII-GFP Mediated Transduction of Neuronal Populations in Npc1$^{-/-}$ Mice An AAV vector that could both transduce and express human NPC1 gene in neurons was designed using a small neuro-specific promoter, CaMKII (375 bp). CaMKII was selected because it could be cloned into an AAV vector with NPC1 cDNA (3.8 kb) given the size limitation for AAV packaging. The final size of AAV vector including the 5' and 3' ITRs, which flanked the CaMKII promoter, NPC1 cDNA, and a polyadenylation signal, was around 4.8 kilobases. This vector construct was packaged using a serotype 9 capsid, which has been shown to be able to cross the blood brain barrier after systemic delivery and to be highly effective at transducing neurons. In order to define the tropism and expression pattern of AAV9-$_{mini}$CaMKII vector in vivo, a vector expressing the reporter, green fluorescent (AAV9-$_{mini}$CaMKII-GFP) was used. A single retro-orbital injection of 1×10$^{12}$ GC of AAV9-$_{mini}$CaMKII-GFP was performed into Npc1$^{-/-}$ mice at day of life 23. The expression pattern of the endogenous CaMKII promoter in an adult wildtype mouse is shown in FIG. 4a. Immunohistochemical imaging of the AAV9-$_{mini}$CaMKII-GFP treated Npc1$^{-/-}$ mice taken at 9 weeks of age showed a remarkably similar expression pattern, with strong GFP expression in the olfactory bulb, cerebral cortex, striatum and hippocampus, with weaker GFP expression throughout the midbrain and hindbrain (FIG. 4b).

Figure 4B:
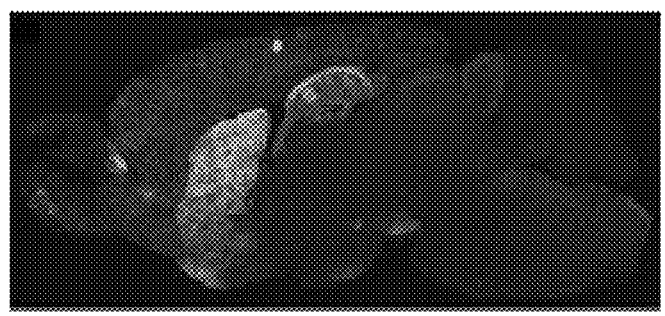
Figure 4C:
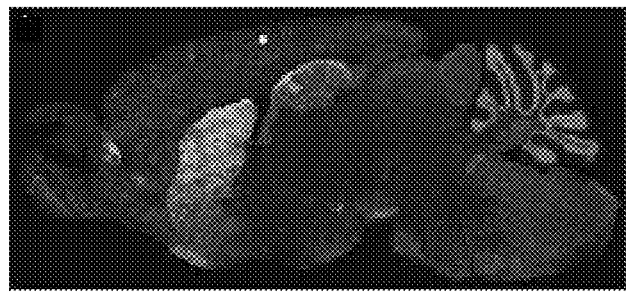
Figures 4D, 4E:
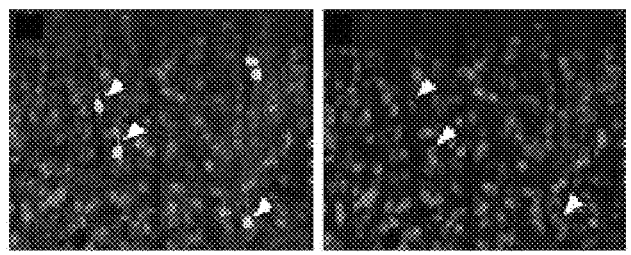
Figure 4F:
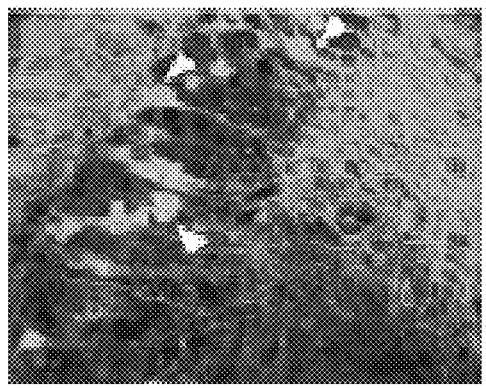
Figure 4G:
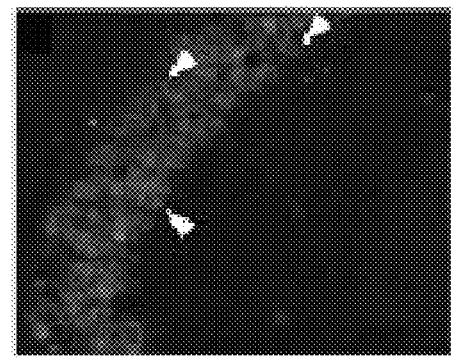

In contrast to the endogenous expression pattern, little cerebellar incorporation was observed (FIG. 4b). All GFP-positive cells were also labeled with NeuN, indicating that expression of the viral gene product only occurred in neurons (FIG. 4c). Higher magnification images of the cerebral cortex (FIG. 16d, e) and the CA3 field of the hippocampus (FIG. 4f, 4g) clearly show the neurospecific double-labeling (arrowheads) and neuronal morphology of the AAV9-$_{mini}$CaMKII-GFP transduced cells.

Figure 5A:
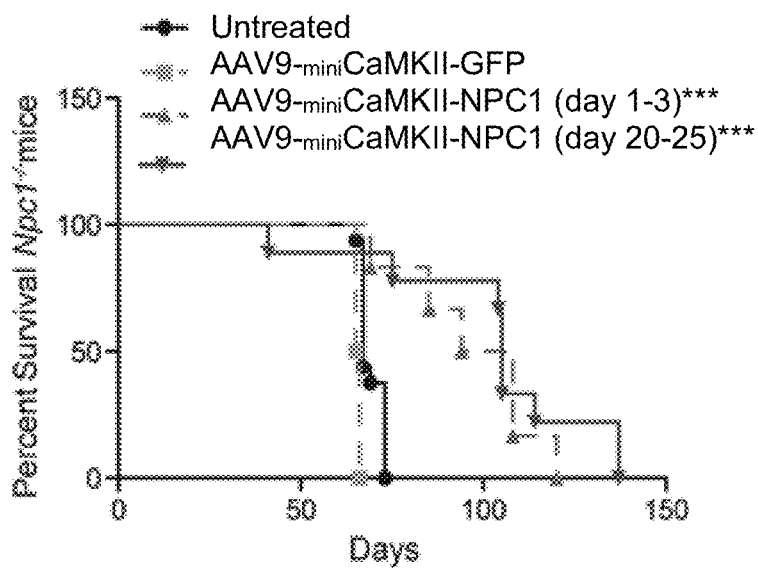
FIG. 5 (A-D) shows survival of Npc1$^{-/-}$ mice and growth following AAV9 treatments. (a) Kaplan-Meier Curve depicts survival of: Npc1$^{-/-}$ pups (n=6) treated with $2 \times 10^{11}$ GC of AAV2/9-$_{mini}$CaMKII-NPC1 between 1 and 3 days, Npc1$^{-/-}$ mice (n=9) treated with $1 \times 10^{12}$ GC of AAV2/9-$_{mini}$CaMKII-NPC1 between 20 and 25 days of life, Npc1$^{-/-}$ mice (n=6) treated with $1 \times 10^{12}$ GC of AAV2/9-$_{mini}$CaMKII-GFP between 20 and 25 days of life and untreated Npc1$^{-/-}$ mice (n=16). (b) Survival data depicted as a vertical scatter plot to show survival distribution. (c) Week at which Npc1$^{-/-}$ mice reached peak weight. (d) Percentage weight change between weeks 6 and 9. P<0.01, *P<0.001, Log-ranked (Mantel Cox) test or t-test two-tailed.
Figure 5B:
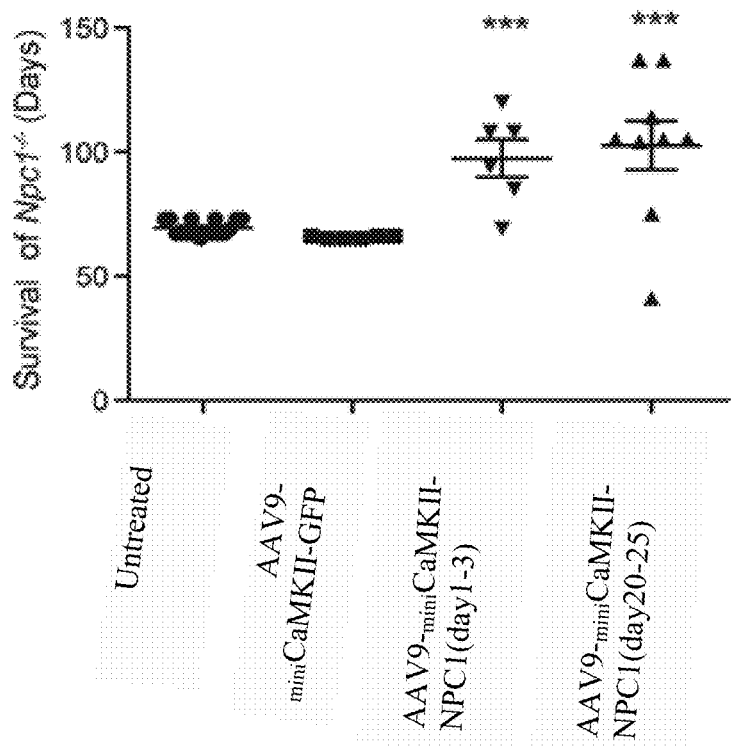

Example 6 AAV9-$_{mini}$CaMKII-NPC1 Gene Delivery Improves Survival and Delays Loss of Motor Function and Weight Decline of Npc1$^{-/-}$ Mice To test the efficacy of gene therapy as treatment for NPC at different delivery time points, Npc1$^{-/-}$ pups (n=6) received 2×10$^{11}$ GC of AAV9-$_{mini}$CaMKII-NPC1 between 1 and 3 days and Npc1$^{-/-}$ mice (n=9) received 1×10$^{12}$ GC of AAV9-$_{mini}$CaMKII-NPC1 between 20 and 25 days of life by retroorbital injection. A control group of Npc1$^{-/-}$ mice (n=6) received 1×10$^{12}$ GC of AAV9-$_{mini}$CaMKII-GFP between 20 and 25 days of life delivered by retroorbital injection. Consistent with previous reports, the untreated Npc1$^{-/-}$ mice (n=16) had a mean survival of 69 days and AAV9-$_{mini}$CaMKII-GFP treatment of Npc1$^{-/-}$ mice had no effect on survival with a mean survival of 65 days (FIGS. 5a and 5b). In contrast, Npc1$^{-/-}$ mice that received AAV9-$_{mini}$CaMKII-NPC1 at either 1-3 or 20-25 days of life exhibited an increased life span, with a mean survival of 97 and 103 days, respectively (P<0.001, FIGS. 5a and 5b). Relative to the untreated Npc1$^{-/-}$ mice, age matched AAV9-$_{mini}$CaMKII-NPC1 treated Npc1$^{-/-}$ mice at 8-9 weeks of life displayed physiological improvements that corresponded to an objective improvement in motor function, where mice appeared to maintain their strength and coordination to walk and explore the home-cage with reduced signs of tremor.

Figure 5C:
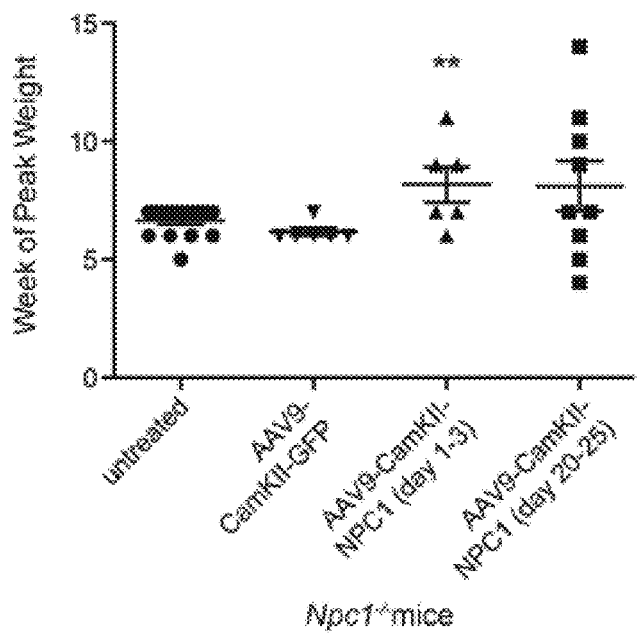
Figure 5D:
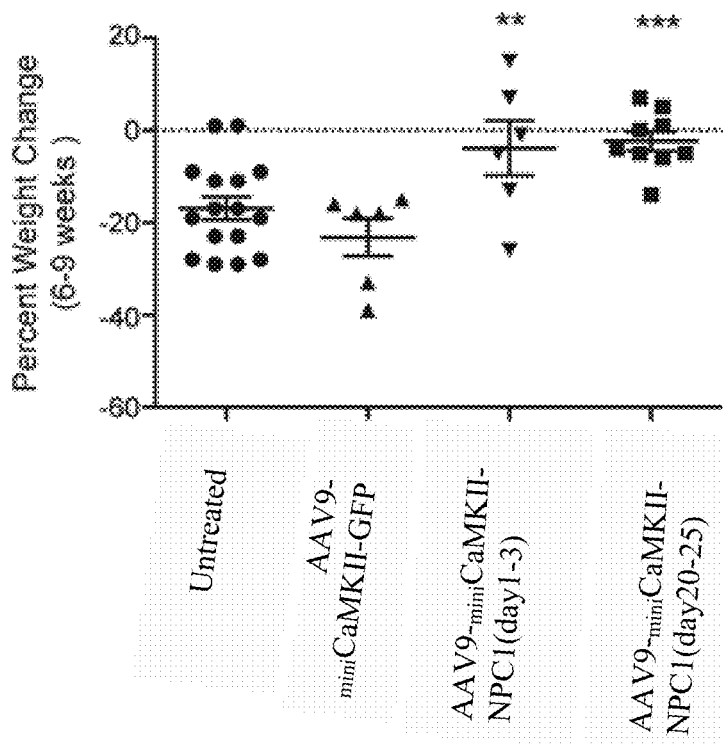

While gene delivery improved both survival and mobility of Npc1$^{-/-}$ mice, it had no significant effect on mass between 4 and 9 weeks. The week at which the Npc1$^{-/-}$ mice achieved their maximal or peak weight was used to determine if gene delivery delayed or prevent the weight loss that occurs in untreated Npc1$^{-/-}$ (FIG. 5c). Both untreated (n=16) and AAV9-$_{mini}$CaMKII-GFP treated (n=6) mice almost uniformly reach their peak weights at 6 weeks. While Npc1$^{-/-}$ pups (n=6) that received 2×10$^{11}$ GC of AAV9-$_{mini}$CaMKII-NPC1 between 1 and 3 days and Npc1$^{-/-}$ mice (n=9) that received 1×10$^{12}$ GC of AAV9-$_{mini}$CaMKII-NPC1 between 20 and 25 days of life on average reach their peak weight at 8 weeks (relative to untreated Npc1$^{-/-}$ mice P<0.01 and P=0.08, respectively). Because the weight decline of untreated mice began at 6 weeks and most untreated mice did not survive beyond 9 weeks, The percentage weight change from 6 to 9 weeks (% weight (wt) change=[wt$_{9weeks}$−wt$_{6weeks}$]/wt$_{6weeks}$×100) of untreated, AAV9-$_{mini}$CaMKII-NPC1 and AAV9-$_{mini}$CaMKII-GFP treated Npc1$^{-/-}$ mice (FIG. 5d) was compared. Untreated and AAV9-$_{mini}$CaMKII-GFP treated mice that had a percent weight change of −17% and −23%, respectively. Relative to untreated Npc1$^{-/-}$ mice, AAV9-$_{mini}$CaMKII-NPC1 Npc1$^{-/-}$ pups treated at 1-3 days and mice treated at 20-25 days demonstrated a significant reduction in weight loss, −3.8% (P<0.02) and −2.3% (P<0.001), respectively.

Example 7. AAV9-$_{mini}$CaMKII-NPC1 Treatment Increases NPC1 Protein Expression and Reduces Intracellular Accumulation of Cholesterol in Disease-Affected Brain Regions Layer V of the cerebral cortex (LV) and the CA3 pyramidal layer of the hippocampus (CA3) were chosen as ideal brain structures to assess the effectiveness of AAV9-$_{mini}$CaMKII-NPC1 administration. The pyramidal neurons in these regions are prone to high levels of unesterified cholesterol accumulation, but show no evidence of neuronal death in this mouse model, occluding cell loss as a confounding factor in our analysis. Retro-orbital administration of AAV9-$_{mini}$CaMKII-NPC1 was performed on Npc1$^{-/-}$ mice at day 23, with PBS-control injections made in corresponding Npc1$^{-/-}$ and Npc1$^{+/+}$ animals. Immunohistochemical assessment of the resulting Npc1$^{+/+}$ brain tissue at 9-weeks of age (FIG. 6a-6f) showed the stereotypical pattern of Npc1 protein expression and cholesterol localization. Npc1 staining was noted in NeuN positive neurons throughout the forebrain with no major intracellular accumulations of unesterified cholesterol observed by filipin staining, including the neocortical and hippocampal regions of interest. (L-V neurons; Npc1=12.04 mpi, filipin=5.84 mpi, FIG. 6c, 6d) (CA3 neurons; Npc1=10.63 mpi, filipin=2.05 mpi, FIG. 6e, 6f). The majority of the filipin signal in Npc1$^{-/-}$ mice was found in myelin-rich structures such as the corpus calosum. The reverse was true in the PBS injected Npc1$^{-/-}$ mice (FIG. 6g-6l). Almost no specific staining was detected with the Npc1 antibody, and many of the NeuN positive neurons throughout the forebrain exhibited the high levels of unesterified cholesterol accumulation typical of late-stage NPC disease pathology, including the LV (Npc1=2.98 mpi, filipin=28.9 mpi, FIG. 6i, 6j) and CA3 (Npc1=1.54 mpi, filipin=33.80 mpi, FIG. 6k, 6l) neurons.

Figure 6S:
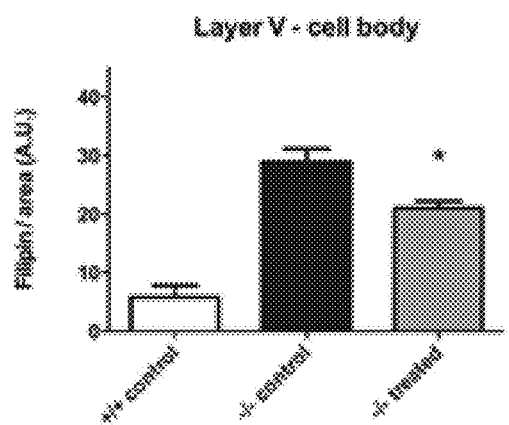
FIG. 6 (A-V) shows the effect of AAV2/9-$_{mini}$CaMKII-NPC1 treatment in the CA3 hippocampus and layer V neocortex of Npc1$^{-/-}$ mice. (a-r) Immunohistochemical imaging of Npc1 or NPC1 protein levels in the hippocampus and layer V neocortex, co-stained with NeuN and filipin. (a-f) Endogenous Npc1 expression in the Npc1$^{+/+}$ mouse, with NeuN stain removed in (b, d, f) to better show the neuronal Npc1 or NPC1 expression and magnified images of layer V neocortex (c-d) and CA3 hippocampus (e-f). (g-l) Endogenous levels of Npc1 or NPC1 protein in the Npc1$^{-/-}$ mouse, with NeuN stain removed in (h, j, l) to better show the lack of Npc1 or NPC1 expression and high level of intracellular filipin inclusions, with magnified images of layer V neocortex (c-d) and CA3 hippocampus (e-f). (m-r) NPC1 protein levels in the Npc1$^{-/-}$ mice injected with AAV2/9-$_{mini}$CaMKII-NPC1. NeuN stain removed in (n, p, r) to better show the presence of NPC1 expression in some neurons and the reduced level of intracellular filipin inclusions, with magnified images of layer V neocortex (o-p), and CA3 hippocampus (q-r). Quantification of filipin and Npc1 or NPC1 mean pixel intensity of the neuronal cell body in layer V neocortical neurons (s-t) and CA3 hippocampal neurons (u-v), data expressed as mean±S.E.M. A.U.=arbitrary units. *p<0.05, p<0.01, **p<0.0001, one-way ANOVA with Tukey's post-test.
Figure 6T:
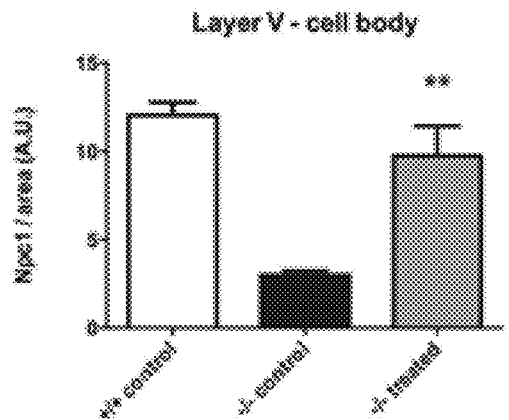
Figure 6U:
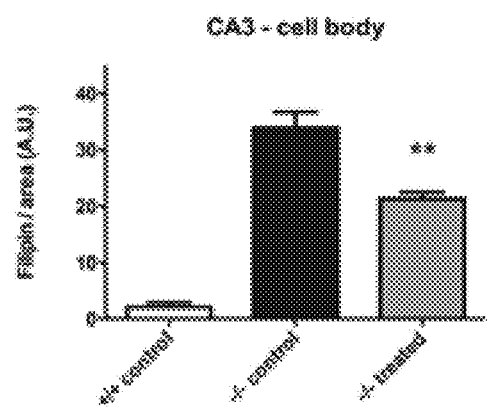
Figure 6V:
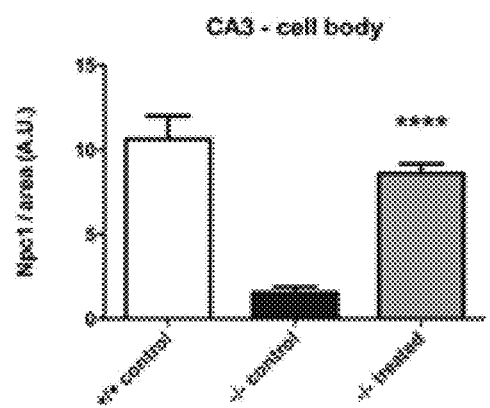

Analysis of the AAV9-$_{mini}$CaMKII-NPC1 treated Npc1$^{-/-}$ mice (FIG. 6m-6r) revealed an intermediate phenotype. While intracellular cholesterol accumulation was widespread throughout the brain, the average neuronal intracellular filipin intensity was 21.01 mpi in LV (FIGS. 6o, 6p) and 21.33 mpi in CA3 (FIG. 6q, 6r), significantly lower than observed in the PBS-control Npc1$^{-/-}$ mice (P<0.05 and P<0.01, respectively). This coincided with an NPC1 signal in AAV9-$_{mini}$CaMKII-NPC1 treated Npc1$^{-/-}$ neurons of 9.76 mpi in LV (FIGS. 6o, 6p) and 8.60 mpi in CA3 (FIG. 6q, 6r). While clearly below Npc$^{+/+}$ neuron levels, this still represents a significant increase of NPC1$^{-/-}$ protein in AAV9-$_{mini}$CaMKII-NPC1 treated Npc1$^{-/-}$ mice when compared to the Npc1$^{-/-}$ vehicle controls (P<0.01 and P<0.0001 respectively, all quantifications in FIG. 6s-6v).

Example 8. Biochemical Correction of Npc1$^{-/-}$ Neurons Following Gene Delivery Having identified that the AAV9-$_{mini}$CaMKII-NPC1 transduced NPC1-affected brain regions, induced production of NPC1 protein and reduced cholesterol pathology, it was determined whether the AAV-mediated expression of NPC1$^{-/-}$ was biochemically functional in a physiologically typical manner in Npc1$^{-/-}$ mice treated with AAV9 at day 23. Close inspection of the LV neuronal population in AAV9-$_{mini}$CaMKII-NPC1 treated mice revealed a punctate and perinuclear intracellular localization pattern for NPC1 protein, typical of a lysosomal distribution. In addition, LV neurons that lacked cholesterol accumulations were strongly NPC1-positive, while nearby weakly- or non-transduced neurons remained filipin positive (FIG. 7a, 7b).

Figure 7G:
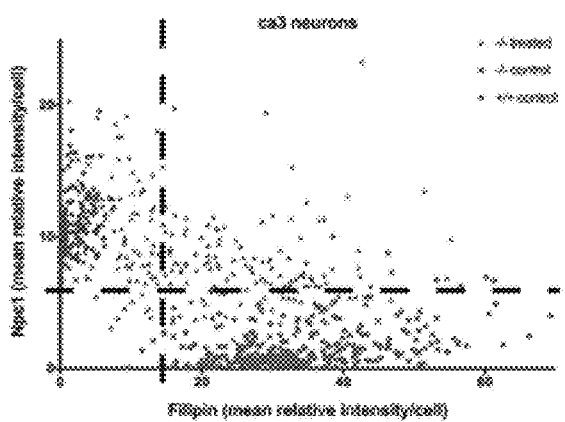
FIG. 7 (A-N) shows biochemical correction of the cholesterol storage phenotype in neurons transduced with AAV9-$_{mini}$CaMKII-NPC1 in the Npc1$^{-/-}$ mouse. Immunohistochemical imaging of NPC1 protein levels in the hippocampus (a-b) and layer V neocortex (e-f), co-stained with filipin and NeuN (in a and e only). Arrows indicate neurons without appreciable Npc1 protein and high filipin staining. Arrowheads indicate neurons successfully infected by the AAV9-$_{mini}$CaMKII-NPC1 with strong NPC1 staining and reduced filipin labeling. (c-d) NPC1 intensity of all layer V neurons measured, plotted against filipin intensity. (g-h) NPC1 intensity of all CA3 hippocampal neurons measured, plotted against filipin intensity. Upper left quadrants in (d, h) indicate the percentage of Npc1$^{-/-}$ neurons corrected to control levels with AAV9-$_{mini}$CaMKII-NPC1 treatment. Imaged density of AAV-$_{mini}$CaMKII-GFP (i j) and AAV9-$_{mini}$CaMKII-NPC1 (k-l) incorporation in the layer V cortex (i-k) and CA3 hippocampus (j-l), with quantification in (m-n). ns=non-significant.
Figure 7H:
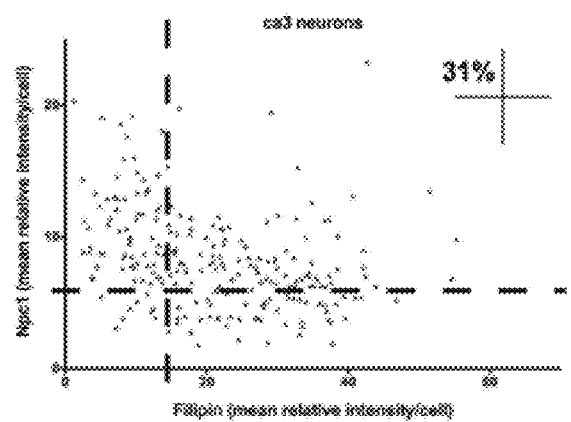

Plotting of NPC1 expression versus cholesterol accumulation of the LV neuron population analyzed in AAV9-$_{mini}$CaMKII-NPC1 treated mice against those of control Npc1$^{+/+}$ and Npc1$^{-/-}$ mice revealed that 21% (±5.71 S.E.M, n=4) had been biochemically corrected to normal levels (FIG. 7c, 7d). The same phenomenon was observed in the CA3 neurons, where 31% (±1.58 S.E.M, n=4) of this population in AAV9-$_{mini}$CaMKII-NPC1 treated mice was indistinguishable from normal, healthy neurons (FIG. 7e-7h).

Figure 7M:
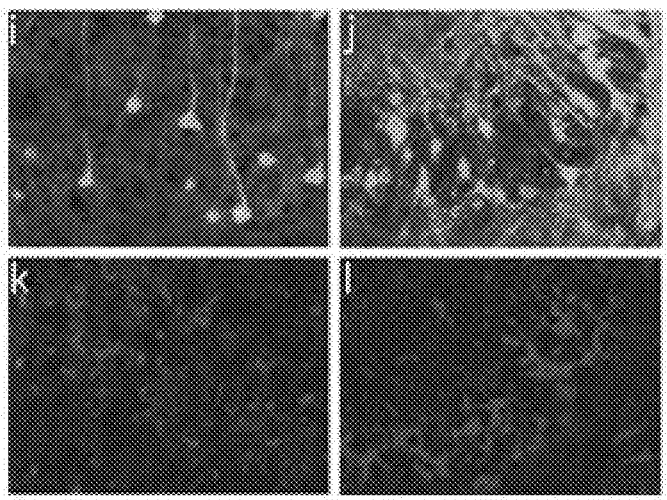
Figure 7M:
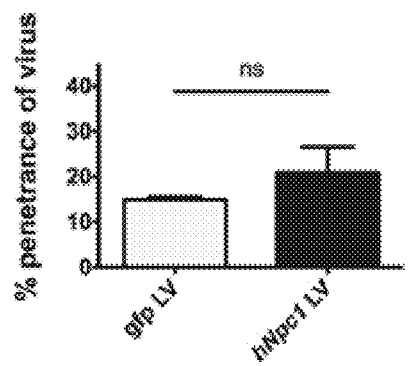
Figure 7N:
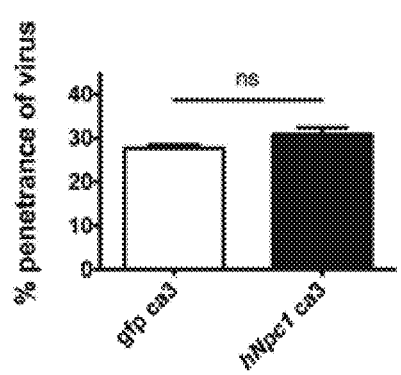

Comparison of the percentage of successfully transduced neurons in the AAV9-$_{mini}$CaMKII-GFP treated Npc1$^{-/-}$ mice (FIG. 7i, 7j) and the percentage of biochemically-corrected neurons in the AAV9-$_{mini}$CaMKII-NPC1 treated Npc1$^{-/-}$ mice (FIG. 7k, 7l) was made to assess whether the levels of biochemical correction directly matched the transduction pattern of the AAV-$_{mini}$CaMKII-GFP construct. Penetrance of the AAV9-$_{mini}$CaMKII-GFP was 14.9% (±0.60 S.E.M, n=3) in LV neurons, and 27.7% (±0.75 S.E.M, n=3) in CA3 neurons, not significantly different to that of the AAV9-$_{mini}$CaMKII-NPC1 (quantification in FIG. 7m, 7n), indicating the level of biochemical correction observed in Npc1$^{-/-}$ neurons corresponded to transduction pattern of the AAV9-$_{mini}$CaMKII-GFP construct.

Example 9. Delayed Purkinje Neuron Loss in Npc1$^{-/-}$ Mice Treated with AAV9-$_{mini}$CaMKII-NPC1

Figure 8A:
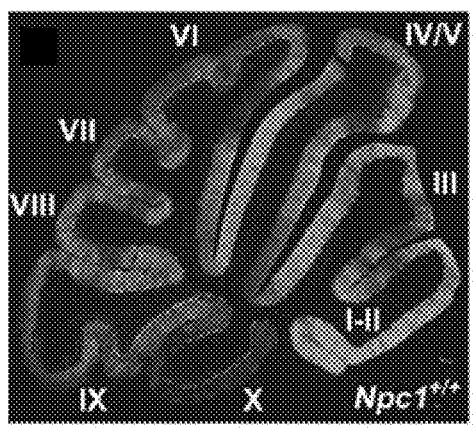
FIG. 8 (A-F) shows delayed Purkinje cell death after AAV2/9-$_{mini}$CaMKII-NPC1 treatment in Npc1$^{-/-}$ mice. Immunofluorescent calbindin staining of Purkinje cells in Npc$^{+/+}$ (a), Npc1$^{-/-}$ (b) and Npc1$^{-/-}$ (c) mice at 9 weeks of age (I-X=cerebellar lobular i.d. in c). (d-f) Quantification of Purkinje cell number in posterior cerebellar lobules. All data in bar-graphs expressed as mean±S.E.M., $*p<0.05$, $**p<0.01$, one-way ANOVA with Tukey's post-test.
Figure 8B:
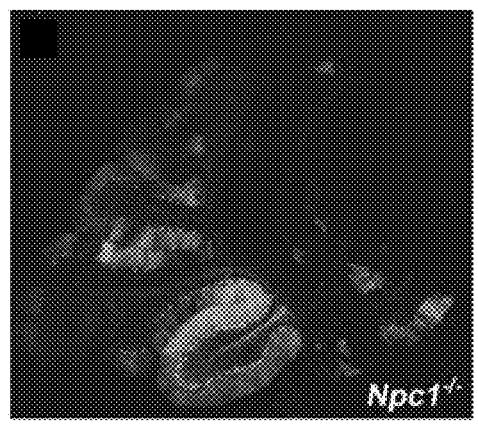
Figure 8C:
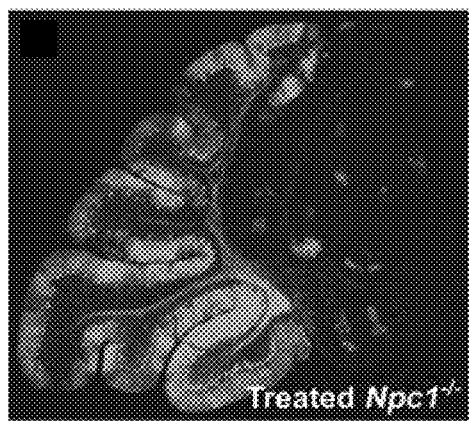
Figure 8D:
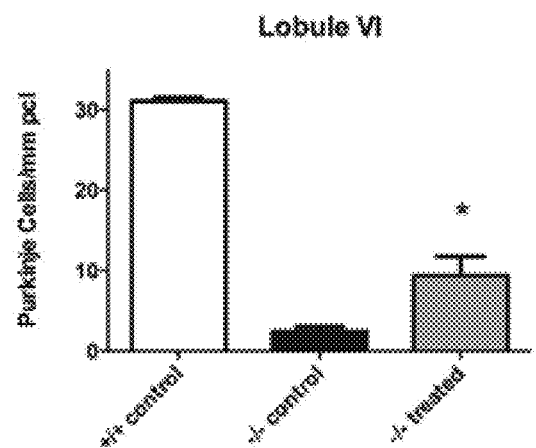
Figure 8E:
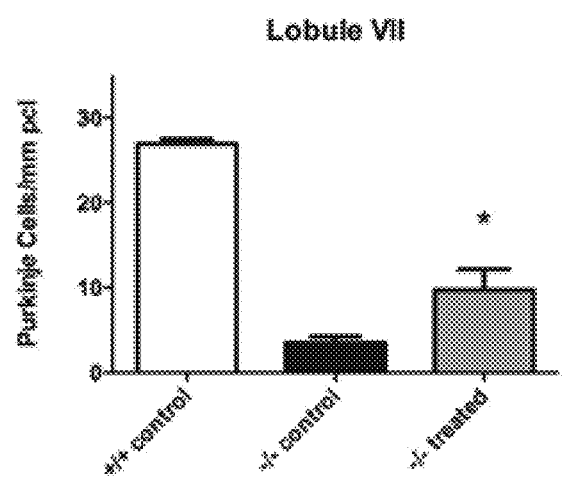
Figure 8F:
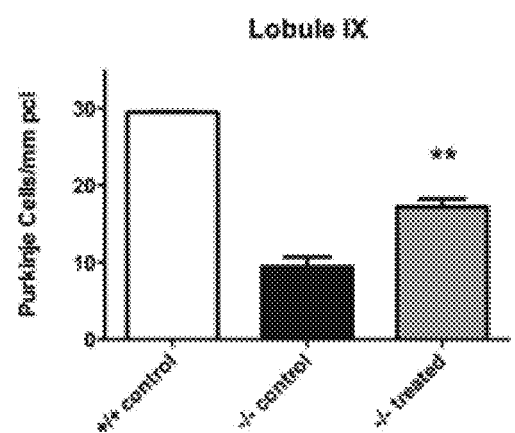

Significant improvements in lifespan and physiological criteria are usually accompanied by a preservation of cerebellar Purkinje cells in NPC1. Following immunohistochemical evaluation of Purkinje cell numbers at 9 weeks of age in our experimental groups, a significant delay in the typical anterior-to-posterior loss of these neurons upon AAV9-$_{mini}$CaMKII-NPC1 treatment (FIG. 8a-8e) was noticed. In the Npc1$^{+/+}$ control mice, Purkinje cell numbers remained at normal levels (31.01, 26.94, and 29.51 cells/mm of pc1 (Purkinje cells per mm of Purkinje cell layer:granule cell layer interface) in lobules VI, VII and IX respectively), but large-scale neuron loss was observed in Npc1$^{-/-}$ control mice (2.435, 3.523, and 9.469 cells/mm of pc1 in lobules VI, VII and IX respectively). While Purkinje cell loss had initiated in anterior lobules I-V in AAV9-$_{mini}$CaMKII-NPC1 treated Npc1$^{-/-}$ mice, significantly more neurons were still present when compared to the Npc1$^{-/-}$ control mice, with 9.374 cells/mm of pc1 in lobule VI (P<0.05), 9.716 cells/mm of pc1 in lobule VII (P<0.05), and 17.22 cells/mm of pc1 in lobule IX (P<0.01)(quantifications in FIG. 8f-8h), suggestive of an indirect AAV9-$_{mini}$CaMKII-NPC1 gene therapy-mediated delay in Purkinje cell death and motor function decline.

Figure 9:
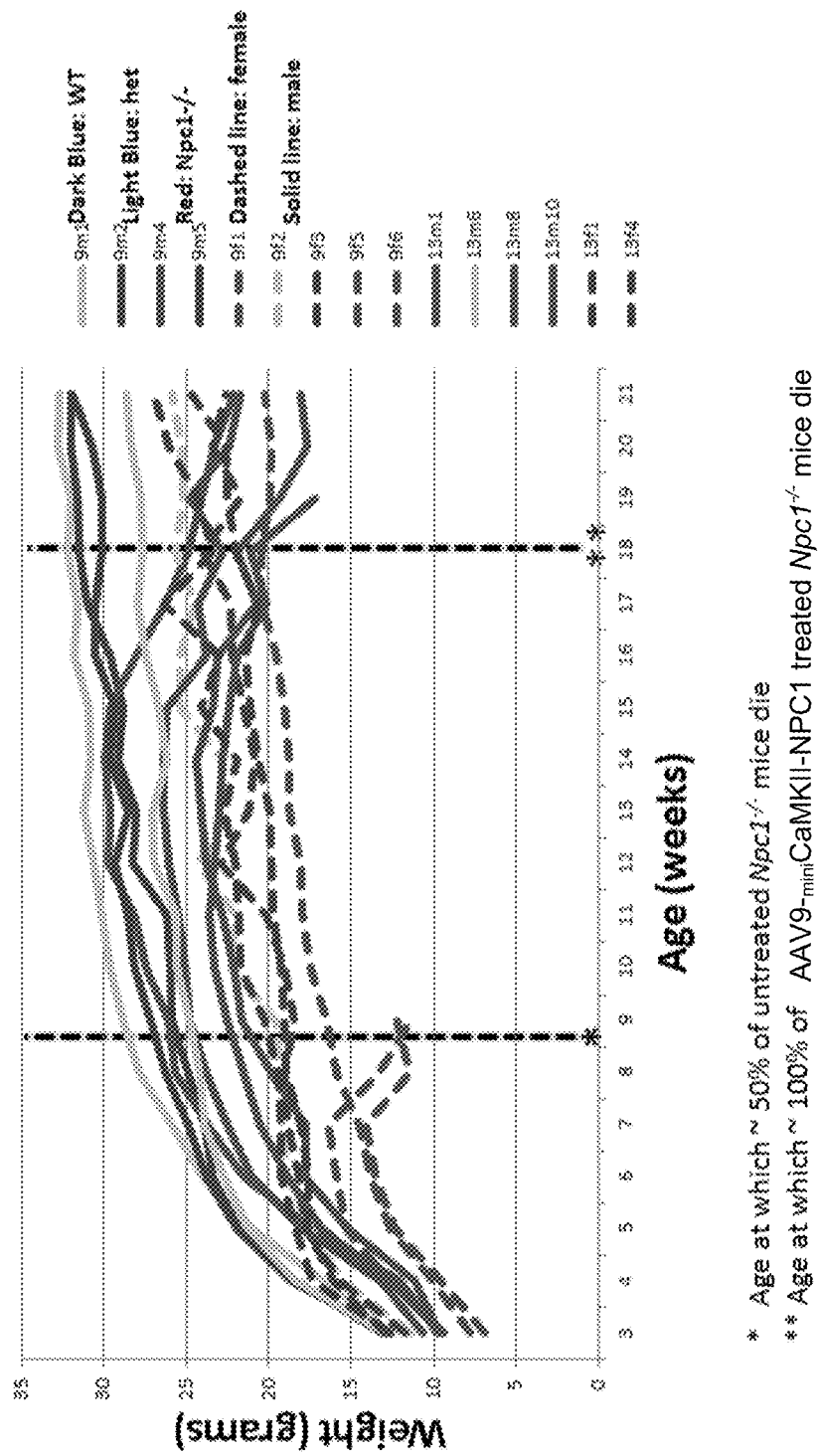
FIG. 9. Effect of AAV2/9-$_{mini}$EF1α-NPC1 treatment on Npc$^{-/-}$ mouse weight. Npc1$^{-/-}$ mice were injected retro-orbitally at p24 with 1.21e12 GC of AAV9-EF1a-NPC1. Survival and weight gain have been serially monitored since injection. Note that some of the treated mutants achieved weight equal to that of wild type, unaffected littermates and remarkably, have more than doubled survival compared to Npc1$^{-/-}$ controls (see FIG. 3). The cohort of mice in this pilot study are alive at the time of this PCT update. A comparison to *untreated and **AAV9-$_{mini}$CaMKII-NPC1 treated Npc1$^{-/-}$ mice is indicated at the bottom of the figure.

Example 10. AAV9-$_{mini}$EF1α-NPC1 Treatment Significantly Improves Survival and Increases Growth Relative to AAV9-$_{mini}$CaMKII-NPC1 Treatment (FIG. 9)

AAV9 vector that utilized a ubiquitous promoter was designed to determine whether AAV gene therapy used to correct both neuronal as well as other cell types in the brain and other organs might improve upon the efficacy that was observed with AAV9-$_{mini}$CaMKII-NPC1 gene delivery. The $_{mini}$CaMKII promoter was replaced with a truncated EF1α promoter (227 bp). The final size of AAV vector including the 5' and 3' ITRs, which flanked the EF1α promoter, NPC1 cDNA, and a polyadenylation signal, was 4.7 kilobases.

Figure 11:
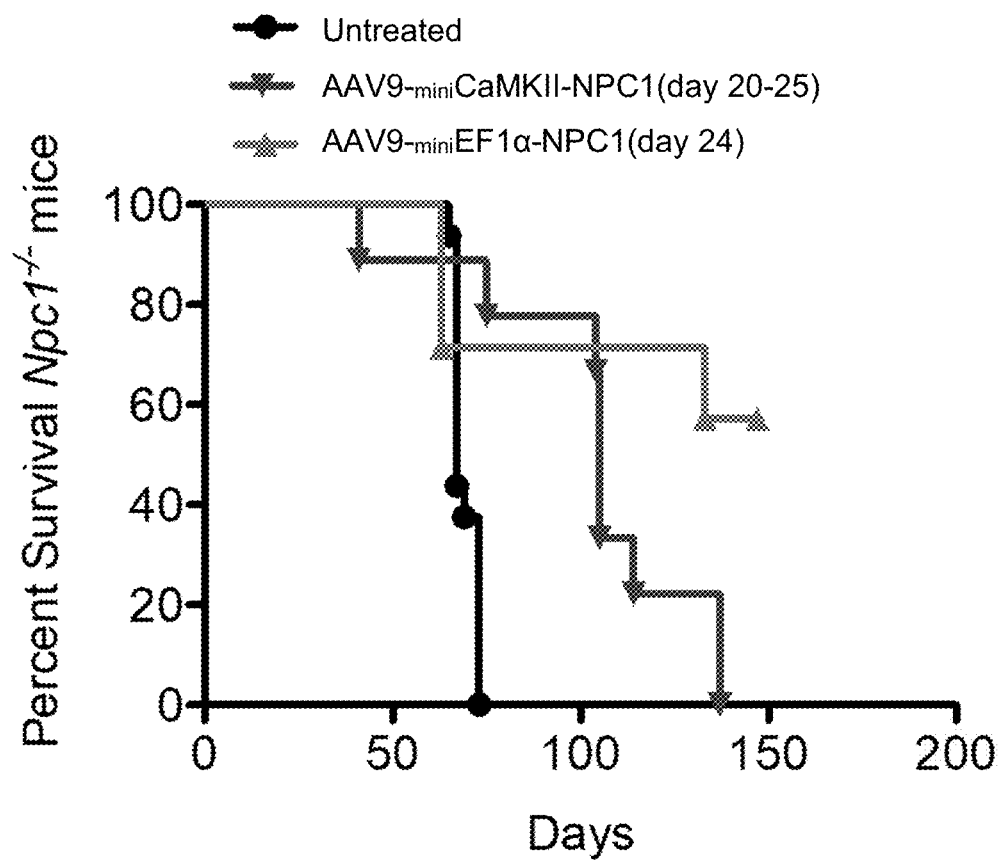
FIG. 11 shows survival differences between AAV2/9-$_{mini}$EF1α-NPC1 vs AAV2/9-$_{mini}$CaMKII-NPC1. Kaplan-Meier curve depicts survival of: untreated Npc1$^{-/-}$ mice (n=16), Npc1$^{-/-}$ mice (n=9) treated with $1\times10^{12}$ GC of AAV9-$_{mini}$CaMKII-NPC1 between 20 and 25 days of life, and Npc1$^{-/-}$ mice (n=7) treated with $1\times10^{12}$ GC of AAV9-$_{mini}$EF1α-NPC1 between 20 and 25 days of life. $***p<0.001$ compared to AAV9-$_{mini}$CaMKII-NPC1 treated Npc1$^{-/-}$ mice.

Npc1$^{-/-}$ mice (n=8) received 1×10$^{12}$ GC of AAV9-$_{mini}$EF1α-NPC1 at 24 days of life by retroorbital injection. Relative to Npc1$^{-/-}$ mice (n=9) treated with 1×10$^{12}$ GC of AAV9-$_{mini}$CaMKII-NPC1 between 20-25 days of life by retroorbital injection and untreated Npc1$^{-/-}$ mice (n=16) with a mean survival of 97 and 69 days, respectively, the AAV9-$_{mini}$EF1α-NPC1 treated Npc1$^{-/-}$ mice (n=8) had a significant increase (P<0.01) in survival with a mean survival >121 days (FIG. 11). Relative to the untreated Npc1$^{-/-}$ mice, age matched AAV9-$_{mini}$EF1α-NPC1 treated Npc1$^{-/-}$ mice at 8-9 weeks of life displayed physiological improvements that corresponded to an objective improvement in motor function, where mice appeared to maintain their strength and coordination to walk and explore the home-cage with reduced signs of tremor.

Figure 10A:
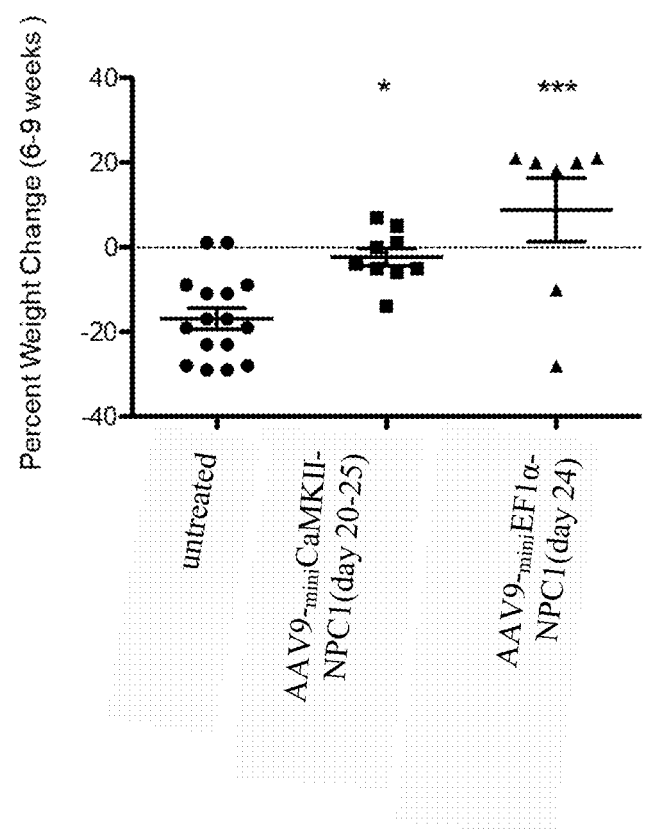
FIG. 10 (A-B) show weight effect of AAV2/9-$_{mini}$EF1α-NPC1 vs AAV2/9-$_{mini}$CaMKII-NPC1 treatment. Untreated or AAV treated Npc1$^{-/-}$ mice were serially weighed and compared to previous weights (a) or the age of peak weight; $*p<0.01$ $***p<0.001$ compared to untreated. (b). Mice treated with AAV2/9-$_{mini}$EF1α-NPC1 achieved a peak weight later than the other groups, showing the AAV gene therapy allows the mice to continue to gain weight much longer than untreated mice or those that received the AAV2/9-$_{mini}$CaMKII-NPC1 vector; $*p<0.01$.
Figure 10B:
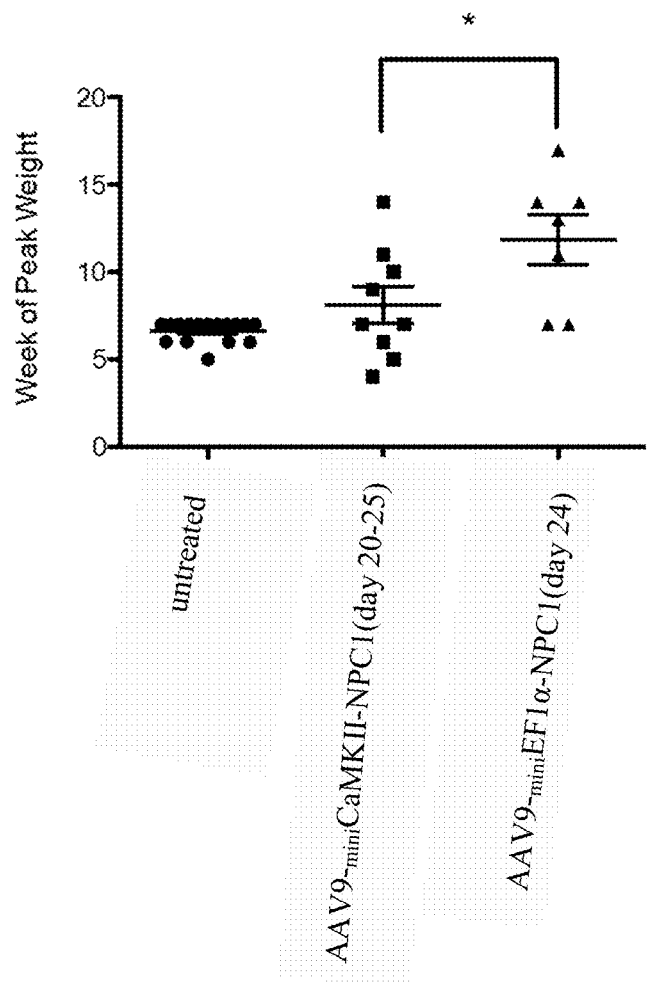

The AAV9-$_{mini}$EF1α-NPC1 treated Npc1$^{-/-}$ mice reached their mean peak weight at week 12, which was significantly later (P=0.02) than Npc1$^{-/-}$ mice treated with AAV9-CaMKII-NPC1 that reached their mean peak weight at week 8 (FIG. 10a). The mean percentage weight gain between 6 and 9 weeks for AAV9-$_{mini}$EF1α-NPC1 treated Npc1$^{-/-}$ mice was 8.8% and was greater than the mean percentage weight change for AAV9-$_{mini}$CaMKII-NPC1 treated Npc1$^{-/-}$ mice, which was -2.3%, but this difference was not significant (FIG. 10b).

Discussion

The studies were done to test the efficacy of AAV mediated gene delivery as a treatment for NPC1, a progressive and lethal neurological disease. AAV9 was selected for gene delivery because it has been shown to be able to cross the blood brain barrier and transduce neurons and glial cells, used successfully in many other murine models of inherited neurological diseases, and is being tested in human clinical to treat other inherit neurological diseases. The neuro-specific CaMKII promoter was selected first because of its small size and ability to express in Purkinje cells, the death of this class of neuron is thought to lead to the motor loss seen in NPC1 disease. AAV9-$_{mini}$CaMKII-NPC1 was delivered in the neonatal period and at 3 weeks of life to determine if treating the Npc1$^{-/-}$ mice early would increase the efficacy of AAV treatment.

Npc1$^{-/-}$ neonates and mice treated with AAV9-$_{mini}$CaMKII-NPC1 had a significant increased survival, superior motor activity at 9 weeks and delayed weight loss relative to untreated and AAV9-$_{mini}$CaMKII-GFP treated Npc1$^{-/-}$ mice. No significant difference in efficacy was observed regardless of the timing of the AAV9 delivery. The delayed delivery of AAV9 more accurately reflects the timing of AAV9 delivery in a potential human clinical trial as NPC1 disease is not typically diagnosed in the neonatal period.

Immunohistochemistry for NPC1/Npc1 and filipin staining confirmed that a subset of neurons of the AAV9 treated Npc1$^{-/-}$ mice expressed NPC1 and showed a corresponding reduction of filipin staining relative untreated Npc1$^{-/-}$ mice at 9 weeks. These results demonstrate a correlation between expression of NPC1 after gene deliver, a reduction in cholesterol storage, and an improvement of the NPC1 disease phenotype. However, substantially fewer transduced Purkinje neurons were detected in the cerebellum, an area where Purkinje neuron loss parallels the progression of the NPC1 disease in mouse model. The low transduction in the cerebellum may explain why AAV9-$_{mini}$CaMKII-NPC1 gene delivery only delayed the progression of the disease in the murine model of NPC1 and why mice did not achieve a normal life expectancy or the same weight as wild-type mice. Despite the lower AAV9 transduction in the cerebellum, the AAV9 treated mice had greater cerebellar Purkinje neuron survival at 9 weeks relative to untreated Npc1$^{-/-}$ mice.

Because the AAV9-$_{mini}$CaMKII-NPC1-treated Npc1$^{-/-}$ mice only achieved a modest increase in life expectancy, the vector was reengineered to express the NPC1 gene using a ubiquitous EF1α promoter in an attempt to improve the efficacy of the gene therapy that was initially observed. Npc1$^{-/-}$ mice treated with the new vector, AAV9-$_{mini}$EF1α-NPC1, shows a significant increase in life expectancy and growth relative to Npc1$^{-/-}$ mice treated with AAV9-$_{mini}$CaMKII-NPC. Since it utilized the same AAV9 serotype to deliver both vector constructs, the only difference between the two vectors are the cells types in which NPC1 is being expressed. This result suggests that correction of non-neuronal cells in the brain such as glial cells and/or cells types outside the central nervous system by AAV9-$_{mini}$EF1α-NPC1 is responsible for the increased therapeutic effect that was observed. More experiments will be need to determine the under lying differences in efficacy between these two AAV vectors and understanding these differences could lead to a further improvement of AAV gene therapy for NPC disease.

Currently, the Npc1$^{-/-}$ mice treated with AAV9-$_{mini}$EF1α-NPC1 are alive and appear relatively healthy, although their weights are lower than their wild-type littermates. Long-term monitoring of these AAV9-$_{mini}$EF1α-NPC1 treated mice will be required to determine how long the therapeutic benefit of AAV gene therapy will persist, but these results are extremely promising and further vector redesign may not be needed to justify advancement to clinical trials. However, further refinement of route of administration, promoter usage and/or combination with other interventions (such as 2-hydroxypropyl-β-cyclodextrin or HDACi) could potentially improve the effectiveness of AAV gene therapy as a treatment for NPC. These studies are first to demonstrate pre-clinical efficacy of AAV gene therapy as a therapeutic approach for NPC disease.

Materials and Methods Regarding Examples 5-10:

AAV vector design and production. The expression vector, pENN.AAV.$_{mini}$CaMKII0.4.eGFP.rBG (PL-C-PV1474) was obtained from the University of Pennsylvania Vector Core. This vector contains transcriptional control elements from the, mouse calcium/calmodulin-dependent protein kinase II (CaMKII) promoter, cloning sites for the insertion of a complementary DNA, and the rabbit 0-globin polyA signal. Terminal repeats from AAV serotype 2 flank the expression cassette. The eGPF cDNA was excised from pENN.AAV.$_{mini}$CaMKII0.4.eGFP.rB plasmid and replaced with the human NPC1 cDNA. This newly created vector was called AAV-$_{mini}$CaMKII-NPC1. These AAV vectors were packaged into an AAV9 capsid, purified by cesium chloride centrifugation, and titered by qPCR as previously described. The $_{mini}$CaMKII promoter was removed from the AAV-$_{mini}$CaMKII-NPC1 vector and replaced with a truncated EF1α($_{mini}$EF1α) promoter. The truncated EF1α promoter was cloned into an eGFP expression vector and transfected into 293T cells to test for promoter activity. The truncated EF1α expressed GFP in 293T cells at levels similar to the full length EF1α promoter. The AAV2/9-$_{mini}$CaMKII-NPC1 and AAV2/9-$_{mini}$EF1α-NPC1 vectors were produced by the Penn Vector Core at the University of Pennsylvania with published procedures.

Animals. All animal work was done according to NIH-approved animal care and use protocols. Heterozygous Npc1$^{+/+}$ mice (BALB/c Nctr-Npc1$^{m1N}$/J strain) were bred to obtain control (Npc1$^{+/+}$) and mutant (Npc1$^{-/-}$) littermates. Mice were weighed weekly and mutant mice were euthanized at 9 weeks of age, typically the disease end-stage in our colony as determined by rapid weight loss and severe loss of motor function. For evaluation of lifespan in AAV9-$_{mini}$CaMKII-NPC1 and AAV9-$_{mini}$CaMKII-GFP Npc1$^{-/-}$ treated groups, end-stage was determined using the same criteria.

Administration of AAV9. Neonatal Npc1$^{-/-}$ pups (1-3 days, n=6) received a retro-orbital injection of 2×10$^{11}$ GC of AAV9-$_{mini}$CaMKII-NPC1 in a total volume of 10 μls. Npc1$^{-/-}$ mice (20-25 days) received a retro-orbital injection of 1×10$^{12}$ GC of AAV9-$_{mini}$CaMKII-GFP (n=6) virus or AAV9-$_{mini}$CaMKII-NPC1 (n=9) virus in a total volume of 50 μls. Alternatively, Npc1$^{-/-}$ and Npc$^{+/+}$ received a sham injection of 50 μls at 23 days of age.

Immunohistochemistry. AAV9-$_{mini}$CaMKII-GFP treated Npc1$^{-/-}$ mice (n=3), AAV9-$_{mini}$CaMKII-hNPC1 Npc1$^{-/-}$ mice (n=4), control Npc1$^{-/-}$ mice (n=5) and control Npc1$^{+/+}$ mice (n=3) were taken at 9 weeks of age for immunohistochemical analysis. Mice were euthanized by CO$_2$ asphyxiation and transcardially perfused with 4% paraformaldehyde in phosphate buffer. The brains were post-fixed for 24 h then cryoprotected in 30% sucrose until the tissues sank. Brains were then cryostat-sectioned parasagittally (25 μm) and floating sections collected in phosphate buffered saline supplemented with 0.25% Triton-x100 (PBSt). Sections were incubated overnight at 4° C. with either rabbit anti-calbindin (1:3000, Swant), rabbit anti-Npc1 (1:2000), or mouse anti-NeuN (1:1000, MILIPORE) in PBSt, and the primaries detected using DyLight-488 goat anti-rabbit/mouse IgG or Alexa-594 anti-rabbit (1:1000 in PBSt, Vector Labs). Filipin (POLYSCIENCES INC.) staining was performed at final concentration of 50 μg/ml in PB St. Sections were mounted and coverslipped with ProLong Gold mounting medium (Life Technologies).

Image Analysis. Images of the whole cerebellum or hippocampal/neocortical region were taken using a Zeiss Axio Observer Z1 microscope fitted with an automated scanning stage, Colibri II LED illumination and Zeiss ZEN software using a high-res AxioCam MRm camera and a 20× objective. Each fluorophore channel was pseudo-coloured in ZEN, exported as TIFF, and analyzed using the FIJI distribution of ImageJ, adjusting each channel for brightness and contrast in an identical manner across all experimental groups.

For CA3 hippocampal and Layer V neocortical neuron analysis, the area of a neuron was delineated according to the cell body size determined by NeuN staining and the mean pixel intensity (mpi) of the filipin and Npc1 stain within the cell recorded. Every $5^{th}$ neuron was chosen at random along the CA3 or layer V axis to obtain a representative neuronal population. 20 cells were counted in each region per section, and 3 sections counted per brain (60 cells per n). To assess the level of biochemical correction in the AAV9-$_{mini}$CaMKII-NPC1 treated neuronal population, gating boundaries were set at the lower 2% of the filipin and Npc1 intensities of the Npc1$^{-/-}$ and Npc1$^{+/+}$ control groups, respectively. Neurons with "lower than disease-baseline" levels of cholesterol storage together with "above wildtype-baseline" levels of Npc1 expression were considered biochemically corrected.

To analyze the transduction of the AAV9-$_{mini}$CaMKII-GFP virus, the total number of NeuN positive neurons was measured in a set area of CA3 hippocampus or Layer V neocortex, and the % of those cells double-labeled with GFP recorded (3 sections counted per brain, minimum of 72 cells counted in each section, total of 1086 hippocampal and 2367 neocortical neurons measured).

Purkinje cells were counted by measuring the number of calbindin positive Purkinje cell bodies with recognizable dendritic tree or axonal projection still remaining within a given cerebellar lobule. Data was expressed as the number of Purkinje cells per mm of Purkinje cell layer:granule cell layer interface (pcl). The entire lobule was counted per section, with 3 sections counted per brain.

Statistical Analysis. Results are expressed as means±S.E.M. and analyzed for statistical significance by ANOVA, where $P<0.05$ using Tukey's post-test was considered significant. Kaplan-Meier survival curves were tested for significance using the Log-Rank Mantel-Cox test, where results were considered significant using a Bonferroni-corrected threshold of $P<0.0083$ to account for multiple comparisons. All statistics were calculated using Graphpad Prizm software.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

Reference for AAV Anc80: Zinn E, Pacouret S, Khaychuk V, Turunen H T, Carvalho L S, Andres-Mateos E, Shah S, Shelke R, Maurer A C, Plovie E, Xiao R, Vandenberghe L H. In Silico Reconstruction of the Viral Evolutionary Lineage Yields a Potent Gene Therapy Vector. Cell Rep. 2015 Aug. 11; 12(6):1056-68. doi: 10.1016/j.celrep.2015.07.019. Epub 2015 Jul. 30. PubMed PMID: 26235624; PubMed Central PMCID: PMC4536165.

Reference for AAV PHP.B: Deverman B E, Pravdo P L, Simpson B P, Kumar S R, Chan K Y, Banerjee A, Wu W L, Yang B, Huber N, Pasca S P, Gradinaru V. Cre-dependent selection yields AAV variants for widespread gene transfer to the adult brain. Nat Biotechnol. 2016 February; 34(2):204-9. doi: 10.1038/nbt.3440. Epub 2016 Feb. 1. PubMed PMID: 26829320.

What is claimed is:

1. A method for treating or preventing a cholesterol storage disease or disorder in a subject, the method comprising:
administering a composition comprising (1) a therapeutically effective amount of an adeno-associated virus (AAV) viral vector comprising (a) a first AAV2 inverted terminal repeat (ITR) having exactly 130 base pairs, (b) a mini-elongation factor 1 α ($_{mini}$EF1α) promoter, (c) an NPC1 gene sequence operably linked to the $_{mini}$EF1α promoter, (d) a rabbit beta globin poly A signal, and (e) a second AAV2 ITR having exactly 130 base pairs, and (2) a pharmaceutically acceptable carrier to the subject,
wherein the cholesterol storage disease or disorder is caused by mutation or malfunction in the NPC1 gene of the subject,
thereby treating or preventing the cholesterol storage disease or disorder in the subject.

2. The method of claim 1, wherein the subject is a mammal.

3. The method of claim 1, wherein the AAV viral vector is encapsidated with the AAV serotype 9 capsid.

4. The method of claim 1, wherein the therapeutically effective amount is $5 \times 10^{12}$ gc/ml or more.

5. The method of claim 1, wherein the AAV viral vector comprises a viral capsid selected from AAV2, AAV3, AAV4, AAV5, AAV6, AAV7, AAV8, AAV9, AAV rh8, AAVrh10, AAVrh33, AAV rh34, AAV Anc80, and AAV PHP.B viral capsid.

6. The method of claim 1, wherein the $_{mini}$EF1α promoter consists of the nucleotide sequence of SEQ ID NO: 8.

7. The method of claim 1, wherein (a) through (e) of the AAV viral vector comprise no more than 4.7 kilobases.

8. A method for treating or preventing a cholesterol storage disease or disorder in a subject, the method comprising:
administering a composition comprising (1) a therapeutically effective amount of a viral vector comprising (a) a mini-elongation factor 1 α ($_{mini}$EF1α) promoter and (b) an NPC1 gene sequence operably linked to the $_{mini}$EF1α promoter, and (2) a pharmaceutically acceptable carrier to the subject,
wherein the cholesterol storage disease or disorder is caused by mutation or malfunction in the NPC1 gene of the subject,
thereby treating or preventing the cholesterol storage disease or disorder in the subject.

9. The method of claim 8, wherein the subject is a mammal.

10. The method of claim 8, wherein the viral vector is an adeno-associated viral (AAV) vector.

11. The method of claim 10, wherein the AAV viral vector comprises a viral capsid selected from AAV2, AAV3, AAV4, AAV5, AAV6, AAV7, AAV8, AAV9, AAV rh8, AAVrh10, AAVrh33, AAV rh34, AAV Anc80, and AAV PHP.B viral capsid.

12. The method of claim 8, wherein the $_{mini}$EF1α promoter consists of the nucleotide sequence of SEQ ID NO: 8.

13. The method of claim 8, wherein the viral vector comprises SEQ ID NO: 7.

\* \* \* \* \*